(12) United States Patent
Serebrennikova et al.

(10) Patent No.: US 7,952,693 B2
(45) Date of Patent: May 31, 2011

(54) DETECTING MICROORGANISMS IN BLOOD UTILIZING PHYSICAL AND CHEMICAL CHANGES IN BLOOD

(75) Inventors: Yulia M. Serebrennikova, St. Petersburg, FL (US); Debra Huffman, St. Petersburg, FL (US); Jennifer M. Smith, St. Petersburg, FL (US); Luis H. Garcia-Rubio, St. Petersburg, FL (US); German F. LeParc, St. Petersburg, FL (US)

(73) Assignee: Claro Scientific LLC, St. Petersburg, FL (US)

( * ) Notice: Subject to any disclaimer, the term of this patent is extended or adjusted under 35 U.S.C. 154(b) by 211 days.

(21) Appl. No.: 12/263,807

(22) Filed: Nov. 3, 2008

(65) Prior Publication Data

US 2009/0115996 A1    May 7, 2009

Related U.S. Application Data

(60) Provisional application No. 60/996,192, filed on Nov. 6, 2007.

(51) Int. Cl.
  *G01N 33/48* (2006.01)
(52) U.S. Cl. ......................................... 356/39
(58) Field of Classification Search ............... 356/39–42
  See application file for complete search history.

(56) References Cited

U.S. PATENT DOCUMENTS

| 4,152,213 A | 5/1979 | Ahnell |
| 5,422,720 A | 6/1995 | Berndt |
| 5,427,920 A | 6/1995 | Berndt et al. |
| 5,770,394 A | 6/1998 | Berndt |
| 5,983,122 A | 11/1999 | Jarman et al. |
| 6,379,920 B1 | 4/2002 | El-Sayed et al. |
| 6,514,277 B1 * | 2/2003 | Lilge et al. ................ 607/88 |
| 6,944,485 B1 * | 9/2005 | Van Meter et al. ............ 600/310 |
| 6,984,526 B2 * | 1/2006 | Garcia-Rubio et al. ...... 436/171 |
| 7,027,134 B1 * | 4/2006 | Garcia-Rubio et al. ........ 356/39 |
| 7,027,143 B1 | 4/2006 | Stokowski et al. |
| 2002/0122168 A1 * | 9/2002 | Garcia-Rubio et al. ........ 356/39 |

FOREIGN PATENT DOCUMENTS

WO    WO 02/04947 A2    1/2002

OTHER PUBLICATIONS

James M. Neill Ph.D. "Studies on the Oxidation Reduction of Hemoglobin and Methemoglobin", J. Exp. Med. 41: 535-549 (1925).
Naomi M. Anderson Ph.D. et al., "Light-Absorbing and Scattering Properties of Non-haemolysed Blood", Phys. Med. Biol. 1967, vol. 12, No. 2, 173-184.
W.G. Zijlstra et al., "Absorption Spectra of Human Fetal and Adult Oxyhemoglobin, De-Oxyhemoglobin Carboxyhemoglobin, and Methemoglobin", Clin. Chem. 37/9, 1633-1638, 1991.

(Continued)

*Primary Examiner* — Michael P Stafira
(74) *Attorney, Agent, or Firm* — Stephen A. Bent; Foley & Lardner LLP

(57) ABSTRACT

An approach to detecting microorganisms in blood uses the changes of hemoglobin and the physical and chemical properties of blood to detect the presence of microorganisms in blood. Spectrophotometric measurements are taken several wavelengths across the UV-Vis-NIR portion of the electromagnetic spectrum, and a deconvolution is performed quantitatively to interpret distinct spectral characteristics of blood enabling the detection of microorganisms.

46 Claims, 41 Drawing Sheets

OTHER PUBLICATIONS

K. Razi Naqvi et al., "Absorption and scattering of light by suspensions of cells and subcellular particles: an analysis in terms of Kramers-Kronig relations", Photochem. Photobiol. Sci., 2004, 3, 132-137.

F.A. Rodrigo, M.S., "The Determination of the Oxygenation of Blood Invitro by Using Reflected Light", American Heart Journal 45, 809-822 (1953).

Moritz Friebel et al., "Determination of the complex refractive index of highly concentrated hemoglobin solutions using transmittance and reflectance measurements", Journal of Biomedical Optics, 10(6), 064019-1-064019-5, 2005.

Joseph M. Schmitt et al,. "New Methods for Whole Blood Oximetry", Annals of Biomedical Engineering, vol. 14, pp. 35-52, 1986.

Larry Reynolds et al., "Diffuse reflectance from a finite blood medium: applications to the modeling of fiber optic catheters", Applied Optics vol. 15, No. 9, pp. 2059-2067, Sep. 1976.

Robert A. MaCrae et al., "Spectral Transmission and Scattering Properties of Red Blood Cells", Journal of the Optical Society of America, vol. 51, No. 12, Dec. 1961, pp. 1366-1371.

William D. Welch et al., "Variability in $CO_2$, and pH, Levels in Blood Culture Bottles from Five Different Manufacturers", Journal of Clinical Microbiology, vol. 20, No. 5, Nov. 1984, pp. 881-883.

Catalina E. Alupoaei et al., "An Interpretation Model for the UV-VIS Spectra of Microorganisms", Chem. Eng. Comm. 192: 198-218, 2005.

W.J. Wiscombe, "Improved MIE Scattering Algorithms", Applied Optics, vol. 19, No. 9, May 1, 1980, pp. 1505-1509.

Curtis C. Johnson, "Optical Diffusion of Blood", IEEE Transactions on Bio-Medical Engineering, vol. BME-17, No. 2, Apr. 1970, pp. 129-133.

Longzhu Cui et al.,"Cell Wall Thickening is a Common Feature of Vancomycin Resistance in Staphylococcus aureus", Journal of Clinical Microbiology, vol. 41, No. 1, Jan. 2003, pp. 5-14.

International Search Report PCT/US2008/012408 dated Jul. 21, 2009.

Jennifer M. Smith et al., "A New Method for the Detection of Microorganisms in Blood Cultures: Part I. Theoretical Analysis and Simulation of Blood Culture Processes", The Canadian Journal of Chemical Engineering, vol. 86, Oct. 2008, pp. 947-959.

Yulia M. Serebrennikova et al., "Quantitative interpretations of Visible-NIR reflectance spectra of blood", Optics Express, Oct. 27, 2008, vol. 16, No. 22, pp. 18215-18229.

Communication Pursuant to Article 94(3) EPC dated Nov. 5, 2010 Application No. 08 847 250.1-2402.

Roxanne DeSlauriers et al., "Oxygen consumption in *Plasmodium berghei*-infected murine red cells: a direct spectrophotometric assay in intact erythrocytes", Biochimica et Biophysica Acta 886 (1986) 319-326.

\* cited by examiner

FIG. 24

| Vessel Parameters and Experimental Conditions | |
|---|---|
| Total volume of the culture bottle [cm$^3$] | 76.8 |
| Volume of culture media [mL] | 40 |
| Culture preparation temperature [°C] | 25 |
| Incubation temperature [°C] | 37 |
| pH of the media | 7.24 |
| Inert gas (N$_2$) partial pressure [mmHg] | 0.0 |
| Initial O$_2$ partial pressure [mmHg] | 80 |
| Initial CO$_2$ partial pressure [mmHg] | 20 |
| Blood Parameters | |
| Volume of blood [mL] | 2 - 20 |
| Hematocrit [Erythrocyte volume fraction] | 0.45 |
| Total hemoglobin [g/dL] | 15.0 |
| Erythrocyte mean corpuscular volume [fL] | 90.0 |
| Mean Corpuscular Hemoglobin Concentration | 0.33 |
| Leukocyte concentration [k/μL blood] | 5 |
| Platelet concentration [k/μL blood] | 326 |
| Blood O$_2$ partial pressure [mmHg] | 35 -100 |
| Blood CO$_2$ partial pressure [mmHg] | 40 - 60 |
| Cell Population Metabolism | |
| Rate constant for leukocyte decay [1/hr] | -1.3946 |
| Leukocyte respiration rate constant [gmol/(min-O$_2$-N$_{WBC}$)] | $4.534 \times 10^{-12}$ |
| Rate constant for platelet decay [1/hr] | -1.3946 |
| Platelet respiration rate constant [gmol/(min-O$_2$-N$_{PLT}$)] | $6.45 \times 10^{-14}$ |
| Microorganism inoculum [N$_{ORG}$/mL blood] | 100 |
| Microbial doubling time [min] | 20 |
| Microbial respiration rate constant [gmol /(min-O$_2$-N$_{ORG}$)] | $6.06 \times 10^{-9}$ |
| Limiting No. of organisms [N$_{ORG}$/mL-culture] | $1.0 \times 10^8$ |

Blood Culture Cell Counts

Effect of the Blood Volume

DETECTING MICROORGANISMS IN BLOOD UTILIZING PHYSICAL AND CHEMICAL CHANGES IN BLOOD

BACKGROUND OF THE INVENTION

This section is intended to provide a background or context to the invention that is recited in the claims. The description herein may include concepts that could be pursued, but are not necessarily ones that have been previously conceived or pursued. Therefore, unless otherwise indicated herein, what is described in this section is not prior art to the description and claims in this application and is not admitted to be prior art by inclusion in this section.

U.S. Pat. No. 5,422,720 and U.S. Pat. No. 5,770,394 illustrate extant technology for the detection of metabolic products, particularly $CO_2$, resulting from the growth of microorganisms present in blood culture bottles. See also U.S. Pat. No. 6,379,920 (direct comparison of the spectral features of organisms grown in standard media and in blood culture bottles) and U.S. Pat. No. 5,427,920 (detecting the presence of microbial growth through measuring the intensity of back-scattered light).

Thus, the literature describes a variety of methods for determining the presence of microorganisms in blood. The presence of microorganisms typically is detected by means of an internal indicator for the production of a microbial metabolic product, such as $CO_2$. Illustrative in this regard are optical monitoring of changes in a $CO_2$-sensitive disk in the bottom of blood culture bottles (U.S. Pat. No. 5,770,394) and pressure-sensitive techniques that measure increased production of $CO_2$ in the head space of a culture bottle. Other methodology has related changes in back-scattered light peak intensity at a few wavelengths to the presence of microorganisms. For example, see U.S. Pat. No. 5,427,920.

These approaches have not been employed commercially, however, because of difficulties in the variable nature of blood compositions and changing initial conditions for a given experiment. More specifically, all of the existing microorganism detection methods have sensitivities that depend on the particular measurement technique employed and on the following factors:

1. the rate of production of metabolic $CO_2$ or other metabolic products;
2. the transport of the metabolic products to an indicator dye (typically, dyes are immobilized in a solid matrix that is integrated with the culture bottle, for ease of detection);
3. the transport of metabolic gases from the liquid culture media to the bottle headspace; and
4. the time constant associated with reaction of metabolic products and the indicator dye.

The constituency of a given spectrophotometric-indicator dye system determines its sensitivity to the presence of metabolic products, particularly in terms of the minimum detectable $CO_2$ concentration. The time to detection (TTD) depends on the sensitivity of the measurement technique, the time required to reach the minimum detectable $CO_2$ concentration, and on the transport and reaction time constants. The rate of growth and, therefore, the rate of production of metabolic $CO_2$ depends on the initial concentration of organisms (CFU/mL of blood) and on the incubation conditions (growth media, temperature, etc.), as well as the strain of organism itself. Existing detection systems require between $10^8$-$10^9$ microorganisms/mL for positive detection with an incubation or amplification time corresponding to the specific growth rate of each organism.

A conventional spectrophotometric-indicator dye system requires adding indicator dyes or other labels to the system, and does not yield any clinical information beyond the presence or absence of microorganisms. A system is needed, therefore, that provides for sensitive and efficient measurements of microorganisms without a requirement for additional materials and steps and provide more meaningful information about the character of the microorganisms present.

SUMMARY OF THE INVENTION

The present invention provides methodology and apparatus that overcome the disadvantages of conventional measurement techniques for detecting microbial contamination in vitro. In particular, the invention relates changes in (A) the physical and chemical properties of a blood sample, in the number and size of cells and other particulates present, and in the fraction of hemolyzed red blood cells in the sample to (B) the presence and character of contaminating organisms in the sample.

Pursuant to an embodiment of the invention, these changes are measured by spectrophotometric procedures across the ultraviolet, the visible range, and/or the near-infrared (UV-Vis-NIR) portions of the electromagnetic spectrum. The spectral features are related to the physical and chemical properties of blood via correlational and/or spectral deconvolution techniques. The correlational approach relates features within portions of the measured spectra to specific changes in the properties of blood. The complete spectra or portions thereof also can be interpreted via spectral deconvolution techniques, which require an appropriate mathematical description of the data. This mathematical description of the data can be but is not necessarily limited to theoretical, empirical, and statistical descriptions.

The present invention overcomes the disadvantages of current measurement techniques by allowing detection to occur in the absence of additional indicators or dyes. Changes in the physical and chemical properties of blood can be exploited to detect the presence of microbial activity directly (e.g., by particle counts) or indirectly by monitoring changes in the chemical composition of blood (e.g., by hemoglobin composition). The various embodiment of the present invention take advantage of the fact that hemoglobin is present in large concentrations, is well-dispersed through culture media either in free form or in red blood cells, and its spectrum changes as a function of ambient conditions. The distinct spectral differences between the different forms of hemoglobin allow for greater detection sensitivity by enabling small changes in hemoglobin chemical composition to be quantified. Moreover, simultaneous measurements of spectral signatures over multiple wavelengths result in improved statistical analyses.

For carrying out the approach of the invention, an apparatus configuration preferably includes: (i) at least one light source that can deliver illumination within the UV-Vis-NIR portion of the spectrum and (ii) devices such as fiber optics to deliver and collect light from the sample from a suitable number of wavelengths. Two example spectroscopy configurations suitable for this purpose are diffuse reflectance and diffuse transmittance. These configurations take advantage of the absorption and multiple-scattering properties of blood, and, in contrast to an extant approach, do not require the placement of a fiber optic probe directly against the wall of the blood culture vessel.

The present invention thus provides, in accordance with one of its aspects, a method for assessing the presence of microorganisms in blood, comprising (a) emitting electromagnetic radiation into at least one blood sample, (b) measuring wavelength-dependent spectra of re-emitted electromagnetic radiation from the blood sample, wherein said measuring is of one or both of transmittance signals and reflectance signals, and then (c) deconvoluting the spectra to assess the presence or absence of microorganisms in the blood sample. In one embodiment, the spectra are quantitatively interpreted in terms of physical and chemical properties of blood. In a different embodiment, the deconvoluting determines the presence or absence of multiple types of microorganisms in blood. Furthermore, the method can comprise the step of extracting identifying characteristics of the microorganisms from the spectra.

Pursuant to an exemplary embodiment, the aforementioned spectra can be measured as a function of time or at any discrete time point. Measuring step (b) is preferably of diffuse transmittance or reflectance signals, but it may be of angular transmittance signals or reflectance signals. In an exemplary embodiment, the re-emitted electromagnetic radiation comprises wavelengths in the ultra-violet range, the visible range, an/or the near infra-red range. In yet another exemplary embodiment, the deconvoluting step quantifies the physical and/or chemical properties of blood components. According to another exemplary embodiment, the deconvolution step comprises at least one of linear or non-linear models and resolves the spectra into a particle-related physical characterization. In another exemplary embodiment, a method of the invention quantifies at least one form of hemoglobin. In this regard, the deconvolution step (i) can comprises at least one of a linear model and a non-linear model and (ii) can resolve the spectra into the hemoglobin form.

According to another example embodiment, the assessing comprises detecting the presence or absence of microorganisms. In a different example embodiment, the method further comprises extracting identifying characteristics of the microorganisms from the spectra. In this regard, the identifying characteristics are selected from the group comprising kinetic growth parameters and physical characteristics. Alternatively, or additionally, the growth parameters can include doubling times and respiration rates, and/or the physical characteristics may include size and shape. In yet a different example embodiment, the presence or absence of microorganisms is assessed in accordance with changes in properties of blood induced by one or more microbial metabolites.

In accordance with another aspect, the present invention also provides apparatus configured to assessing the presence of microorganisms, comprising (a) a spectrometer configured to measure spectra of a plurality of wavelengths emitting from a sample of blood, (b) a transmission cell and/or a reflectance probe that is operably connected to the spectrometer, and (c) a computer that (i) is operably connected to the spectrometer and (ii) is configured to perform deconvolution on the spectra, thereby to assess the presence or absence of microorganisms in the sample. In one embodiment, the spectrometer includes a diode array. In another embodiment, a reflectance probe is operably connected to the spectrometer and is configured such that it does not touch the container in which the sample is located.

The present invention provides, in accordance with another of its aspects, a method of assessing the presence of at least one microorganism in blood, comprising (a) emitting electromagnetic radiation into at least one blood sample in a closed container, (b) measuring wavelength-dependent spectra of re-emitted electromagnetic radiation from the blood sample, wherein the measuring is of one or both of transmittance signals and reflectance signals, then (c) deconvoluting the spectra, (d) determining partial pressure values associated with at least one of oxygen and carbon dioxide in the headspace above the blood sample and (e) assessing the presence or absence of microorganisms in accordance with the partial pressure values.

Another aspect of the present invention relates to a method of assessing the presence of at least one microorganism in blood, comprising (a) emitting electromagnetic radiation into at least one blood sample in a closed container, (b) measuring wavelength-dependent spectra of re-emitted electromagnetic radiation from the blood sample to obtain measured spectral values, wherein the measuring is of one or both of transmittance signals and reflectance signals, (c) measuring partial pressure values associated with at least one of oxygen and carbon dioxide in a headspace above the blood sample to obtain measured partial pressure values, (d) deconvoluting the spectra in accordance with the measured spectral values and the measured partial pressure values, and (e) assessing the presence or absence of microorganisms in accordance with said deconvoluting.

These and other advantages and features of various embodiments of the present invention, together with the organization and manner of operation thereof, will become apparent from the following detailed description when taken in conjunction with the accompanying drawings.

BRIEF DESCRIPTION OF THE DRAWINGS

Embodiments of the invention are described by referring to the attached drawings, in which:

FIG. 24 is a table of exemplary parameters associated with various experiments conducted in accordance with various embodiments of the present invention;

DETAILED DESCRIPTION OF PREFERRED EMBODIMENTS

Figure 1:
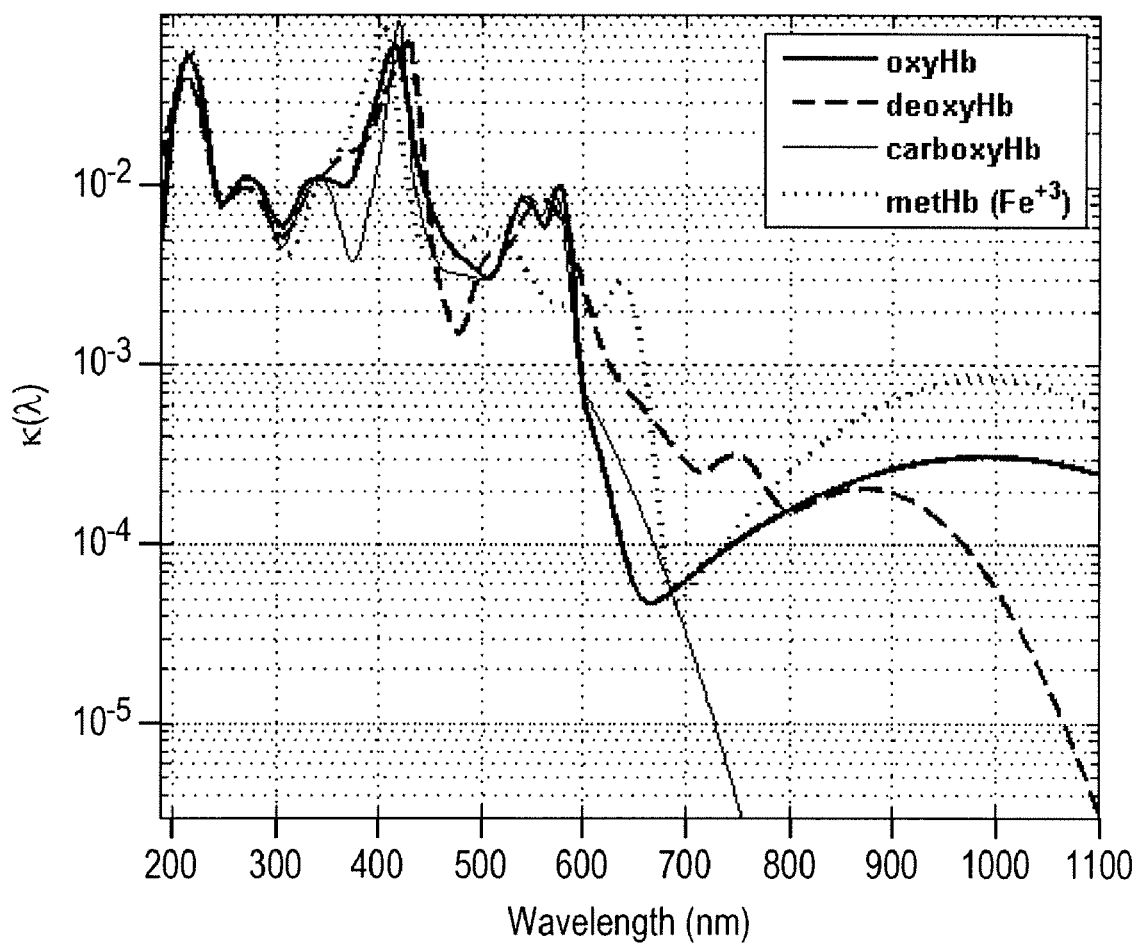
FIG. 1 illustrates an exemplary absorption coefficients of the four common forms of hemoglobin: oxy-, deoxy-, carboxy-, and met-hemoglobin.

In the following description, for purposes of explanation and not limitation, details and descriptions are set forth in order to provide a thorough understanding of the present invention. However, it will be apparent to those skilled in the art that the present invention may be practiced in other embodiments that depart from these details and descriptions.

Pursuant to the present invention, microbial contamination in a blood sample may be detected via transmittance or reflectance measurements taken across a spectrum of light. The transmittance or reflectance is obtained after emitting light against the blood sample in a container. After the spectra are collected from the remitted radiation, the data are subsequently deconvolved into its component parts using mathematical descriptions, such as theoretical models. See Jansson, P. A., DECONVOLUTION: WITH APPLICATIONS IN SPECTROSCOPY (Academic Press, 1984). The goal of this process is to determine the model parameters that relate to the state of the physical properties of blood, and relate to its chemical composition. The interpretation of the parameters in turn relates to characteristics such as doubling time, respiration range, size, and shape, and partial pressures of gases such as oxygen and carbon dioxide, thereby typifying microorganisms present in the sample.

In keeping with this approach, the present invention provides both methodology and apparatus for detecting microorganisms in blood, for instance, in a blood culture bottle. More specifically, the invention exploits changes in the physical and chemical properties in blood (e.g., hemoglobin composition), as well as partial pressures of gases such as oxygen and carbon dioxide in the head space of the blood culture, to detect the presence and identifying characteristics of organisms. These changes are detected via spectrophotometric procedures that accommodate or are suited to the UV-Vis-NIR portion of the electromagnetic spectrum. Pursuant to the various embodiment of the present invention, spectral measurements thus obtained are interpreted quantitatively by means of spectral deconvolution techniques. This approach encompasses real-time monitoring of the physical and chemical changes in blood.

A. Changes in Blood Composition Effected by Microorganisms

It is well established that the presence of organisms in blood induces changes in the optical properties of blood, for example, by causing the composition of hemoglobin to change and by hemolyzing red blood cells. For example, see U.S. Pat. No. 5,427,920, U.S. Pat. No. 5,770,394, and U.S. Pat. No. 6,379,920. These changes are brought about by the metabolic functions and metabolic by-products of the microbial growth. As early as the 1920's it was established that aerobic and anaerobic organisms, either through their direct oxidation-reduction systems or through their metabolic by-products (notably $CO_2$), act on oxy-hemoglobin to convert it into deoxy-hemoglobin and, under the appropriate conditions, into met-hemoglobin or into other forms of hemoglobin, such as carbamino-hemoglobin, carboxy-hemoglobin, or other hemoglobin by-products. See U.S. Pat. No. 5,427,920. Since hemoglobin, free or in red blood cells, is in relatively high concentrations in a blood culture, it may be used for detecting biological activity and, hence, the presence of microorganisms.

B. Measuring Changes in Blood Composition

The optical properties of hemoglobin are detailed extensively in the literature. See, e.g., Neill, *J. Exp. Med.* 41: 535-49 (1925), Anderson et al., *Phys. Med. Biol.* 12: 173-84 (1967), and Perkampus, UV-VIS ATLAS OF ORGANIC COMPOUNDS, $2^{nd}$ ed., part 2 (1992). FIG. 1 shows typical variations of absorption coefficient as a function of wavelength for oxy-, deoxy-, carboxy-, and met-hemoglobin, respectively. Significant differences in their spectral features are apparent, and these differences enable the quantification of small changes in hemoglobin composition. See Dubova et al., *Zh. Prikl. Spektrosk.* 36: 76-82 (1980), and Zijlstra et al., *Clin. Chem.* 37: 1633-38 (1991). Researchers designing non-invasive, reflectance-based instrumentation for oximetry, particularly pulse oximetry, exploit these small spectral differences. For example, see: Naqvi et al., *Photochem. Photobiol. Sci.,* 132-37 (2004); Rodrigo, *Am. Heart J.* 45: 809 (1953); Zijlstra, W. G., A MANUAL OF REFLECTION OXIMETRY (1958); van Assendelft, O. W., SPECTROMETRY OF HAEMOGLOBIN DERIVATIVES (1970); and U.S. Pat. No. 5,983,122.

Accordingly, there is ample evidence indicating that different forms of hemoglobin can be determined quantitatively from the spectra of blood samples. See Friebel et al., *J. Biomed. Optics* 10: 064019-1 to 064019-5 (2005), and Dubova et al. and Zijlstra et al. (1991), supra. Detecting relatively small changes in hemoglobin composition also can reduce significantly the time required for determining the presence of organisms in a sample.

Diffuse transmission and diffuse reflectance are two techniques that can be applied in making such measurements. See, e.g., Mignani et al. "In Vivo Medical Sensors," in OPTICAL FIBER SENSORS, Dakin et al., eds. (1997); Kortum G. REFLECTANCE SPECTROSCOPY (1969). These techniques take advantage of the observation that blood and blood suspensions diffusely scatter light at concentrations typically used for in vitro cultures. Hapke, B. THEORY OF REFLECTANCE AND EMITTANCE (1993); Schmitt et al., *Ann. of Biomed. Eng.* 14: 35-52 (1986); Reynolds et al., *Appl. Optics* 15: 2059-67 (1976); McRae et al., *J. Opt. Soc. of America* 51: 1366-72 (1961). In the case of reflectance measurements, this observation is particularly important.

Figure 2:
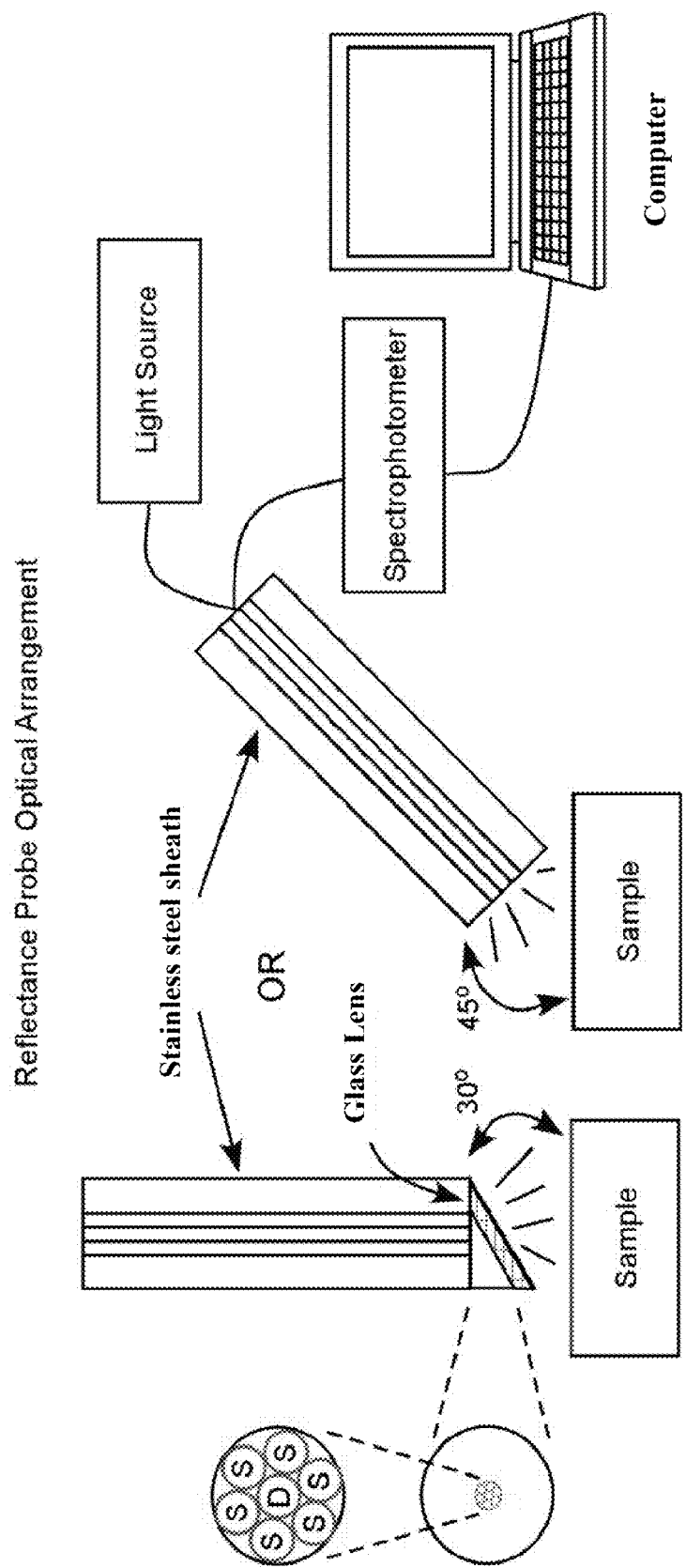
FIG. 2 depicts a reflectance measurement apparatus that may be used for conducting spectral measurements in accordance with the various embodiments of the present invention.

Diffuse reflectance measurements do not require the source (i.e., illuminating fiber) or the detector (i.e., receiving fiber) to be collimated. See Mignani et al., Kortum et al., and Hapkie et al., supra. Moreover, these measurements do not require probe placement directly on the surface of the sample container. See Kortum et al. and compare U.S. Pat. No. 5,427,920, both discussed above. FIG. 2 depicts an example of a commercially available fiber optic configuration suitable for diffuse reflectance measurements.

The spectral region between 190-1100 nm is particularly suitable for collimated and diffuse transmittance measurements, whereas the spectral region between 400-1100 nm is ideal for angular and diffuse reflectance. It should be noted that, in this context, the term "collimated" refers to the use of a parallel beam of photons impinging upon a sample. The stream of photons can be observed across the sample (transmittance) or from the reflected radiation. If the source is "diffuse" then the light will impinge on the sample from many directions. Accordingly, the direction of the transmitted and scattered light relative to the incident light may not be established. "Diffuse" reflectance pertains when light is reflected in all directions uniformly; hence, observations from any direction are equivalent. By contrast, "angular" measurements are a function of angle and, typically, are used in conjunction with collimated sources.

C. Model Implementation

In order to utilize the physical and chemical properties of blood as indicators of the presence of microorganisms, it is necessary to relate observed changes in these properties to corresponding measured spectra. This can be accomplished effectively using deconvolution techniques on the measured spectral data. See Jansson, DECONVOLUTION (1984), supra. To this end, mathematical descriptions, such as theoretical models, have been developed to perform the deconvolution. In practice, a model, selected to represent the spectral data, i.e., a theoretical model describing the underlying physics and chemistry, is fitted to the measured spectra. For instance, the physical and chemical properties of blood, such as changes in the hemoglobin composition, are resolved by fitting the spectra predicted from the theoretical model to the measured spectra. These changes are related directly to the presence of microorganisms. Furthermore, the results of the deconvolution process using theoretical models include the determination of doubling times, respiration rates, and other physical characteristics of the microorganisms, such as size and shape, as well as the value and rate of change in partial pressures of gasses such as oxygen and carbon dioxide.

Deconvolution techniques can be employed using different mathematical descriptions of the spectral data that may be associated with fundamental lineshapes, chromophoric groups, and scattering patterns, depending on what type of information is to be extracted from the blood sample. These mathematical descriptions include but are not limited to theoretical, empirical, and statistical models. These models may have representations that are (i) mathematical (i.e., comprising functions or equations), and/or (ii) statistical (i.e., comprising principal components or databases). In all cases, the parameters implicit in the description of the spectra are affected by the following exemplary variables:

composition of growth media;

composition of the head space, including partial pressure of gasses such as oxygen and carbon dioxide;

initial composition of the blood sample, and in particular, its level of oxygenation;

concentration of red blood cells; and/or concentration and type of microorganisms present in the blood sample.

An additional variable is the rate of change of an indicator, such as hemoglobin, composition in blood culture, which may be a function of:

the initial indicator concentration in the blood sample (for example, in case of hemoglobin, expressed as total hemoglobin or hematocrit); and/or the initial concentration and rate of growth of microorganisms present in the blood sample, where the latter is governed, at least in part, by the type of microorganism(s) present. Note that the rate at which an indicator, such as hemoglobin, changes is proportional to the $O_2$ concentration, which in turn is proportional to the number of microorganisms present and their rate of respiration.

According to the principles of the present invention, a model has been implemented that is capable of describing the following four distinct time intervals relevant to changes in an indicator, such as hemoglobin, composition and other physical and chemical properties of the sample. This model is based on the analysis of different variables that affect the spectra, such as the variables listed above.

1. An initial equilibration, during which hemoglobin equilibrates with gas compositions dissolved in the growth media and in the head space. During this period, red blood cells may change size and shape (e.g. swelling, lysis, crenation, and the like), depending on the composition of the media.

2. A second interval of microbially-induced changes in hemoglobin composition and/or physical properties of blood corresponding to the beginning of the "lag-phase" in the culture growth (i.e., when the number of organisms increases at a slow rate, for example, corresponding to about $1$-$10^3$ CFU/mL).

3. A third interval of rapid change in the hemoglobin composition and/or physical properties of blood that occurs during the exponential growth phase of the microorganisms (approximately $10^6$-$10^7$ CFU/mL).

4. A fourth interval that is characterized by continuing transformation of hemoglobin and/or the physical properties of blood corresponding to the completion of the exponential growth phase and beginning of a stationary phase of the culture (typically between $10^8$-$10^9$ CFU/mL).

The spectra, obtained either by transmittance and/or reflectance, can, therefore, be resolved in terms of hemoglobin composition and/or the physical properties of blood at any point during the culturing process.

Pursuant to the present invention, the deconvolution can employ but is not limited to using a standard least-squares estimation. See Welch et al., *J. Clin. Micro.* 20: 881-83 (1984), Lawson et al., SOLVING LEAST SQUARES PROBLEMS (1974), and Jansson, supra. The standard least-squares solutions may be implemented from linear and non-linear interpretation models for both transmission and reflectance. These models are further described in greater detail in the sections that follow.

D. Models

1. Linear Interpretation Models

Linear interpretation models can be derived for both transmission and reflectance measurements under appropriate approximations.

i. Transmission Models: The Beer-Lambert law is applicable to transmission measurements when the scattering effects have been reduced to a minimum (for example, when the red blood cells have been hemolyzed) and the hemoglobin is in solution. Under these conditions, the optical densities may be represented by:

$$\tau(\lambda) = \alpha(\lambda)C + \epsilon \quad (1)$$

Where, $\tau(\lambda)$ represents the vector of optical densities as a function of wavelength, $\lambda$, $\alpha(\lambda)$ is the matrix of absorption coefficients of the forms of hemoglobin as a function of wavelength, $\lambda$, C represents the vector of concentrations of the forms of hemoglobin considered, and $\epsilon$ represents the error associated with the measurements. The ordinary least squares solution is given by:

$$C = (\alpha^T \alpha)^{-1} \alpha \tau \quad (2)$$

Where, the notation $(\cdot)^T$ represents the transpose of the matrix $(\cdot)$, and the notation $(\cdot)^{-1}$ represents the inverse of the matrix $(\cdot)$.

ii. Reflectance Models: One of the most successful models for reflectance measurements is the Kubelka-Munk equation, which relates the relative diffuse reflectance for an infinite layer thickness $R_\infty(\lambda)$, to the wavelength dependent macroscopic absorption cross-section, $\mu_a(\lambda)$, and modified macroscopic scattering cross-section, $\mu_{st}(\lambda)$, of the reflecting layer, and/or the cell suspension:

$$\frac{(1 - R_\infty(\lambda))^2}{R_\infty(\lambda)} = \frac{\mu_a(\lambda)}{\mu_{st}(\lambda)} \quad (3)$$

See Mignani et al., Kortum, and Pisharoty, supra. It should be noted that the term "modified macroscopic scattering cross-section" is also sometime referred to as "reduced macroscopic scattering cross-section." As such, these terms may be used interchangeably throughout this application. Both the macroscopic absorption and modified scattering cross-sections are functions of the size, composition, and concentration of the scattering elements, primarily the red blood cells (see Eqs. 10-12 below). Under the conditions of weak absorption and constant scattering (i.e., when the macroscopic scattering cross section $\mu_s(\lambda)$ is equal to a constant, S), only the macroscopic absorption cross-section is a function of the hemoglobin concentration and the hemoglobin composition. Under these conditions, the macroscopic absorption coefficient may be represented by:

$$\mu_a(\lambda) = N_p \sum_{j=1}^{N} x_j \alpha_j(\lambda) \quad (4)$$

Where, $\alpha(\lambda)$ has the same meaning as in Equation (1), $N_p$ is the number of red blood cells per volume of suspension, and $x_j$ is the volume fraction of $j^{th}$ form of hemoglobin. Substituting Equation (4) into Equation (3) and collecting the terms produces:

$$F_R(\lambda) = \frac{(1 - R_\infty(\lambda))^2}{R_\infty(\lambda)} = K \sum_{j=1}^{N} x_j \alpha_j \quad (5)$$

Where, $F_R(\lambda)$ is the Reflectance Function, and $K = N_p/S$. See Mignani et al., supra. Notice that the function, $F_R(\lambda)$, in Equation 5 is linear with respect to the composition of hemoglobin; hence, the composition estimates can be obtained using the least squares solution given in Equation (2).

2. Non-Linear Interpretation Models

Non-linear interpretation models are suitable when the measurement configuration is such that scattering due to the presence of red blood cells contributes significantly to the features of the measured spectra.

i. Transmission Models: The non-linear interpretation model for transmission that includes the effects of the size and composition of the red blood cells is given by:

$$\tau(\lambda) = N_p l \left(\frac{\pi}{4}\right) \int_0^\infty Q_{ext}(m(\lambda), D) D^2 f(D) dD \quad (6)$$

Where, l is the pathlength, D represents the characteristic dimension of the particle, $Q_{ext}$ is to the extinction efficiency, and $N_p$ is the number of red blood cells per unit volume. The total extinction efficiency, $Q_{ext}(m(\lambda),D)$ is a function of the optical properties of the particles and suspending medium, through the complex refractive index, $m(\lambda)$:

$$m(\lambda) = \frac{n(\lambda) + i\kappa(\lambda)}{n_0(\lambda)} \quad (7)$$

Where, $n(\lambda)$ and $\kappa(\lambda)$ represent the real and imaginary components of the complex refractive index of the red blood cells, respectively, and $n_o(\lambda)$ represents the real refractive index of the suspending medium.

The real and imaginary parts of the complex refractive index are functions of the chemical composition and can be calculated as a weighted sum of the contributions from the chromophores within each population of scattering elements. See Alupoaei et al., *Chemical Engineering Communications* 192: 198-218 (2005):

$$n = \sum_{j=1}^{N} \omega_j n_j \quad (8)$$

$$\kappa = \sum_{j=1}^{N} \omega_j \kappa_j \quad (9)$$

Where, $\omega_j$ represents the mass fraction of $j^{th}$ form of hemoglobin and N represents the total number of chromophores under consideration (for example, the number of hemoglobin forms). It is important to note that the additivity of the optical properties applies only as part of the scattering calculations. Adding the scattering contributions represented by Eqs. (6)-(9) completes the total mass balance for the hemoglobin form under consideration.

ii. Reflectance Models: The Kubelka-Munk model describing the relative diffuse reflectance for an infinite layer thickness (Equation 3) includes the effects of the particle size and composition of the particles (i.e. red blood cells) through the wavelength dependent macroscopic absorption and scattering cross-sections, $\mu_a(\lambda)$ and $\mu_s(\lambda)$, respectively. The macroscopic absorption cross-section, $\mu_a(\lambda)$, and scattering cross-section, $\mu_s(\lambda)$, describe the combined optical properties of multiple scatters and chromophores present in a given sample. The macroscopic absorption cross-section may be calculated as:

$$\mu_a(\lambda) = \sum_{J=1}^{N} N_{pJ} C_{absJ} + \sum_{i=1}^{M} \frac{4\pi\kappa_i(\lambda)}{\lambda} [C_i] \quad (10)$$

Where, the first term on the right hand side of Equation (10) includes the product of single-particle absorption cross-sections, $C_{abs}$, and particle concentrations $N_p$, summed over N populations of particles, and the second term incorporates the absorption contributions from M chromophoric compounds with concentrations, $C_i$, that are dissolved in the media of the sample.

Equations (11a) and (11b) represent two different approximations for the total macroscopic scattering cross-section, $\mu_s(\lambda)$, as a function of single-particle scattering cross-sections $C_{sca}$, particle concentration, $N_p$, and the average volume, $V_p$, of the $J^{th}$ particle population, over N populations of particles:

$$\mu_s(\lambda) = \sum_{J=1}^{N} \mu_{sJ} = \sum_{J=1}^{N} N_{pJ}(1 - N_{pJ}V_{pJ})C_{scaJ} \quad (11a)$$

$$\mu_s(\lambda) = \sum_{J=1}^{N} N_{pJ}\left(1 - \sum_{z=1}^{N} N_{pz}V_{pz}\right)C_{scaJ} \quad (11b)$$

In both approximations represented by Eqs. (11a) and (11b), the multi-scattering approximation includes the effects of one or more particle populations. The first approximation in Equation (11a) computes the total macroscopic scattering cross-section as a sum of macroscopic cross-sections calculated for each individual particle population. The second approximation in Equation (11b) computes the total macroscopic scattering cross-section as a sum of macroscopic cross-sections that are calculated for each individual particle population, which depend on concentrations and volumes of the other particle populations present.

For each of the above-noted approximations of the scattering coefficient, the reduced (or modified) macroscopic scattering cross-section, $\mu_{s'}(\lambda)$, may be represented by Equations (12a) and 12(b), respectively:

$$\mu_{s'}(\lambda) = \sum_{J=1}^{N} N_{pJ}(1 - N_{pJ}V_{pJ})C_{scaJ}(1 - \langle\mu_J\rangle) \quad (12a)$$

$$\mu_{s'}(\lambda) = \sum_{J=1}^{N} N_{pJ}\left(1 - \sum_{z=1}^{N} N_{pz}V_{pz}\right)C_{scaJ}(1 - \langle\mu_J\rangle) \quad (12b)$$

In Eqs. (12a) and (12b), the scattering coefficient, $\mu_s(\lambda)$, is corrected to account for anisotropy of the scattering, $\langle\mu\rangle$, also known as the asymmetry parameter. The single-particle cross-sections, $C_{abs}$ and $C_{sca}$, may be calculated by methods that are described, for example, according to Sharaf, M. A., et al., CHEMOMETRICS (Wiley-IEEE, 1986), and van de Hulst, H. C., LIGHT SCATTERING BY SMALL PARTICLES (Wiley, 1957). The effect of the hemoglobin composition comes through the complex refractive index that are described in Eqs. (8)-(9). The absorption and scattering cross-sections can then be calculated using an appropriate scattering theory, such as Mie, Rayleigh-Debye-Gans, and the like, depending on the type of information that is to be extracted from the sample. See Sharaf et al. and van de Hulst, supra; Kerker, THE SCATTERING OF LIGHT AND OTHER ELECTROMAGNETIC RADIATION (1969); Wiscombe, *Applied Optics* 19: 1505-09 (1980).

The parameters to be estimated are the number of particles, the size distribution, and the weight fraction corresponding to each of the chromophoric groups. As in the case of transmission measurements, these parameters can be estimated from the measured spectra using standard non-linear estimation algorithms. See Lawson et al. and Jansson et al., supra.

iii. Photon Diffusion Approximation Models: The Photon Diffusion Approximation Models are the result of simplifying assumptions to the Radiative Transfer Equation. See Mignani et al. and Reynolds et al., supra. These models have been applied successfully to a wide range of physical phenomena, including the propagation of radiant energy in stellar atmospheres and the scattering of neutrons in nuclear reactors. Id. See also Chandrasekhar, Radiative Transfer (1950); Case et al., Linear Transport Theory (1967). Furthermore, essentially all previous studies of light propagation in blood, where polarization effects are not important, have been adequately described by them. See Cheung et al., Reynolds et al. (1975), and Reynolds et al. (1976). supra; Bell, G. I., and S. Glasstone, Nuclear Reactor Theory (Van Nostrand Reinhold Co., 1970); Ishimaru, A., Wave Propagation and Scattering in Random Media (1997).

The above-cited literature reports an effective solution to the photon diffusion problem in blood, stated in terms of the diffuse reflectance (i.e., the backscattered intensity, normalized to the incident flux) for an arbitrary detector aperture, $r_x$. That solution can be expressed by:

$$R_x(r_x) = \frac{2\mu_{sr}(\lambda)}{a^2} \tag{13}$$

$$\sum_{n=1}^{\infty} \frac{k_n z_n \cos \gamma_n}{N_n \zeta_n^2 (k_n + \mu_t(\lambda))} \begin{cases} \left(\frac{a^2}{2}\right) - r_x a I_1(\zeta_n a) K_1(\zeta_n r_x); & r > r_x \\ \left(\frac{r_x^2}{2}\right) - r_x a K_1(\zeta_n a) I_1(\zeta_n r_x); & r < r_x \end{cases}$$

$$D_f = \frac{1}{3}[\mu_{sr}(\lambda) + \mu_a(\lambda)]^{-1} \tag{14}$$

$$\mu_t(\lambda) = \mu_s(\lambda) + \mu_a(\lambda) \tag{15}$$

$$k_n z_0 = -2.142 D_f k_n \tag{16}$$

$$\zeta_n^2 = k_n^2 + \mu_a(\lambda)/D_f \tag{17}$$

$$\gamma_n = \arctan(2.142 D_f k_n) \tag{18}$$

$$N_n = \int_0^{z_0} \sin^2(k_n z + \gamma_n) dz \tag{19}$$

$$z_n = k_n \cos \gamma_n + \tag{20}$$
$$\mu_t(\lambda) \sin \gamma_n - [k_n \cos(k_n z_0 + \gamma_n) + \mu_t(\lambda) \sin(k_n z_0 + \gamma_n)] e^{-\mu_t(\lambda) z_0}$$

Where, $D_f$ is the modified photon diffusion constant, $I_l$ and $K_l$ denote the first-order modified Bessel functions of the first and second kind, respectively, a is the radius of the light source, $k_n$ is the $n^{th}$ eigenvalue of the Green's Function, z is the depth, and $\mu_t(\lambda)$ is the total absorption and scattering cross section. See Chandrasekhar, Case et al., Bell et al, and Ishimaru et al., supra; Johnson, *IEEE Trans. Biomed. Eng.* 17: 129-33 (1970).

The diffusely reflected (backscattered) intensity, $R_d(\lambda)$, incident on a detector with aperture radius b, separated from the source by the distance $r_b$, can be calculated from the following equation:

$$R_d(\lambda) = \frac{b^2}{r_2^2 - r_1^2}(R_x(r_2) - R_x(r_1)) \tag{21}$$

Where, $r_1 = r_b - b$ and $r_2 = r_b + b$. Similarly, by considering the net flux of photons across the depth of the sample, the diffuse transmittance corresponding to the diffusion approximation and can be expressed as $$T_z(\lambda) = \sum_{n=1}^{\infty} \left[\frac{\cos(k_n d + \gamma_n)}{\cos \gamma_n}\right] R_{dn} + e^{-\mu_t z} \tag{22}$$

Where, d is the depth of the sample, z the depth at which the transmitted light is observed and $R_{dn}$ corresponds to the $n^{th}$ term of the reflectance series that is provided in Equation (13).

The inventors have implemented Equations 12-22, together with the definition of the scattering, absorption, and transport cross sections (collectively Equations 10-12, and 14) to constitute a fundamental interpretation model that can be used effectively to analyze transmittance and reflectance spectra. Furthermore, this interpretation model can be readily expanded to include different boundary conditions, collimated transmittance, and reflectance terms, as well as the effect of layered boundaries such as glass, plastic, and other membranes. See Cheung et al. and Mignani et al., supra. Exemplary parameters that can be obtained from these models, comprise:

Probe geometry, pertaining to apertures for the source(s) and the detector(s), and distances between them.

Physical characteristics of the sample, including but not limited to, the concentration, size, and composition of the scattering elements and the chromophoric groups such as hemoglobin and nucleotides, and particulates such as red blood cells, white blood cells, platelets, and pathogens.

The principle of the present invention is further illustrated by reference to two sets of experiments, described in detail below: (1) theoretical simulations of the expected changes in the spectral features as functions of changes in the composition of blood sample; and (2) blood culturing experiments, where the resultant spectral data over time are deconvolved with theoretical simulations, and the subsequent deconvolution results are applied to determine the presence of microorganisms.

E. Theoretical Simulations

1. General Assumptions

Transmittance and reflectance data are generated under the following assumptions:

First, it is assumed that the three most prevalent forms of hemoglobin are oxy-, deoxy-, and methemoglobin, and that the overall mechanisms to describe the changes in the cell population are given by the appropriate combination of the following exemplary equations:

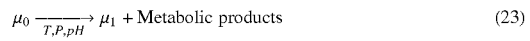
$$\mu_0 \xrightarrow{T,P,pH} \mu_1 + \text{Metabolic products} \tag{23}$$

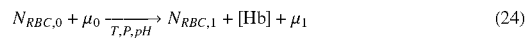
$$N_{RBC,0} + \mu_0 \xrightarrow{T,P,pH} N_{RBC,1} + [\text{Hb}] + \mu_1 \tag{24}$$

Where, $\mu_0$ and $\mu_1$ represent the changes in concentration of the microorganisms, $N_{RBC,0}$ and $N_{RBC,1}$ represent the change in the concentration of red blood cells, and [Hb] represents the concentration of free hemoglobin in solution (due to hemolysis). The changes in the hemoglobin composition may be described by:

$$\text{HbO}_2 + \mu_0 \xrightarrow{T,P,pH} \text{Hb} + \mu_1 \tag{25}$$

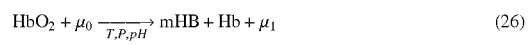
$$\text{HbO}_2 + \mu_0 \xrightarrow{T,P,pH} \text{mHB} + \text{Hb} + \mu_1 \tag{26}$$

$$\text{Hb} + \text{O}_2 \xrightarrow{T,P,pH} \text{mHb} \tag{27}$$

Where, $\text{HbO}_2$, and Hb, and mHb represent oxy-, deoxy-, and met-hemoglobin, respectively. These calculations can be performed using other forms of hemoglobin, including but not limited to carboxy- and sulf-hemoglobin.

Equations 23-26 describe the effects of metabolic activity of microorganisms under aerobic conditions. Equations 23-24 are applicable to anaerobic conditions.

Under a second assumption, during an initial equilibration time period, the hemoglobin is either oxygenated or deoxygenated, depending upon the composition of the headspace and the media in the sample container. See Priezzheve et al., Shrot et al. and Repaske et al., supra.

In the absence of microorganisms, hemoglobin composition slowly changes from oxy- to methemoglobin (see, Equation 27). This process may be considered to be insignificant for the purposes of analysis of blood cultures for microbial contamination.

Finally, it is assumed that the media is buffered to prevent significant changes in pH.

2. Theoretical Transmission Spectra

The simulated transmission spectra incorporate both the sample properties and the configuration of the measurement device. The sample parameters include, but are not limited to, the volume of red blood cells, the volume fraction of red blood cells in the culture media, and the fraction of hemoglobin in red blood cells. An exemplary measurement device may considered to be a polished fiber terminus without lenses.

Figure 3:
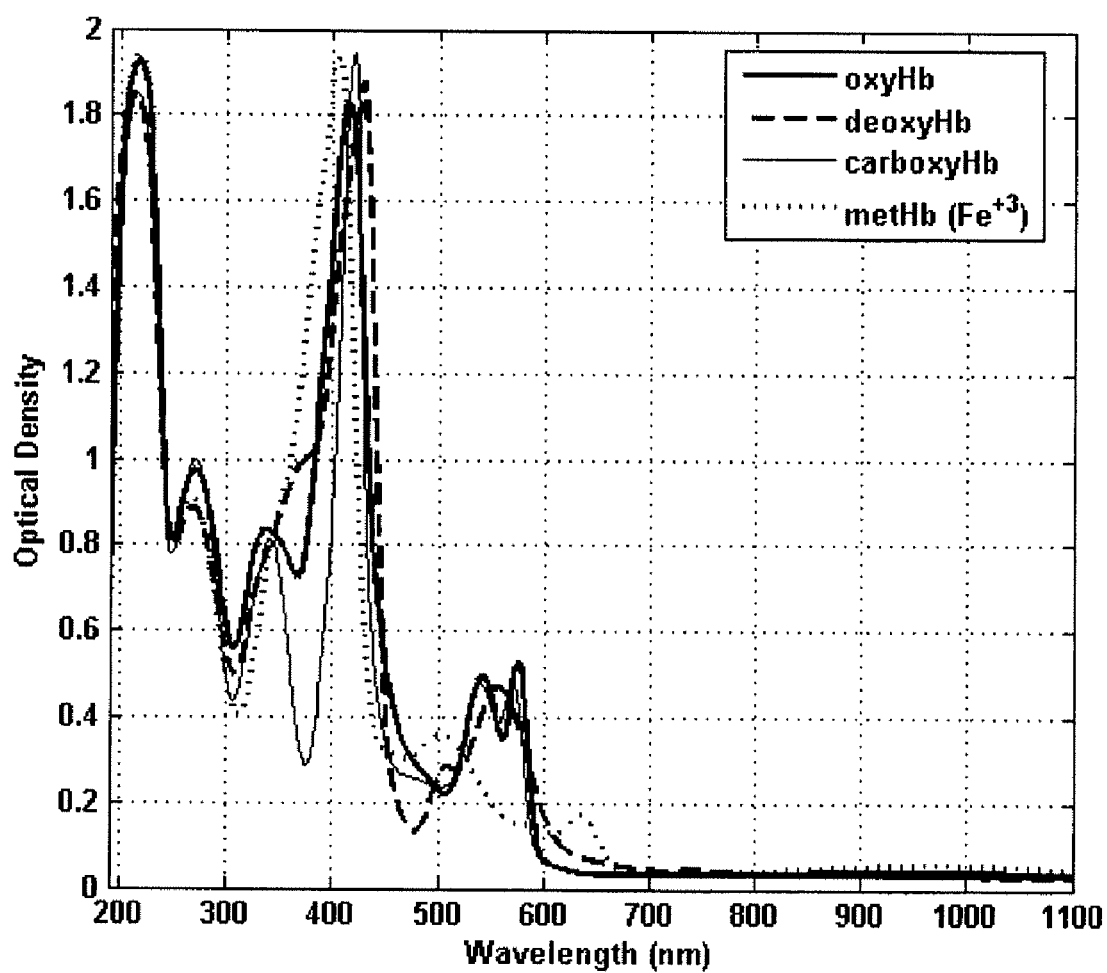
FIG. 3 shows a transmittance spectra associated different forms of hemoglobin.

FIG. 3 shows the theoretical diffuse transmittance spectra calculated through the use of Eqs. (6) to (9), together with the optical properties of hemoglobin that are illustrated in FIG. 1. Each line in FIG. 3 represents one of four common forms of hemoglobin: oxy-, deoxy-, carboxy-, and met-hemoglobin, using red cell volume (Vp) of 90 µm³, volume fraction of red blood cells in the sample ($N/V_p$) of 0.084, and volume fraction of hemoglobin in the red blood cells of 0.33. Notable are the spectral differences between oxyhemoglobin, deoxyhemoglobin, methemoglobin, and carboxyhemoglobin. The characteristics of heme moiety are readily apparent in the absorption bands around 400 nm (Soret band) and in the region between 500-600 nm.

Figure 4:
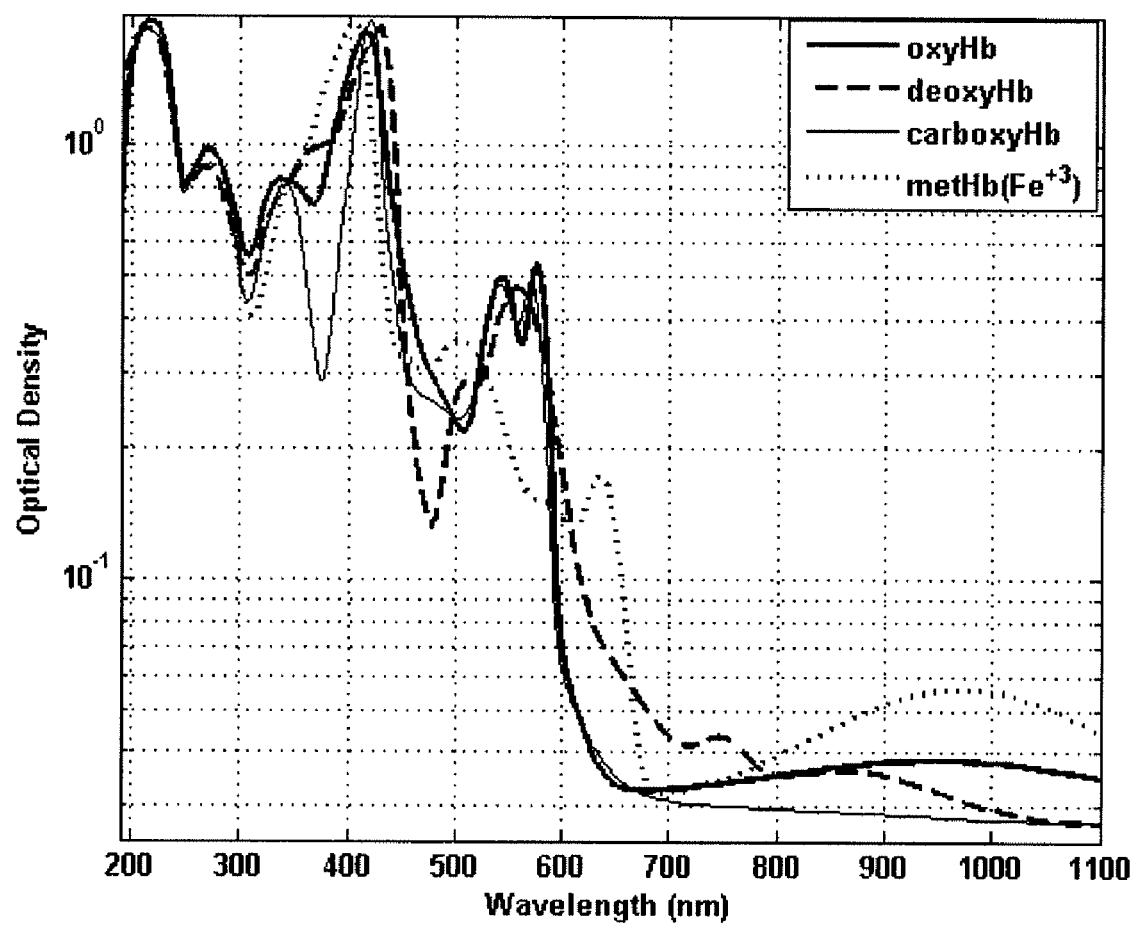
FIG. 4 provides a logarithmic representation of the transmittance spectra shown in FIG. 3.

FIG. 4 presents a logarithmic representation of the data from FIG. 3. The logarithmic transformation enhances the differences between the absorption bands in the Vis-NIR portion of the spectrum. Comparison of FIGS. 4 and 1 shows that, even when the scattering effects due to the size and concentration of the red blood cells are included (i.e., by utilizing Eqs. 6 to 9), the absorption features of the extinction spectra of hemoglobin are retained. According with the principles of the present invention, these differences can be used to estimate the relative composition of the different forms of hemoglobin.

It is evident from the theoretically calculated spectra (FIGS. 3 and 4) that the transmission measurements are sufficiently distinct to identify changes in hemoglobin due to the presence of microorganisms in a blood sample.

3. Theoretical Reflectance Spectra

For the purpose of reflectance simulations, an exemplary reflectance probe configuration may be considered that comprises emitting and receiving fibers with aperture diameters of 400 µm, each separated by a center-to-center distance of 500 µm (see, for example, the configuration that is illustrated in FIG. 2). Since the reflectance signal saturates below 500 nm, a suitable spectral window for reflectance measurements in the case of blood may be selected to fall between 500-1100 nm. This window includes the absorption bands corresponding to the electronic structure of the heme moiety (500-600 nm). It should be noted that the selection of the above-noted range of wavelengths is due to the limitations of the detector instrumentation and technology, and it does not represent an inherent limitation of the various embodiments of the present invention. It is therefore possible to readily extend this spectral measurement range if more sophisticated detections systems become available.

Figure 5:
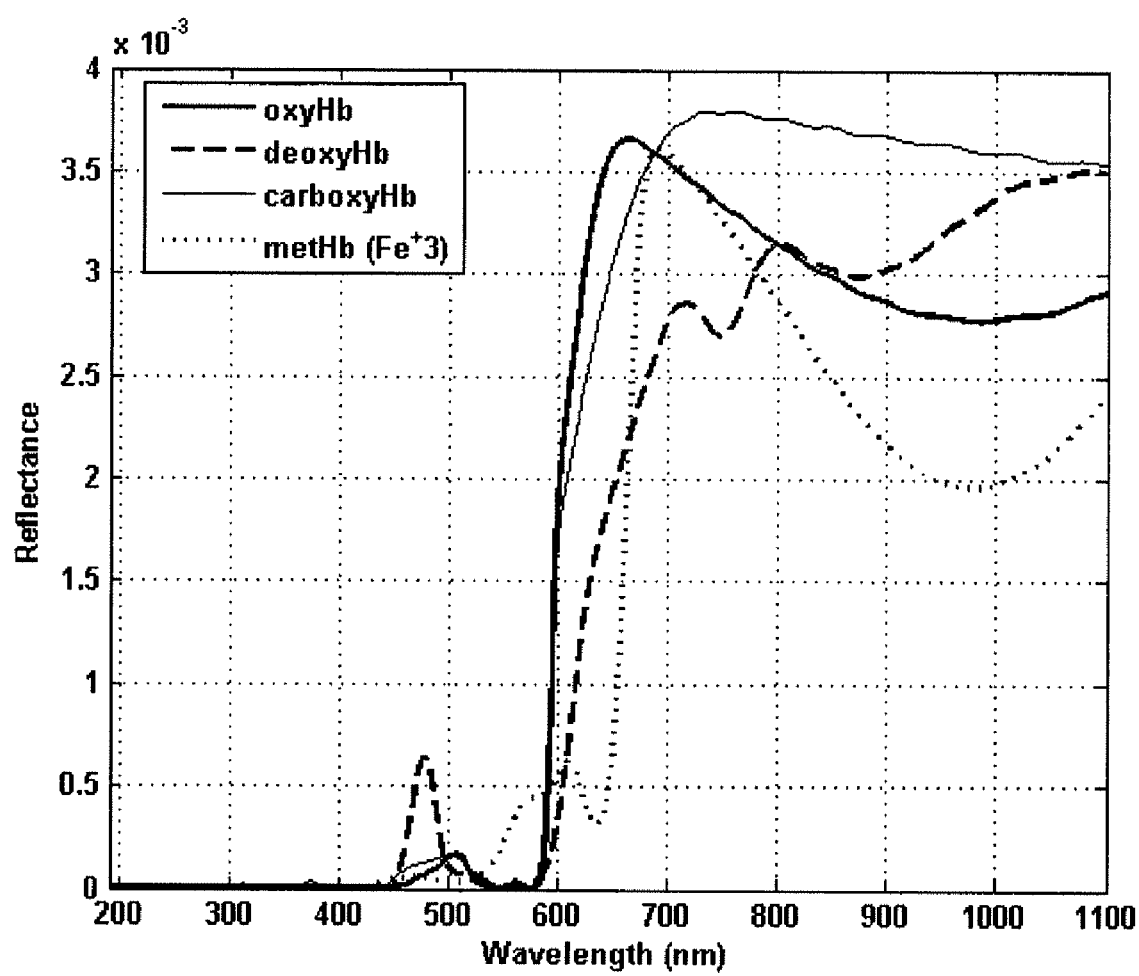
FIG. 5 illustrates a reflectance spectra associated with different forms of hemoglobin.

FIG. 5 shows exemplary theoretical diffuse reflectance spectra that are calculated using Equation 13. Notice that in FIG. 5, significant spectral differences corresponding to different forms of hemoglobin are clearly distinguishable. These differences in the reflectance spectra, as well as those associated with the transmittance spectra, can be used to estimate changes in the relative composition of hemoglobin arising from the presence of microorganisms.

The mechanisms described in Eqs (23)-(26) indicate that the rate of conversion from oxy- to deoxy-hemoglobin, and/or the particle count of the sample, is proportional to the number of organisms. Therefore, it is possible to simulate how the spectral features change as a function of the organism's growth rate.

Figure 6:
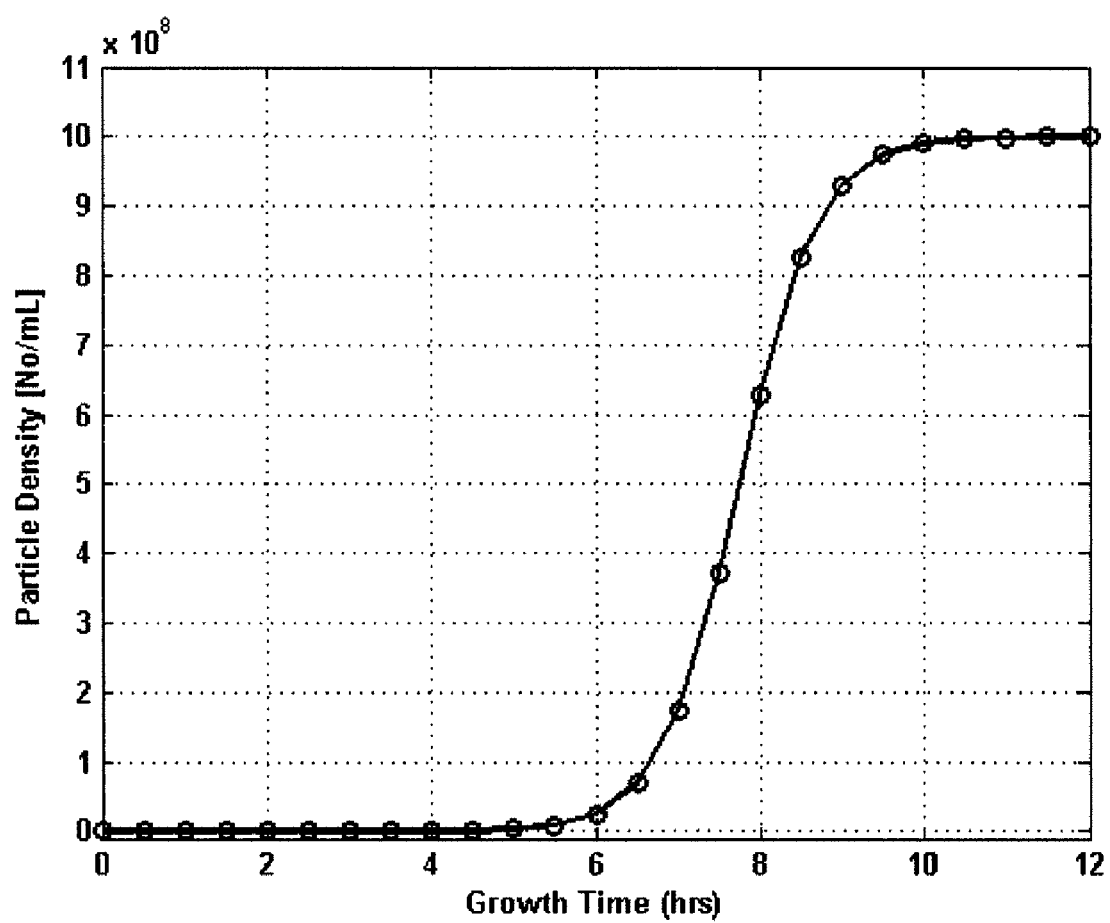
FIG. 6 presents a bacterial growth curve with a 20-minute doubling time.
Figure 7:
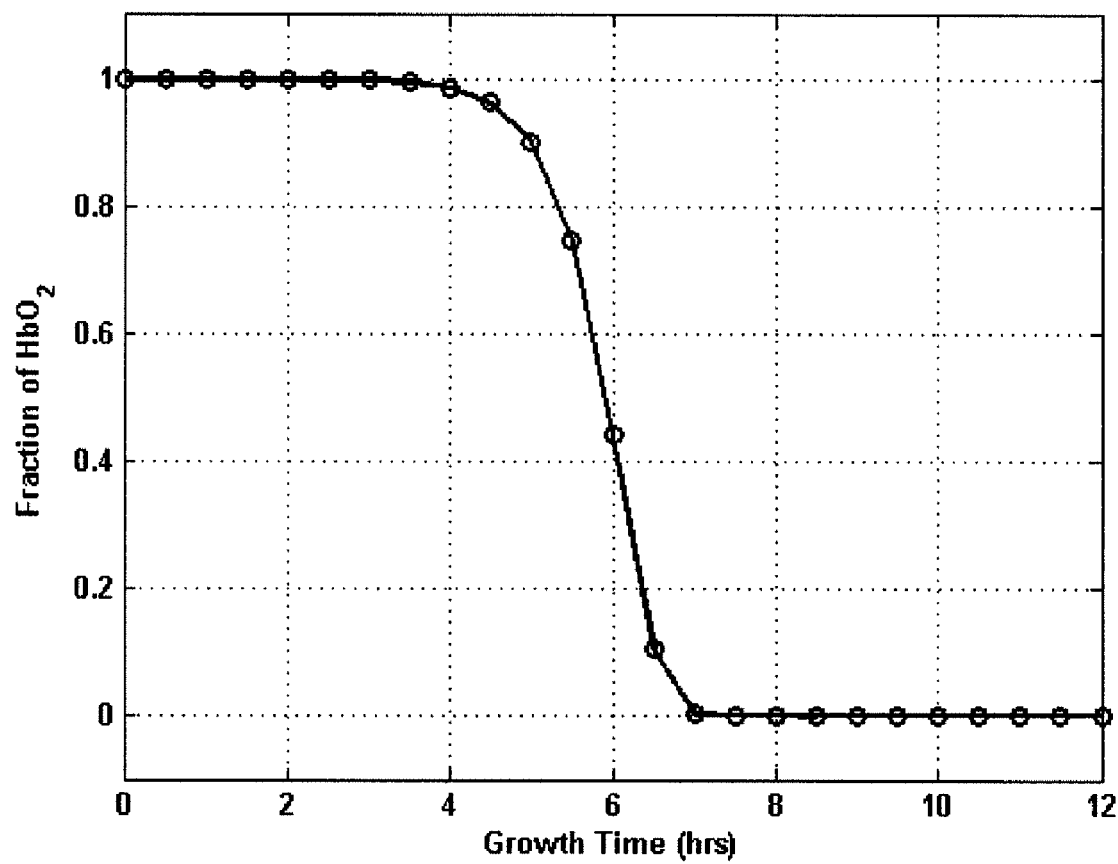
FIG. 7 illustrates oxy-hemoglobin conversion as a function of elapsed time due to the production of $CO_2$ by bacteria.
Figure 8:
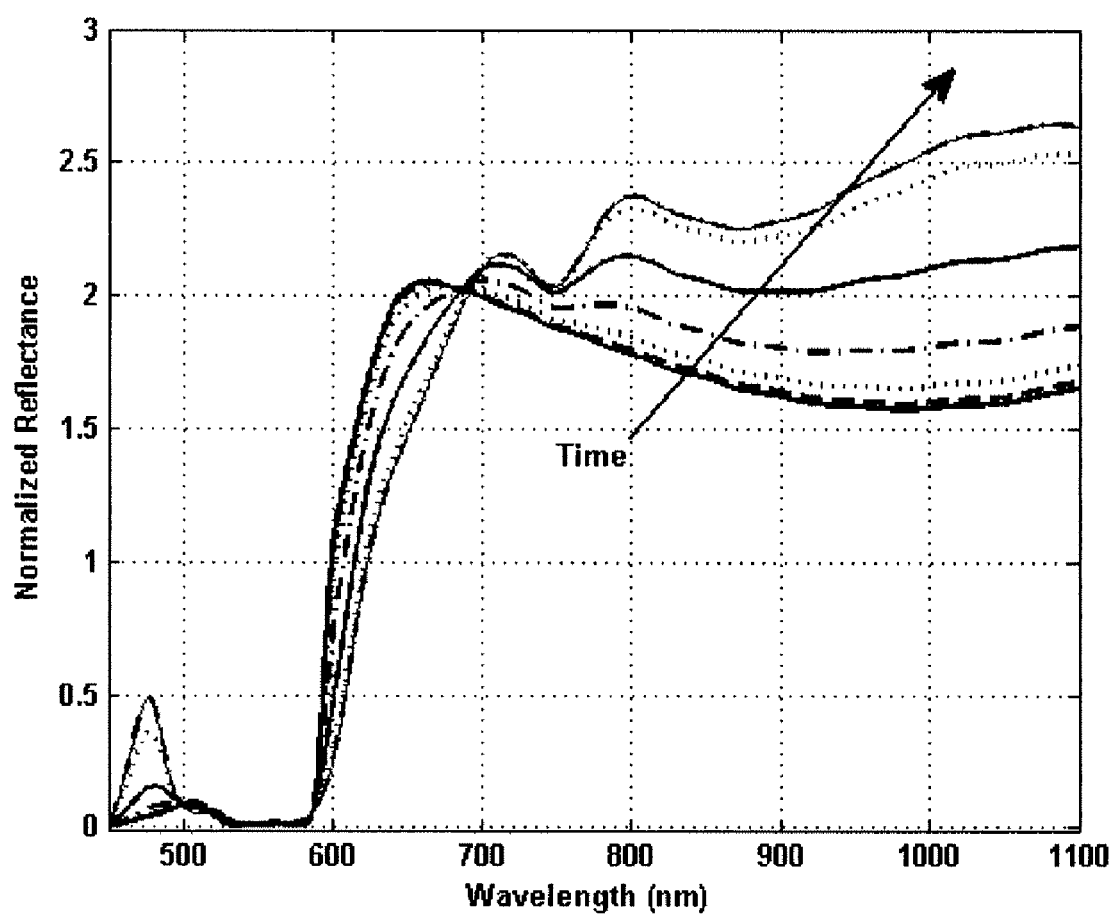
FIG. 8 shows predicted reflectance spectra of the blood sample, with microbial growth, shown in FIGS. 6 and 7.

Microbial metabolic activity changes the composition of hemoglobin in aerobic samples. A representative bacterial growth curve with a 20 minute doubling time is shown in FIG. 6. FIGS. 7 and 8 depict the transition of oxyhemoglobin to deoxyhemoglobin due to the metabolic activity of the microorganisms that are characterized in FIG. 6. The trend of transitions over time is illustrated by an arrow in FIG. 8. FIG. 7 shows oxy-hemoglobin conversion as a function of time, while FIG. 8 depicts normalized reflectance spectra. Normalization involves correcting the spectra such that the isosbestic point (~805 nm) of the hemoglobin spectra is retained. This allows for an accurate spectrum-to-spectrum comparison, and corrects for sampling and measurement-to-measurement variability.

In the simulations represented in FIGS. 7 and 8, the initial equilibration period has not been considered. For the purpose of this set of simulations, it is assumed, as initial condition, that the blood is 100% oxygenated. As such, the fraction of oxyhemoglobin changes in conjunction with the growth of the microorganism in the sample. As illustrated in FIG. 7, there is a gradual conversion of oxyhemoglobin to deoxyhemoglobin throughout the lag phase (hours 0-4) of bacterial growth. This is followed by a rapid decrease in the fraction of oxyhemoglobin when the culture reaches the exponential growth phase (hours 4-7). The fraction of oxyhemoglobin continues to decrease as the culture reaches the stationary growth phase (hours 7-12). The existence of the inflection points in the hemoglobin conversion curves is indicative of the metabolic activity of the microorganisms.

Figure 9:
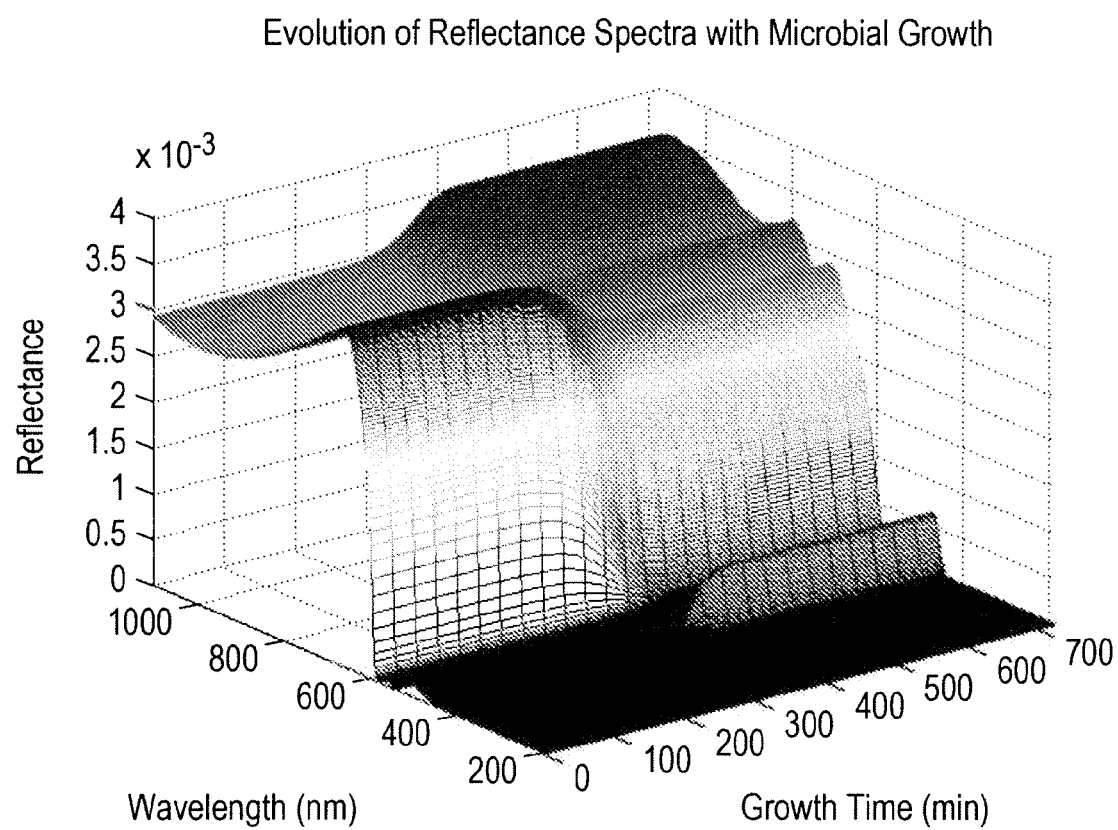
FIG. 9 illustrates simulated reflectance spectra for the complete time course of the blood sample, with microbial growth, shown in FIGS. 6 and 7.

FIG. 9 represents the simulated reflectance spectra for the complete time course of the blood sample with microbial growth that is shown in FIGS. 6 and 7. The changes in hemoglobin conversion curves can be appreciated from the calculated spectra shown in FIGS. 8 and 9. Notice that a dramatic change in the spectra occurs when the culture reaches the lag phase. This is indicative of the metabolic activity of the microorganisms; hence, a positive sample can be identified. According to the principles of the present invention, depending on the quality of the spectral measurements, the presence of microorganisms may be identified in the lag phase, thereby considerably reducing the time to detection, compared to what conventional technology achieves. Further details and examples of such enhanced detection capability will be described herein.

Figure 10:
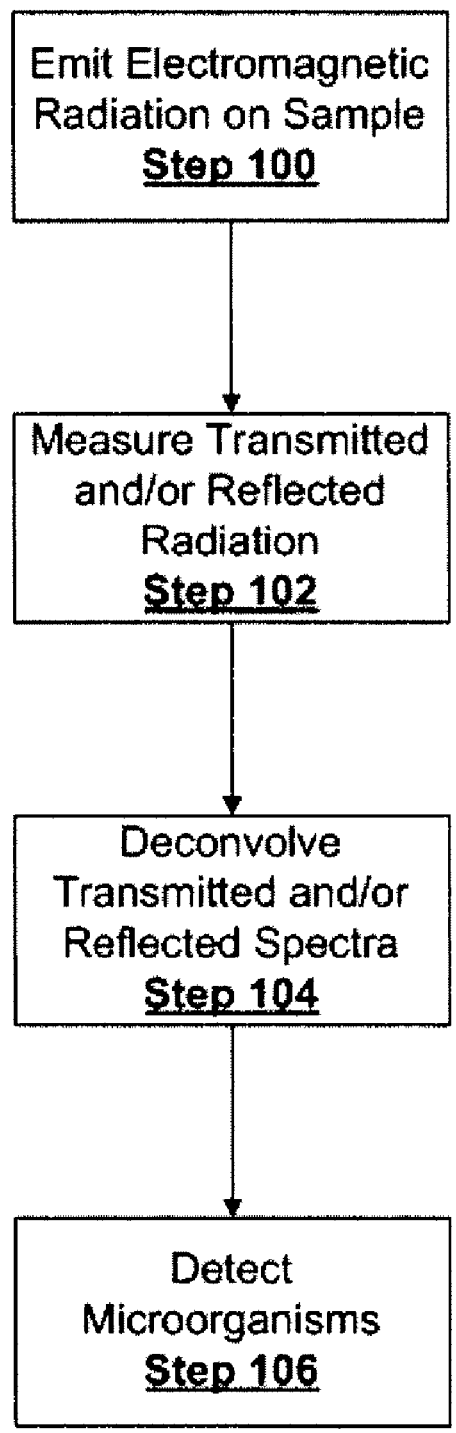
FIG. 10 is a flow diagram illustrating the various exemplary steps associated with detecting microorganisms.

The differences predicted by the theoretical transmittance and reflectance spectra clearly indicate that the changes in the composition of hemoglobin caused by the metabolic activity of organisms in blood can be readily measured via multiwavelength spectroscopic techniques in the UV-Vis-NIR portion of the electromagnetic spectrum. FIG. 10 provides a flow diagram describing the sequence of exemplary steps involved in the detection of microorganisms in a blood sample in accordance with the principles of the present invention. In Step 100, one or more blood samples are irradiated with electromagnetic radiation. This step may be carried out, for example, by illuminating the sample with a wide spectrum light source that is operable in the UV-Vis-NIR range. In Step 102, the reflected and/or transmitted radiation is measured. Step 102 may be carried out for example, using a commercially available spectrometer. In Step 104, the detected spectra are deconvolved. Deconvolution, for example, may provide spectral characteristics related to individual forms of an indicator, such as hemoglobin, within, or in contact with, the blood sample. In Step 106, the deconvolution results obtained from Step 104 are analyzed to detect microorganisms. The detection of microorganisms may involve, for example, the detection of type, rate of growth, absence, presence and/or other characteristics associated with the microorganisms.

F. Vapor-Liquid Equilibrium Model

Blood culturing systems available today are based on creating optimal conditions for microbial growth under aerobic and anaerobic environments coupled with the detection of microbial metabolic products and gases resulting from the growth of microorganisms in a thermodynamically closed system. Such a thermodynamically closed system can be defined by a known mass balance that is either physically constrained (e.g., as in a sealed container) or chemically constrained (e.g., as in the case of an open container with an inert gas acting as a barrier to the environment that is external to the reactions of consequence).

In general, blood culture systems are closed physically, and so metabolic products from contaminating microorganisms accumulate in the vial and distribute between the vapor phase (head space), the liquid phase (e.g., culture media and plasma), and the solid phase (e.g., immobilized indicator, particulates) that are present. The particulates in this case are primarily the red blood cells (RBC's), although initially there also may exist white blood cells, platelets, and microorganisms, which are capable of respiration. As time passes, the number of contaminant organisms increases, resulting in increased concentrations of their metabolic products, which interact with different blood components.

A vapor-liquid equilibrium model, characterizing the state of vapor and liquid constituents of such thermodynamically closed systems, can be used to evaluate pH, total pressure and partial pressures of gasses such as oxygen and carbon dioxide. These parameters are important indicators of the constituency of blood samples. For example, since the various forms of hemoglobin are tied to the availability of oxygen and carbon dioxide, understanding the partial pressure and/or concentrations of these gases can provide an added dimension on detecting the presence or absence of a microorganism in a blood sample.

Similar to the previously described principles related to deconvolution techniques that are applied to the reflectance spectra of hemoglobin, the reflectance spectrum can be coupled with a theoretically-based model to calculate the state of the vapor-liquid equilibrium of a blood culture bottle. In one scenario, a vapor-liquid equilibrium model can be developed and evaluated independently from the reflectance spectrum and used, in combination with optical measurements, to conduct deconvolution to assess the presence or absence of microorganisms.

These techniques may further allow for the identification of particular microorganisms that are present in the blood sample. On the other hand, if only optical measurements are available then partial gas pressures may be obtained from estimates of the composition in the liquid phase obtained from the reflectance measurements. Moreover, the deconvolution techniques that are used in conjunction with a vapor-liquid equilibrium model can be paired with yet additional physical, chemical and metabolic measurements obtained from the same sample to determine the presence or absence of one or more microorganism.

Qualitative Description

The following provides an exemplary sequence of events associated with the introduction of a blood sample into a blood culture vial. At time $t=0^-$, prior to inoculation with a blood sample, the blood culture vial with sterile nutrient broth is assumed to be in equilibrium; that is, the composition of the head space is in thermodynamic equilibrium with the liquid phase at room temperature and pressure. At time $t=0^+$, all of the blood sample has been introduced into the vial, initiating an adjustment of physical and chemical parameters of blood to the physical and chemical environment of the vial (e.g., temperature, osmolarity, composition, pH, and other parameters). Examples of physical adjustments include changes in shape, volume (swelling, contraction), and number density (hemolysis) of erythrocytes and other blood components. Simultaneously, chemical changes in the chemical composition also occur in the $O_2$—$CO_2$ state of the vial, which in turn dictates the chemical forms of the hemoglobin.

As time elapses, the number density of microorganisms increases over the incubation period of the blood culture. The microbial metabolic respiratory activity produces changes in the chemical composition in the blood culture vial, e.g. a reduction in the partial pressure of $O_2$ and a corresponding increase the partial pressure of $CO_2$. These chemical changes drive the hemoglobin equilibrium from oxy-hemoglobin ($HbO_2$) toward deoxy-(Hb) and carbamino-hemoglobin ($HbCO_2$). In the absence of microorganisms, the red blood cells will age slowly, eventually lysing, and the hemoglobin present in the sample converts to met-hemoglobin (metHb) over a few days. If hemolysis occurs as a result of the fragility of the red blood cells, and/or as a result of the production of hemolysins by certain bacteria (e.g., *Clostridium perfringens*), two effects may be observed: a decrease in the red blood cell density, and an increase in the concentration of free hemoglobin in the liquid phase. It is noteworthy that the physical and chemical changes occurring in blood as a result of the presence of microorganisms, as well as the growth behavior of microorganisms, can be quantitatively measured using spectrophotometric methods, as described in the previous sections.

Like most bio-reactors, blood culturing systems are rather complex. To facilitate the understanding of the principles of the present invention, a series of assumptions and approximations may be made:

- The bio-reactor are well-mixed, each phase being homogeneous, and to operate under isothermal conditions.
- Nutrients are in excess such that their concentration can be assumed to remain constant.
- The buffering capacity of the growth media enables the pH to remain approximately constant.
- Only three forms of hemoglobin are analyzed: oxy-, deoxy-, and carbamino-hemoglobin.
- The initial equilibration between blood and the environment of blood culture is assumed to occur instantaneously at $t=0$.
- The reactivity of hemoglobin to microbial metabolic products is greater than the time step of the model.
- Hemoglobin composition is always in chemical equilibrium with the state of the blood culture vessel.
- Of all the possible impacts on hemoglobin composition due to metabolic activity, only the transitions amongst oxy-, deoxy-, and carbamino-hemoglobin are considered.

The consumption of one mole of $O_2$ in respiration produces one mole of $CO_2$.

Under the above assumptions, a general mathematical description of the processes occurring within aerobic blood culture vials may be developed to enable a quantitative evaluation of the cultures.

Quantitative Description

Physical Changes:

The physical dimensions of blood components, primarily the erythrocyte population, have an effect on the optical measurements of blood. An example of the physical changes to the erythrocytes can be expressed by the following equation:

$$V_{rbc}(t) = V_{rbc,0} + (1 - e^{k_{sw}t})\Delta_0 \quad (28)$$

Where, $V_{rbc}(t)$ is the red blood cell volume as a function of time, $V_{rbc,0}$ is the initial or physiological red cell volume, $\Delta_0$ is the maximum volume increase, and $k_{sw}$ is the swelling rate constant in $[\text{min}^{-1}]$. Both, $\Delta_0$ and $k_{sw}$ are functions of the particular blood sample, temperature, osmolarity, composition, and pH of the growth media. Swelling implies that fluid is being drawn into red blood cells causing the mean corpuscular hemoglobin to decrease. The volume fraction of hemoglobin, $f_{HB}$, in the erythrocytes can be estimated as:

$$f_{HB}(t) = f_{Hb,0}\left(\frac{V_{rbc,0}}{V_{rbc}(t)}\right) \quad (29)$$

Chemical Changes:

At each time step in the model, the state of cell populations and hemoglobin in the blood sample is a function of the physical and chemical environment of the blood culture vial. It is further assumed that the environmental parameters such as osmolarity, pH, and temperature of incubation remain constant throughout the experiment as set at time zero. Therefore, the only temporal changes that are considered are the changes in the chemical composition in the blood culture vial, including changes in gas composition (such as $O_2$ and $CO_2$) within the vial as a result of metabolism of blood components and microorganisms. These chemical changes further affect hemoglobin composition and their conversion between different forms. For example, the depletion of $O_2$ in the system may lead to the dissociation of oxy-hemoglobin and the production of deoxyhemoglobin and liberated $O_2$. The reaction of deoxyhemoglobin with $CO_2$ may produce carbamino-hemoglobin as shown in Equation (30). Total hemoglobin in the modeled system is the sum of three forms of hemoglobin and is assumed to be conserved, as illustrated in Equation (31). It should be noted that the reaction of hemoglobin with certain reagents and/or microbial metabolic products may lead to formation of other hemoglobin forms such as met-hemoglobin, carboxy-hemoglobin, sulf-hemoglobin, and the like. However, as noted earlier, only three forms of hemoglobin are considered in the development of the exemplary model that follows.

$$HbCO_2 \longleftrightarrow Hb \longleftrightarrow HbO_2 \quad (30)$$

$$[Hb_T] = [Hb] + [HbO_2] + [HbCO_2] \quad (31)$$

The equilibrium between Hb, $HbO_2$, and $HbCO_2$ is governed by the partial pressures of $O_2$ and $CO_2$ in the system and is assumed to occur instantaneously since the gas exchange through the erythrocyte membrane is relatively fast due to its high surface area. Under these assumption, the $HbO_2$-Hb-$HbCO_2$ equilibrium reflects the chemical composition of the blood culture vial. The dynamics of the reactions between hemoglobin, $O_2$ and $CO_2$ is well understood and there is a large body of mathematical models addressing the $O_2$—$CO_2$ exchange with blood and the main variables affecting its equilibrium [See, for example, Mendelson, 1992; Flewelling, 2000]. These models can be readily adapted for the description of the equilibration processes taking place in the blood cultures. For the simulations described herein, the model proposed by Dash and Bassingthwaighte [2004; 2006] is used for the equilibrium binding of $O_2$ and $CO_2$ with hemoglobin inside red blood cells. This model has the advantage of including the effects of the gas composition as well as the effects of temperature, pH, and osmolarity.

Cell Respiration:

In addition to hemoglobin, the gas composition of a blood culture system is affected by the respiration of other blood components such as leukocytes and platelets, and when contaminated, by microorganisms. Respiration rates under specific conditions have been measured and rigorous models accounting for the electron transport chain, the biomass, and the energy available from the environment have been developed [see, for example, Jin and Bethke, 2007]. Since these models are general and provide the links between substrates and metabolic products, they may be deployed in cases where the effects of metabolic products are considered. In the description that follows, $O_2$ consumption and $CO_2$ production are represented with a simple approximation that is represented by Equation (32). Specifically, Equation (32) provides that for each molecule of $O_2$ consumed, one molecules of $CO_2$ is produced. This is a reasonable assumption for substrate-rich environments, such as the ones in blood culture vials.

$$C_6H_{12}O_6 + 6O_2 \xrightarrow{\mu(t)} 6H_2O + 6CO_2 \quad (32)$$

In addition, changes in the amounts of total $O_2$ and $CO_2$ in the vials are assumed to be strictly due to respiration of the cell populations present. Equation (33) describes the general respiration structure of the model. In this equation, the total $O_2$ loss is assumed to be the sum of $O_2$ consumptions by J cell populations, represented by the product of the population number densities, $N_j$, and the assigned respiration rates, $k_{rj}$.

$$-\frac{dO_2}{dt} = \sum_{j=1}^{J} k_{rj} N_j(t) = \frac{dCO_2}{dt} \quad (33)$$

Typically, contaminating microorganisms dominate $O_2$ consumption in the blood culture vials due to their high metabolic respiration rates. Yet, in the cases of leukemia or thrombocytosis, leukocytes or platelets, respectively, may utilize most of the available $O_2$, especially during periods when microbial numbers are low.

Cell Growth:

The evolution of the number density of the $j^{th}$ cell population, $N_j(t)$, as a function of time may be approximated using a logistic growth model, as illustrated by Equation 34.

$$N_j(t) = \frac{N_{j\infty}\beta_j \exp(k_{Dj}t)}{1 + \beta_j \exp(k_{Dj}t)}; \beta_j = \frac{N_{j0}/N_{j\infty}}{1 - N_{j0}/N_{j\infty}} \quad (34)$$

The growth/decay rate constants $k_{Dj}$ and typical values of $N_{j\infty}$ and $N_{j0}$ for modeled cell populations are given in the table listing of FIG. 24. The models for cell growth and respiration enable a preliminary classification of microorganisms. The growth/decay constant, $k_{Dj}$, and the respiration rate, $k_{rj}$, vary among organisms and, depending upon how they cluster over a wide range of species, discriminate various groups of pathogens. The magnitudes of these parameters dictate the time to detection. For example, the fast-growing bacterium *E. coli* has a typical time to detection of 10 hours while the slower growing fungus *Candida albicans* has a time to detection of approximately 24 hours for an initial inoculum of $10^3$ CFU per 10 mL of blood. See, also Longzhu Cui, et al, "Cell Wall Thickening Is a Common Feature of Vancomycin Resistance in *Staphylococcus aureus*," Journal of Clinical Microbiology, January 2003, p. 5-14.

Equilibrium Considerations:

The consumption of $O_2$ and production of $CO_2$ are proportional to the number of cells, which, in turn, changes as cells grow (microorganisms) or decay (leukocytes, platelets). At each time point, $O_2$ and $CO_2$ are distributed between the gas and liquid phases of the blood culture vials and affect the chemical form of hemoglobin, as governed by Equation (30). The $CO_2$ equilibrium follows that of $O_2$. Notice that only liquid phase includes the pH-dependent dissociation of carbonic acid. Given that the rates of gas transport between vapor and liquid phases are much greater than the rates of $CO_2$ production and $O_2$ consumption, the overall equilibrium of gases may be assumed to be achieved instantaneously in the blood culture vials, as indicated by Equation 35.

$$[O_{2T}](t) = [O_{2vap}](t) + [O_{2liq}](t) + [O_{2HB}](t) \quad (35)$$

$$= [O_{2T}]_{t=0} - \sum_{j=1}^{J} k_{rj} N_j(t)$$

Further assumptions made in the model include ideal gas behavior for the vapor phase of the blood culture vials and applicability of Henry's law for the liquid phase. From these assumptions and the hemoglobin-$O_2$—$CO_2$ dynamics discussed above, the distribution of gases between the vapor phase, the liquid phase, and hemoglobin may be evaluated with standard vapor-liquid equilibrium calculations.

G. Exemplary Experimental Demonstrations

1. Materials

The microorganisms used in this study were obtained from the American Type Culture Collection (Manassas, Va.). Microbiological media was obtained from BD-BBL (Franklin Lakes, N.J.). The following experimental data were collected using aerobic and anaerobic blood culture bottles, marketed under the BacT/ALERT® mark by bioMerieux, Inc. (Hazelwood, Mo.). Any container can be used, however, that meets the criteria mentioned below in the "Methods" section. Blood samples from healthy individuals were provided by Florida Blood Services (St. Petersburg, Fla.), and complete blood counts were performed on a Cell-DYN (Abbott Park, Ill.).

Blood samples were measured using (A) a reflectance monitoring system, such as the one depicted in FIG. 2, and (B) for reference purposes, an automated microbial detection system, BacT/ALERT® 3D, which is a product of bioMerieux, Inc. The BacT/ALERT® 3D system that is used in clinical settings, detects the presence of microorganisms by the use of a color-changing disk embedded in the base of each bottle.

2. Methods

For enhanced detection of microbial activity in blood, the following conditions may observed:

Vials should be transparent in the spectral region 450-1300 nm

The absorption and scattering properties of the growth media and/or other components within the sample container may not interfere with the ability to obtain and/or analyze reflectance or the transmission measurements Spectrometers with high resolution may be utilized that are capable of collecting electromagnetic radiation with the range of 400-1300 nm.

Containers should be closed systems (no gas exchange outside containers)

3. Sample Preparation

Laboratory-grown microbial cultures were prepared using standard techniques. Two to twenty milliliters of venous blood were inoculated into blood culture containers. Microorganisms were added to the blood culture containers at a concentration of 10-100 CFU/mL blood. Replicate samples were placed into both the reflectance monitoring system (see, for example, FIG. 2) and the reference detection system.

4. Spectrophotometric Measurements

Spectroscopy measurements were conducted with an Ocean Optics Inc. (Dunedin, Fla.) USB-4000 spectrometer equipped with either a transmission cell or a reflectance probe. Reflectance measurements of the blood were conducted by placing the reflectance probe in the configuration shown in FIG. 2. The reflectance probe did not actually touch the container surface. The reflectance probes were scaled to 100% reflectance using $MgO_2$ as a reference.

5. Deconvolution of the Measured Spectra

Figure 11:
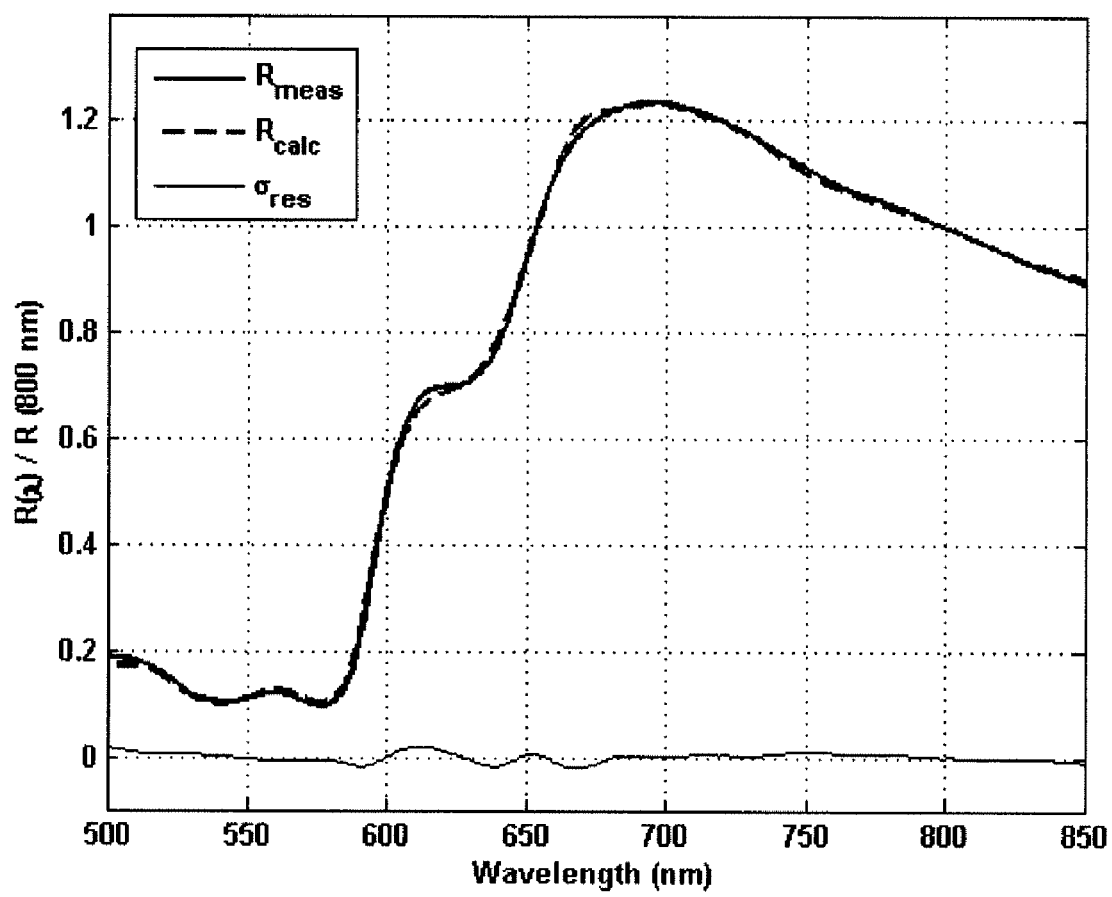
FIG. 11 illustrates a comparison between measured and calculated reflectance spectra of a blood sample in a blood culture bottle at a first time point.
Figure 12:
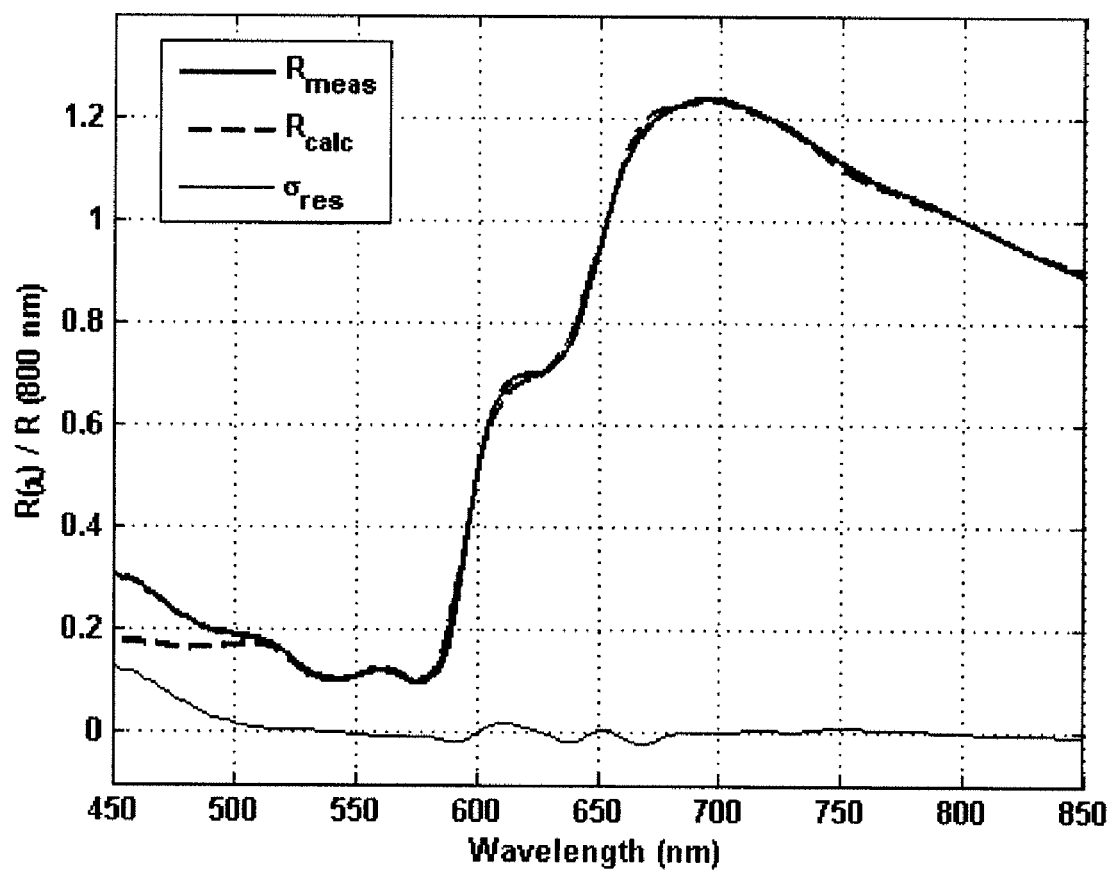
FIG. 12 depicts a comparison between measured and calculated reflectance spectra of a blood sample in a blood culture bottle at a second time point.

Deconvolution of the measured spectra includes estimating an appropriate set of adjustable parameters in the interpretation model Equations 1-35 such that the measured and calculated spectra agree within a given tolerance. FIGS. 11-12 show a comparison between measured spectra taken at two time points (t=0.25 and 119 hours) and their corresponding theoretically fitted spectra. The earlier time point (FIG. 11) represents a typical sample with a high concentration of oxyhemoglobin. The latter time point (FIG. 12) is representative of a sample with a mixture of three forms of hemoglobin, specifically, oxy-, deoxy- and met-hemoglobin.

Figure 13:
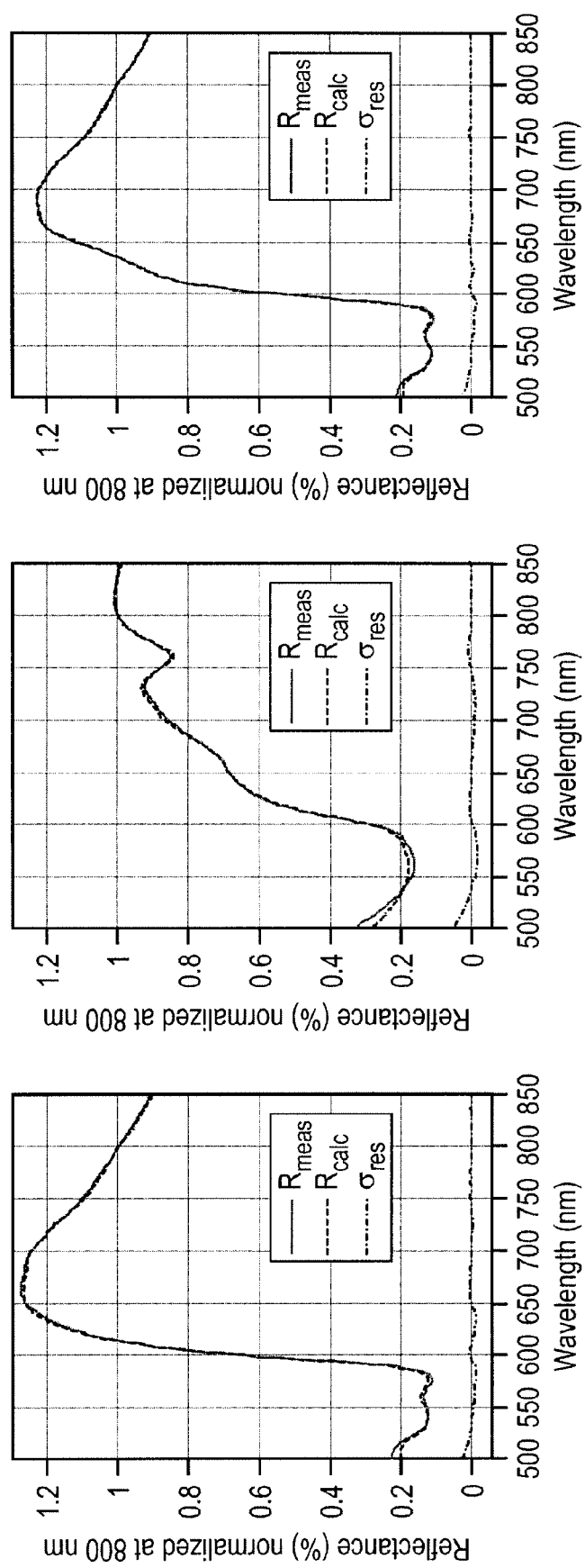
FIG. 13 presents the comparisons between measured and predicted reflectance spectra for three different blood samples.
Figure 14:
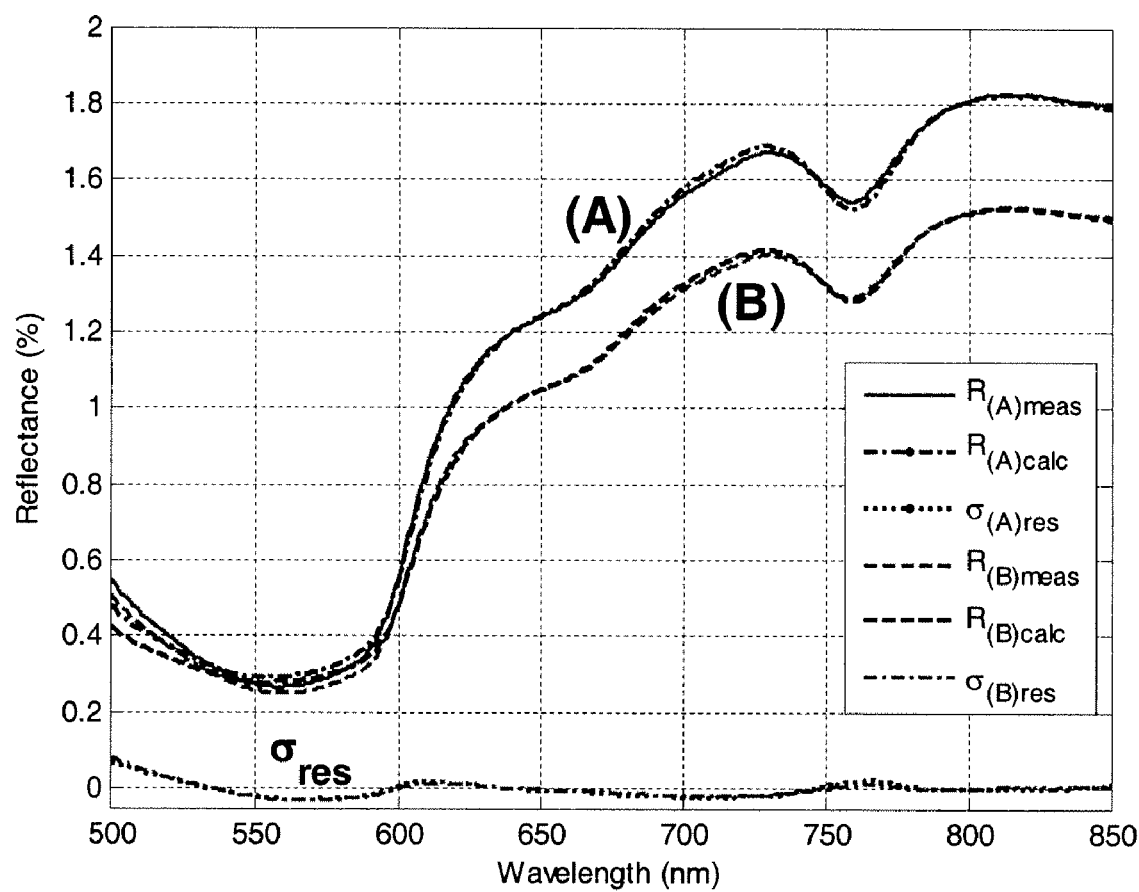
FIG. 14 illustrates the differences between the reflectance spectra associated with two different blood samples due to mean corpuscular volume of the scattering elements.
Figure 15:
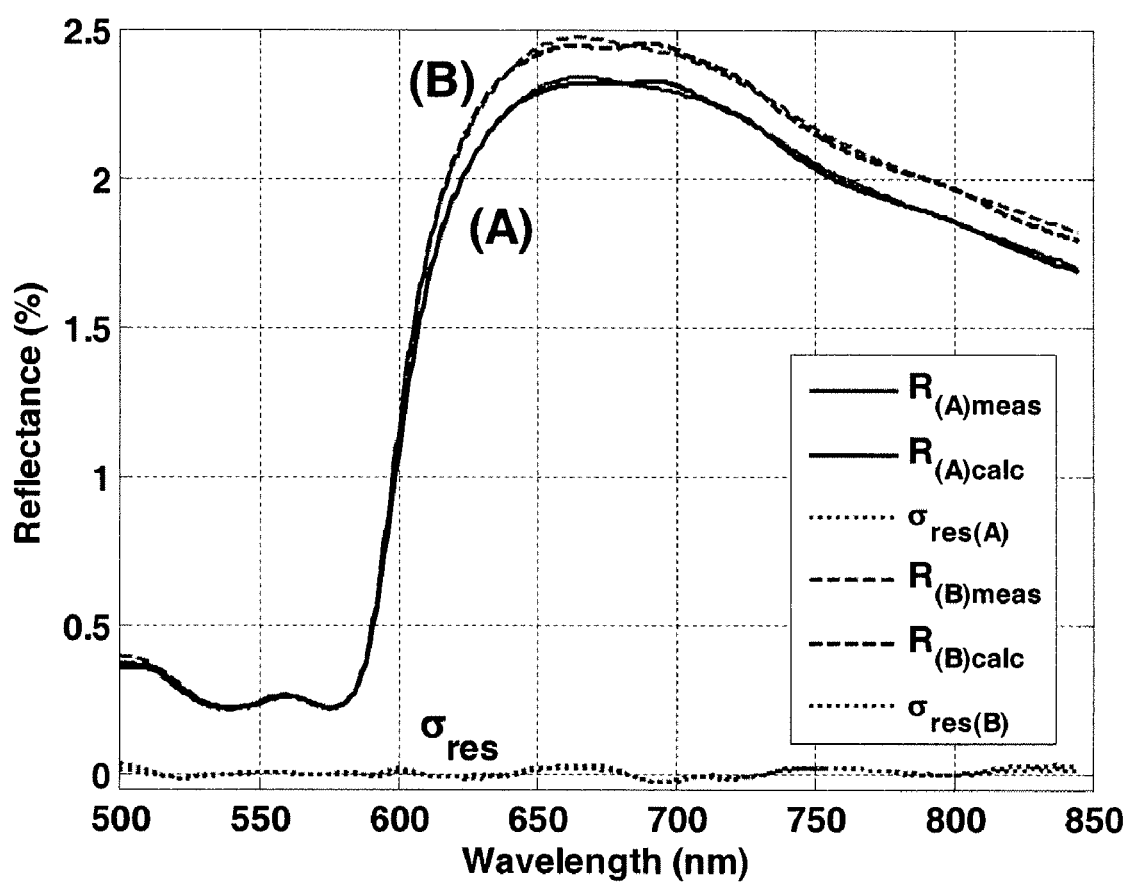
FIG. 15 illustrates the differences between the reflectance spectra associated with two different blood samples with different number density of particles.

FIGS. 13-15 further demonstrate that calculated spectra, based on the interpretation model Equations (1) to (35), correspond well with measured spectra. In particular, FIG. 13 illustrates the calculated and measured spectra of three different uncontaminated blood cultures, designated by the letters A, B and C. Table 1 shows the parameters of blood culture components obtained from deconvolution of the reflectance spectra for each form of hemoglobin (oxy-, deoxy- and met-hemoglobin). The parameters include volume fraction of red blood cells, volume fraction of hemoglobin in the red blood cells, mean cell volume of red blood cells, fraction of oxyhemoglobin, fraction of deoxyhemoglobin, fraction of methemoglobin and residual sum of squares.

TABLE 1

PARAMETERS OF BLOOD CULTURE COMPONENTS OBTAINED
FROM DECONVOLUTION OF REFLECTANCE SPECTRA

| Deconvoluted blood culture parameters | Spectrum A | Spectrum B | Spectrum C |
|---|---|---|---|
| Volume fraction of erythrocytes in blood culture | 0.0564 | 0.0345 | 0.0536 |
| Volume fraction of hemoglobin in erythrocytes | 0.34 | 0.33 | 0.34 |
| Mean cell volume of erythrocytes ($\mu m^3$) | 91.0 | 81.8 | 90.9 |
| Fraction of oxyhemoglobin of total hemoglobin | 0.945 | 0.042 | 0.800 |
| Fraction of deoxyhemoglobin of total hemoglobin | 0.053 | 0.957 | 0.082 |
| Fraction of methemoglobin of total hemoglobin | 0.002 | 0.001 | 0.118 |
| Residual sum of squares | 0.020 | 0.026 | 0.025 |

FIGS. 14 and 15 provide a comparison between calculated and measured spectra of two blood samples, each having a different mean red blood cell volume. FIG. 14 illustrates the observed differences in the shape and magnitude of the reflectance spectra of blood culture samples. These differences are produced due to different mean corpuscular volumes of the scattering elements. In this example, the number density of the scatterers and relevant parameters of particle chemical composition of the compared blood cultures are similar. The deconvolution results are summarized in Table 2. However, since the volume fraction of the scatterers is directly proportional to the mean cell volume of the particles, this parameter also varied between the measured samples.

TABLE 2

PARAMETERS OF BLOOD CULTURE COMPONENTS
OBTAINED FROM DECONVOLUTION OF
REFLECTANCE SPECTRA OF FIG. 14

| Deconvoluted blood culture parameters | Spectrum A | Spectrum B |
|---|---|---|
| Volume fraction of erythrocytes in blood culture | 0.055 | 0.067 |
| Number density of erythrocytes in blood culture ($10^8$ cells ml$^{-1}$) | 6.8 | 6.8 |
| Volume fraction of hemoglobin in erythrocytes | 0.30 | 0.29 |
| Mean cell volume of erythrocytes ($\mu m^3$) | 82.0 | 99.0 |
| Fraction of deoxyhemoglobin of total hemoglobin | 1.0 | 1.0 |
| Residual sum of squares | 0.020 | 0.026 |

FIG. 14 indicates that the effects of both the mean corpuscular volume and the volume fraction of scattering elements appear as differences in the amplitude of the reflectance spectra. A similar example, which is presented in FIG. 15, demonstrates the spectral differences between two samples that are characterized by comparable values for volume fraction of particles and their chemical composition but by different mean particle volumes (see, Table 3). In particular, the sample associated with spectrum B has larger number density of particles.

TABLE 3

PARAMETERS OF BLOOD CULTURE COMPONENTS
OBTAINED FROM DECONVOLUTION OF
REFLECTANCE SPECTRA OF FIG. 15

| Deconvoluted blood culture parameters | Spectrum A | Spectrum B |
|---|---|---|
| Volume fraction of erythrocytes in blood culture | 0.073 | 0.073 |
| Number density of erythrocytes in blood culture ($10^8$ cells ml$^{-1}$) | 7.9 | 9.5 |
| Volume fraction of hemoglobin in erythrocytes | 0.30 | 0.29 |
| Mean cell volume of erythrocytes ($\mu m^3$) | 92.0 | 77.0 |
| Fraction of oxyhemoglobin of total hemoglobin | 0.915 | 0.915 |

TABLE 3-continued

PARAMETERS OF BLOOD CULTURE COMPONENTS
OBTAINED FROM DECONVOLUTION OF
REFLECTANCE SPECTRA OF FIG. 15

| Deconvoluted blood culture parameters | Spectrum A | Spectrum B |
|---|---|---|
| Fraction of deoxyhemoglobin of total hemoglobin | 0.084 | 0.085 |
| Fraction of methemoglobin of total hemoglobin | 0.001 | 0.0001 |
| Residual sum of squares | 0.049 | 0.089 | i. Example

*Candida albicans*

Figure 16:
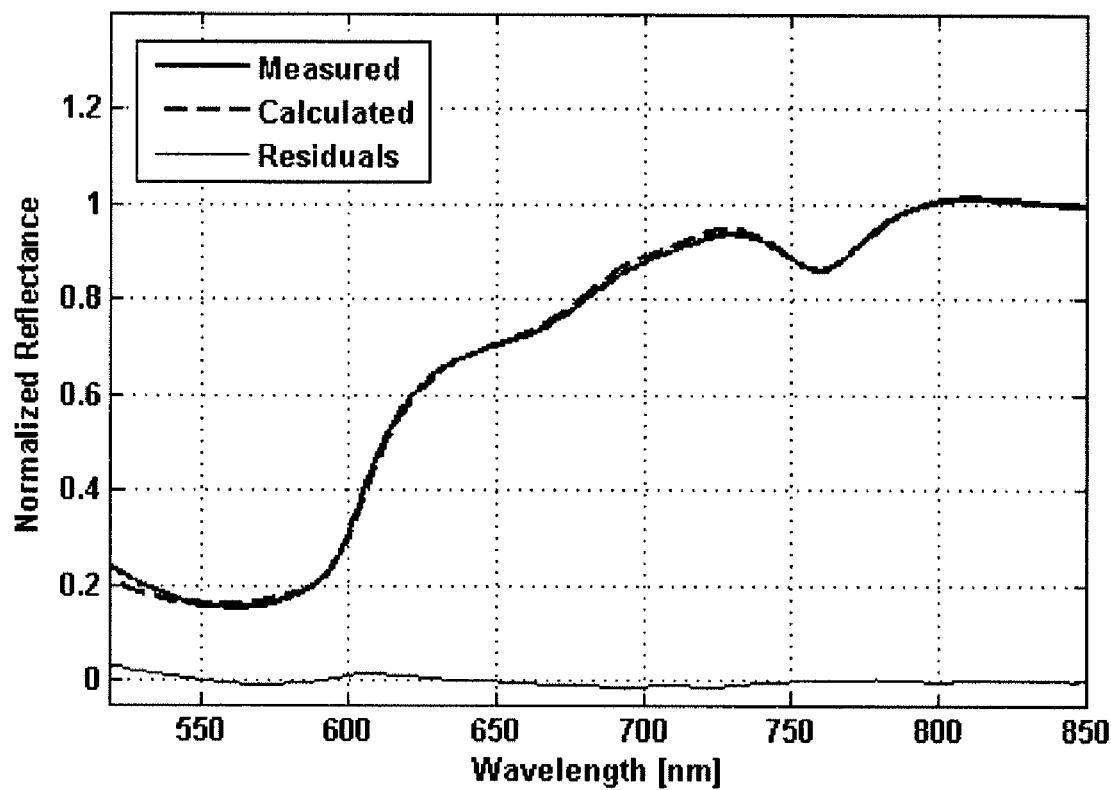
FIG. 16 presents the measured and calculated reflectance spectra of a blood sample contaminated with yeast, C. albicans.

FIG. 16 shows a comparison between measured spectra of a blood sample contaminated with the yeast *Candida albicans* at 21.5 hours post-inoculation and the corresponding theoretically calculated spectra. Deconvolution results carried out in accordance with of the principles of the present invention indicate that the measured spectrum has a high deoxyhemoglobin content.

In the above examples, the spectra were fitted between 500-850 nm, where the spectral data has an acceptable signal to noise ratio. The residuals of the deconvolution confirm that the model accurately describes the data over the wavelength range of interest.

Figure 17:
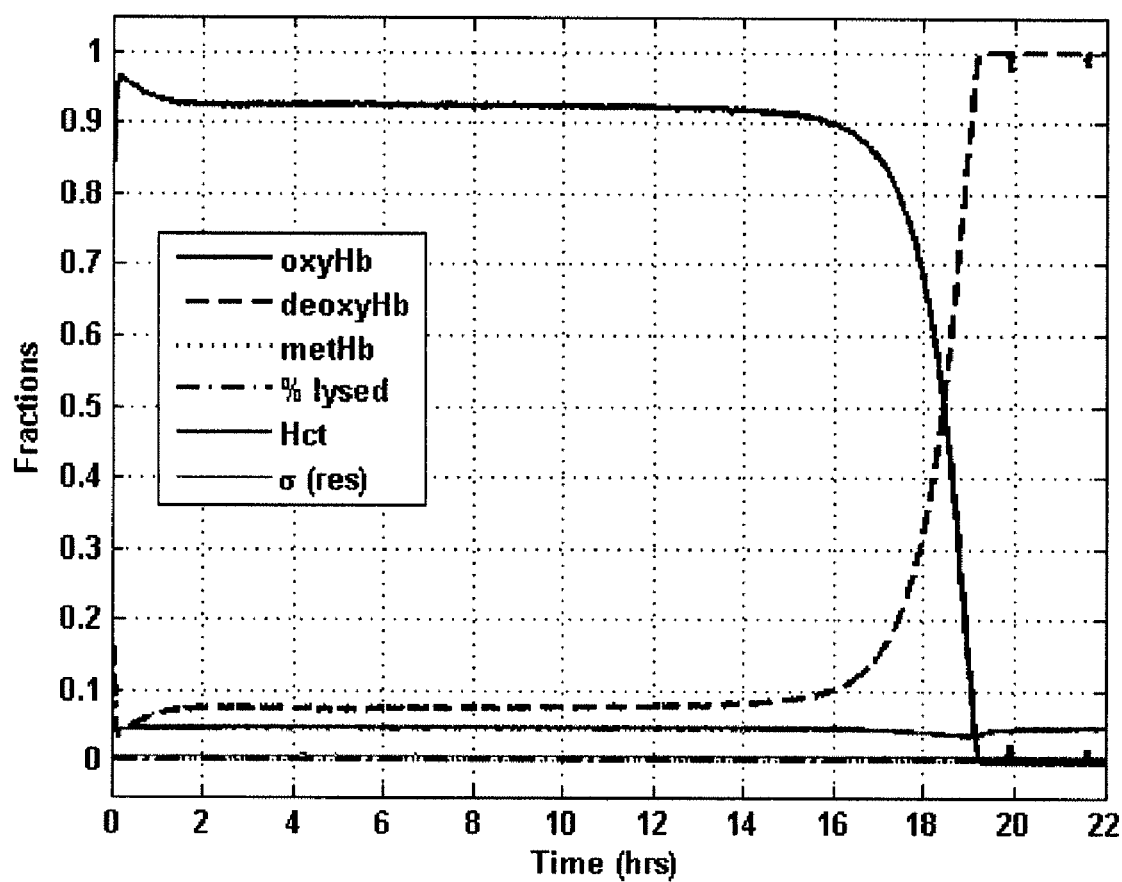
FIG. 17 illustrates the conversion of different forms of hemoglobin associated with a blood sample contaminated with C. albicans.
Figure 18:
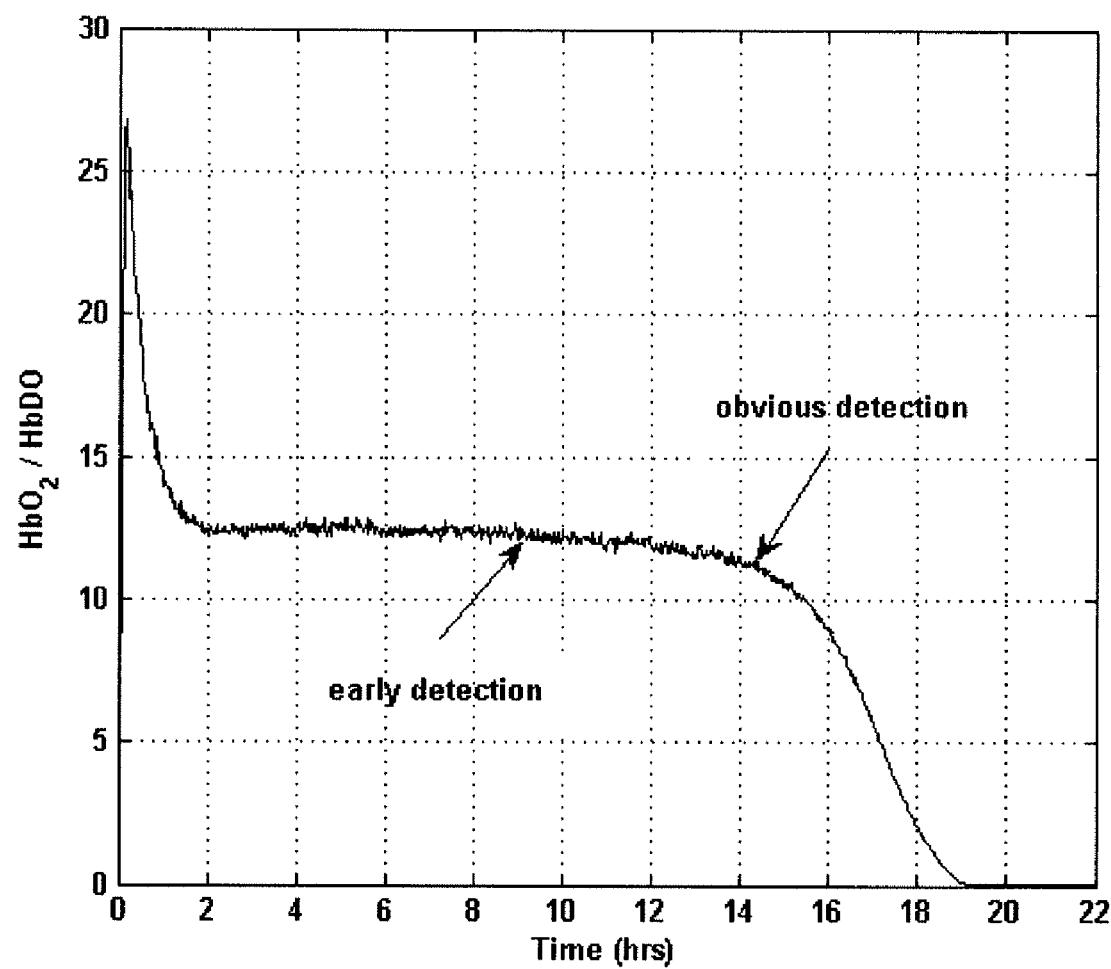
FIG. 18 depicts the conversion of the ratio of oxy- to deoxy-hemoglobin over time for a blood sample contaminated with C. albicans.

The complete sequence of events of any blood culture experiment can be interpreted in terms of the changes in hemoglobin composition, the number of particles present, and the physical and chemical properties of the sample at any time point during the experiment (see, for example, Equations 21-27). An example of such changes in the hemoglobin composition over time is shown for *C. albicans* in FIGS. 17 and 18. The dramatic conversion from oxy- to deoxyhemoglobin apparent at 15 hours, as illustrated in FIG. 17, indicates an increased metabolic activity of microorganisms. Moreover, the sensitivity of the deconvolution methods based on the principles of the present invention enables an earlier detection of the changes in the rate of conversion. This enhanced detection capability of the change in the ratio of oxy- to deoxyhemoglobin over time can be better appreciated by examining the plot in FIG. 18. As illustrated in FIG. 18, the microorganism may be detected as early as about 10 hours past the initial inoculation, whereas an obvious detection would occur at about 14 hours past inoculation.

ii. Example

*Escherichia coli*

Figure 19:
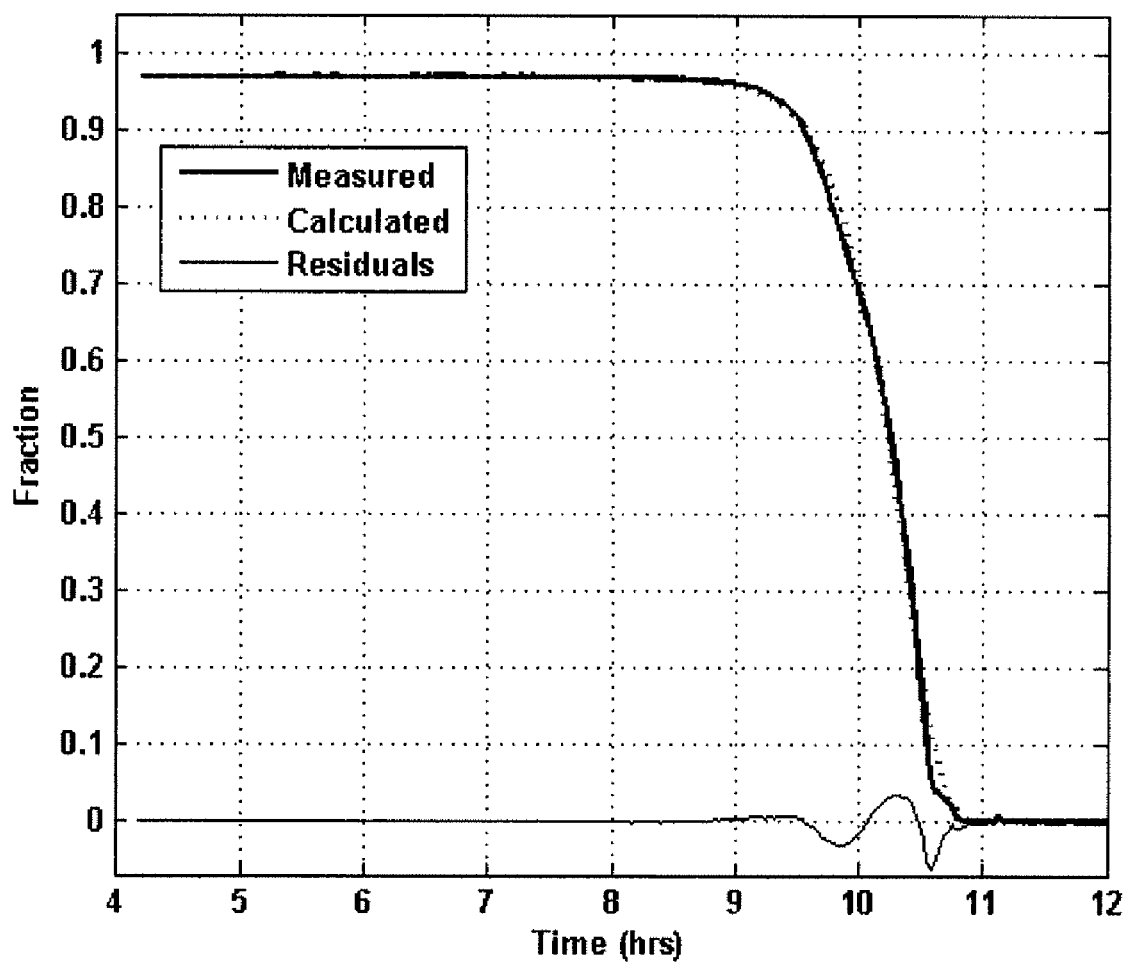
FIG. 19 illustrates changes in hemoglobin composition as a function time for a blood sample that is contaminated with bacteria, E. coli.

Pursuant to the principles of the present invention, identifying characteristics of microorganisms can be extracted using the deconvolution techniques described above. These characteristics include, but are not limited to, kinetic growth parameters, such as doubling time and respiration rate, and physical characteristics such as size and shape. For example, FIG. 19 shows that a logistic growth model can be fitted to changes in hemoglobin composition as a function of time for a blood culture experiment using *Escherichia coli*. Again, note the excellent fit of the composition data. The doubling time of *E. coli* was estimated to be 30 minutes for this experiment.

iii. Example

*Clostridium perfringens*

In anaerobic conditions, hemoglobin equilibration with an oxygen deficient environment converts the hemoglobin to approximately 98% deoxyhemoglobin immediately after inoculation into the bottle. The hemoglobin composition remains approximately constant throughout the culture time course. Unlike the aerobic case, the main indicator of microbial metabolic activity is the change in the particle or cell density. Notice that in the anaerobic case, because the remainder of the oxyhemoglobin is converted to deoxyhemoglobin at an early stage, it is not used as an indicator. However, other indicators in contact with the liquid may be used. In the case of hemolytic organisms, an increase in free hemoglobin concentration is consistent with increased microbial metabolic activity.

Figure 20:
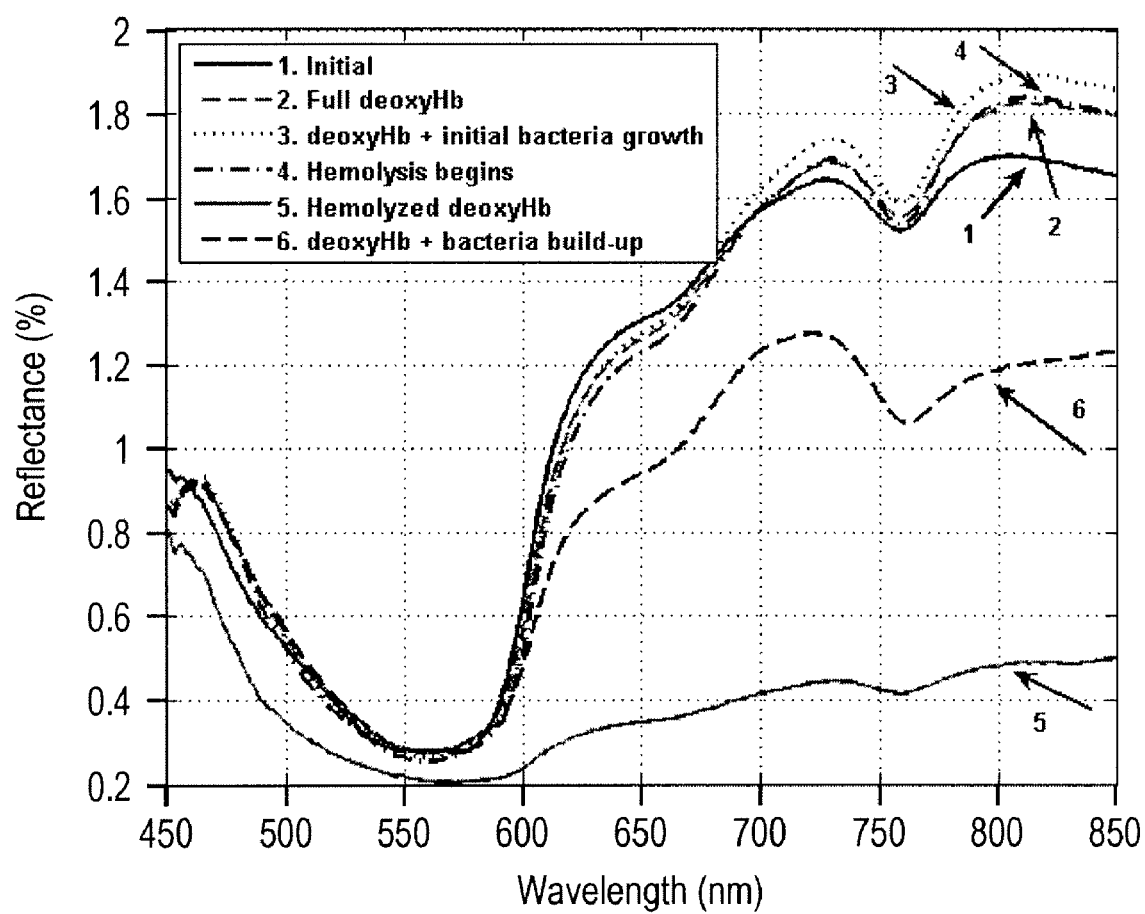
FIG. 20 shows an evolution of reflectance spectra over time, associated with a blood sample contaminated with bacteria, C. perfingens.

FIG. 20 shows an exemplary reflectance spectra obtained from a blood culture experiment performed with the hemolytic bacteria *C. perfringens*. Equilibration between the hemoglobin composition and the anaerobic environment is apparent in the initial hours of the experiment (FIG. 20, spectrum 1). After the hemoglobin composition stabilizes (spectrum 2), changes in the shape and magnitude of the spectrum (spectrum 3) are indicative of bacterial growth. At this stage, the presence of microorganisms becomes spectroscopically evident. In this particular case, after reaching this stage, the bacterial concentration produces a level of exotoxin that is sufficient to cause significant lysis of the red blood cells (transition from spectrum 4 to spectrum 5). Note the significant reduction in intensity of reflectance spectrum 5 that occurs in conjunction with the decrease in the number of particles. The increased reflectance intensity (spectrum 6) observed after the lysis of red blood cells is due to the continued increase in bacterial biomass.

Figure 21:
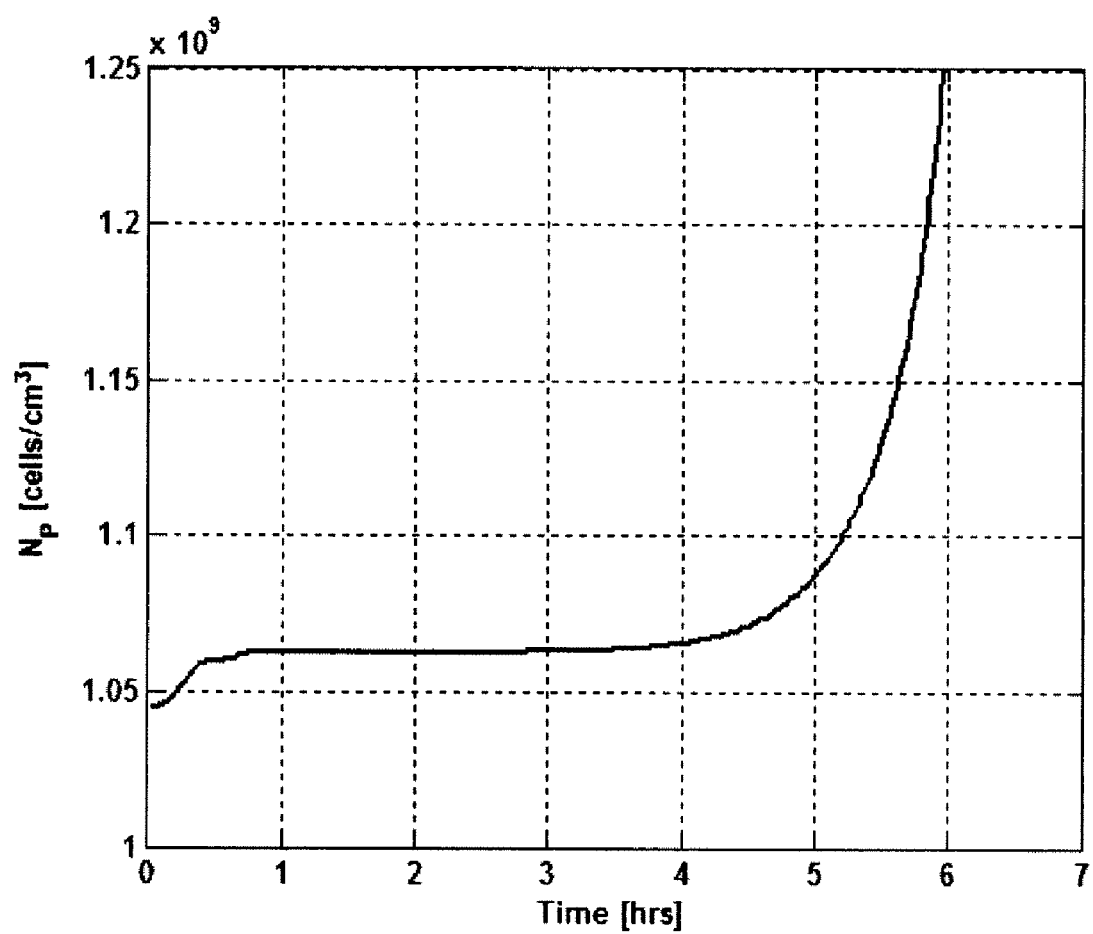
FIG. 21 illustrates changes in cell density over time, associated with the blood a a blood sample contaminated with C. perfingens.

The spectral features shown in FIG. 20 were quantified using the earlier-described deconvolution techniques in accordance with principles of the present invention. FIG. 21 shows the changes in the cell density as functions of time obtained from the spectral data. As is evident from FIG. 21, according to the principles of the present invention, the presence of this organism may be detected (obvious detection) at about 7.5 hours, but as early as 4.0 hours. In the systems of prior art, such as the BacT/ALERT system, this identification was made after 12.2 hours.

iv. Example

Multiple Microorganisms

Figure 22B:
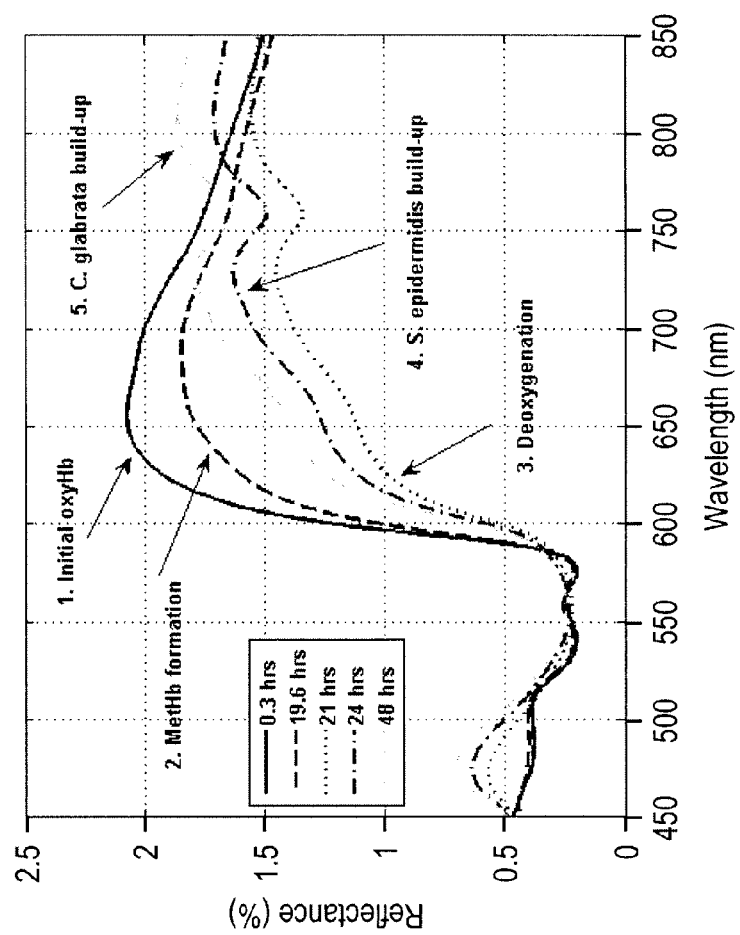
FIG. 22(B) illustrates the evolution of the reflectance spectra over time associated with a blood sample contaminated with two microorganisms.
Figure 22A:
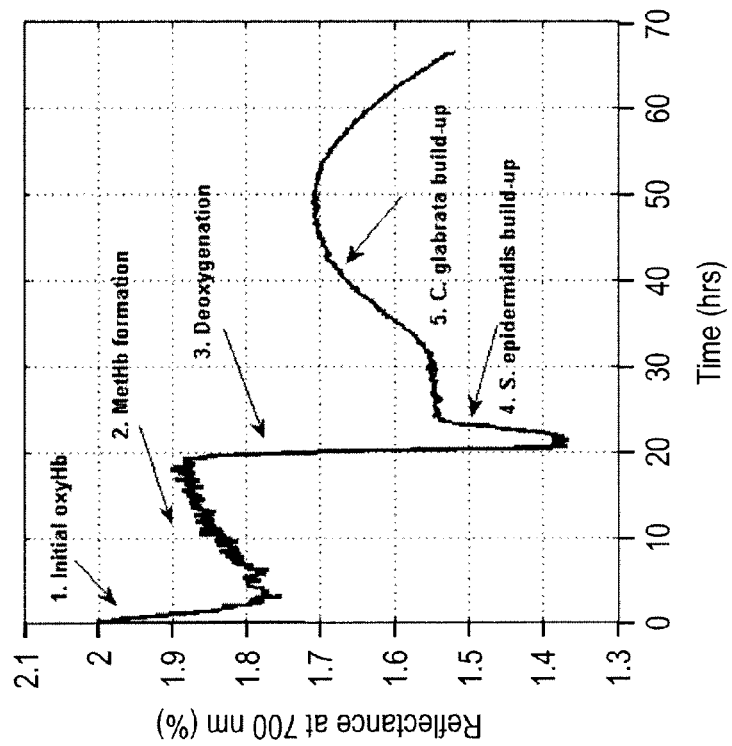
FIG. 22(A) shows the evolution of a single wavelength reflectance spectrum over time, associated with a blood sample contaminated with two microorganisms.

FIGS. 22(A) and 22(B) illustrate exemplary reflectance spectra associated with an experiment in which two different microorganisms, *C. glabrata* (yeast) and *Staphylococcus epidermidis* (bacteria), were present in the same blood sample. To facilitate understanding of the underlying detection principles of the present invention, FIG. 22(A) is specifically produced to illustrate the time evolution of reflectance values at a single wavelength, 700 nm. FIG. 22(A) demonstrates the changes in reflectance values associated with the (1) initial oxyhemoglobin, (2) formation of methemoglobin, (3) deoxygenation, (4) *S. epidermidis* buildup, and (5) *C. glabrata* buildup. As illustrated in FIG. 22(A), the presence and type of the two microorganisms can be readily distinguished from the reflectance values. FIG. 22(B) shows the time evolution of the reflectance spectra over a large span of wavelengths that can be used to assess the presence, absence and/or identity of multiple microorganisms. Unlike the above-described methodology of the present invention, conventional systems cannot detect the presence of multiple pathogens and do not provide any information about the pathogen growth behavior.

Figure 23:
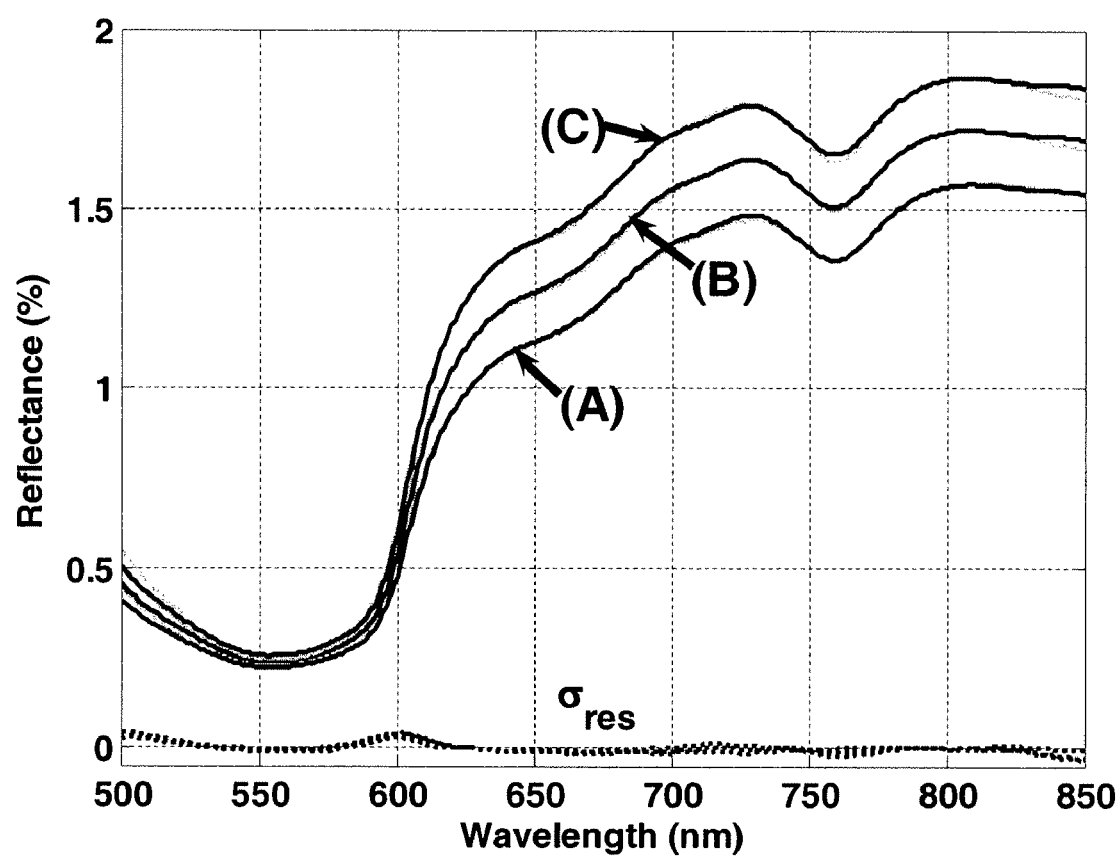
FIG. 23 illustrates the differences between the measured and calculated reflectance spectra associated with a blood sample contaminated with multiple microorganisms.

FIG. 23 illustrates a comparison between calculated and measured spectra for a blood sample at different time steps of a blood culture experiment with multiple contaminants, specifically bacterium *Staphylococcus epidermidis* and yeast *Candida glabrata*. FIG. 23 illustrates the measured ($R_{meas}$) and predicted ($R_{calc}$) reflectance spectra and residuals ($\sigma_{res}$) for blood culture samples characterized by one particle population (erythrocytes) (designated as A), two particle populations (erythrocytes and bacterial cells) (designated as B), and three particle populations (erythrocytes, bacterial cells, and yeast cells) (designated as C) in the 500-850 nm spectral range. Although microbial contaminants growing in blood cultures typically have small sizes (for example, characteristic average diameter of bacteria is about 0.5-2 μm and yeast cells are typically 3-10 μm in diameter), they usually reach the number densities of $10^7$-$10^9$ cells per ml in positive blood cultures, and thus can alter the reflectance signal. Referring back to FIG. 23, since the two different microorganisms have different growth rates and, therefore, correspondingly different times needed to reach optically important number density values, it is possible to capture their individual contributions to the reflectance signals. In FIG. 23, the spectral change from spectrum A to spectrum B resulted from *S. epidermidis* reaching a calculated number density of $0.8 \cdot 10^9$ cells per ml. This number and other relevant parameters of blood culture components obtained from the deconvolution of the diffuse reflectance spectra of FIG. 23 are represented in Table 4. The cells of *S. epidermidis* typically form clusters, the mean cell volume of which was estimated to be 3 μm³ (see Table 4). Further, the growth of *C. glabrata* produced additional spectral changes that are represented by the shift from spectrum B to spectrum C in FIG. 23. The corresponding estimates of the mean cell volume and cell density for *C. glabrata* cells obtained from deconvolution of spectrum C were 33.5 μm³ and $7 \cdot 10^7$ cells per ml, respectively (see, Table 4).

TABLE 4

PARAMETERS OF BLOOD CULTURE COMPONENTS OBTAINED FROM DECONVOLUTION OF THE REFLECTANCE SPECTRA OF FIG. 23

| Deconvoluted blood culture parameters | Spectrum A | Spectrum B | Spectrum C |
|---|---|---|---|
| Total volume fraction of scatters in blood culture | 0.0836 | 0.0860 | 0.0880 |
| Number density of erythrocytes in blood culture ($10^8$ cells $ml^{-1}$) | 9.3 | 9.2 | 9.2 |
| Volume fraction of hemoglobin in erythrocytes | 0.32 | 0.32 | 0.32 |
| Mean cell volume of erythrocytes ($\mu m^3$) | 90.0 | 90.0 | 90.0 |
| Fraction of deoxyhemoglobin of total hemoglobin | 0.9999 | 0.9999 | 0.9998 |
| Number density of bacterial cells in blood culture ($10^8$ cells $ml^{-1}$) | — | 8.0 | 4.0 |
| Mean cell volume of bacteria ($\mu m^3$) | — | 3.0 | 3.0 |
| Number density of yeast cells in blood culture ($10^8$ cells $ml^{-1}$) | — | — | 7.0 |
| Mean cell volume of yeast ($\mu m^3$) | — | — | 33.5 |
| Residual sum of squares | 0.053 | 0.075 | 0.067 |

The results presented in FIGS. 14-23 clearly indicate that, according to the principles of the present invention, a quantitative analysis is feasible from the combination of diffuse reflectance measurements and a suitable interpretation model. As such, the physiological properties of blood and other cellular components of blood cultures can be captured with diffuse reflectance and quantitatively resolved.

v. Example

Partial Pressures

The following three exemplary case studies demonstrate the capabilities of the integrated process-measurement model and the sensitivity of the reflectance spectroscopy model for the detection of bacterial growth that are carried out in accordance with the principles of the present invention.

Case I demonstrates the results from the model for the exemplary reference data shown in FIG. 24 for both a control and a contaminated sample.

Case II reports on the effects of blood sample volume, an important parameter for current blood culture technology.

Case III demonstrates an example where the blood composition is changed with increased white blood cell counts (i.e. leukemic patients). This case is representative of a likely a cause of false positives in the detection systems of prior art.

Figure 25:
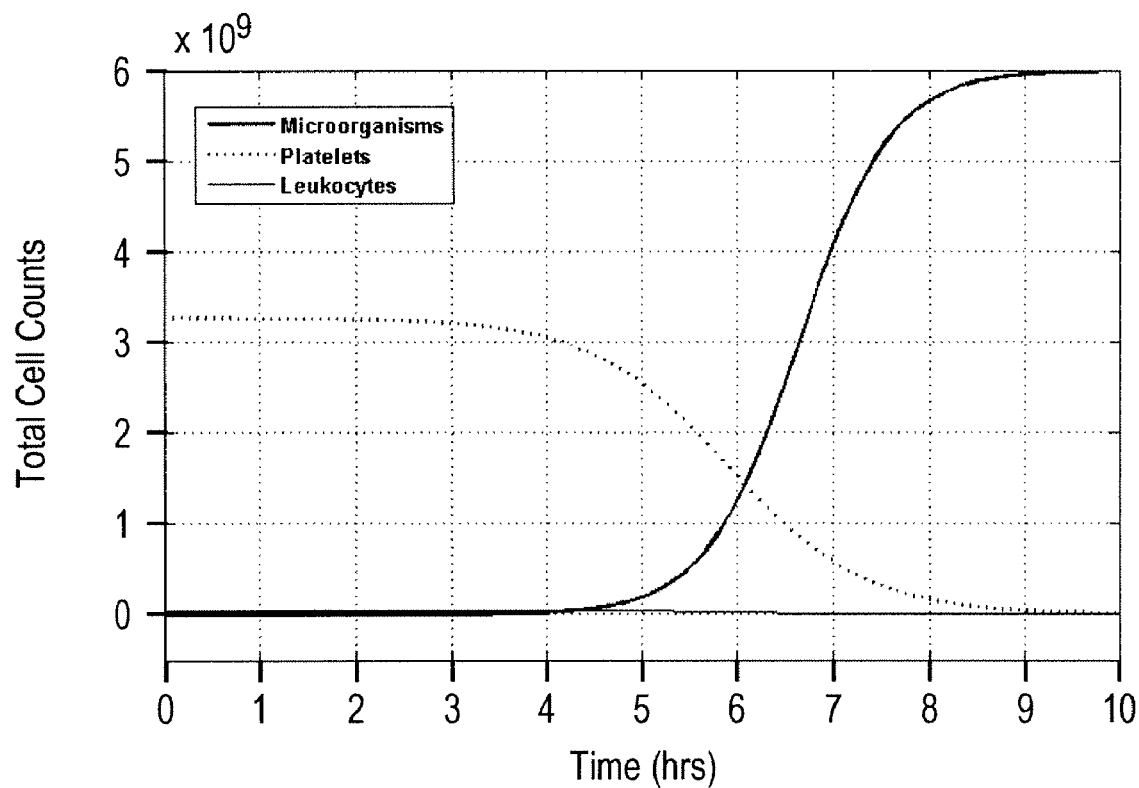
FIG. 25 depicts an evolution of total cell count over time associated with a blood sample.
Figure 26:
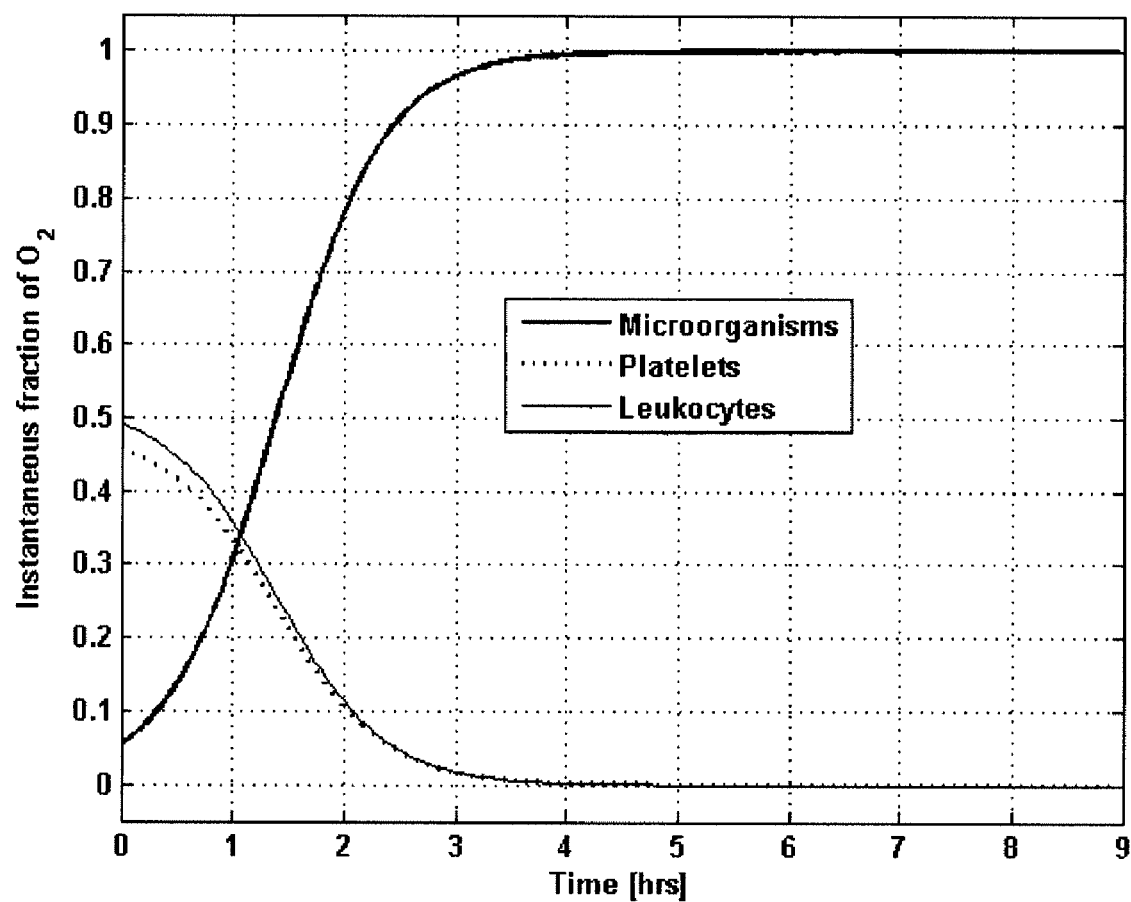
FIG. 26 illustrates an evolution of oxygen consumption over time associated with a blood sample.

Case Study I:

FIG. 25 contrasts microbial growth with the decay of platelet and leukocyte populations for venous blood using the reference data shown in FIG. 24 (10 mL blood; $ppO_2$=30 nm hg; $ppCO_2$=50 mmHg). Both the parameter values selected and the cell densities are typical of what is encountered in practical situations. The doubling time for the microorganism is within the range of aerobic bacteria grown in nutrient rich media. FIG. 26 shows the fractional consumption of oxygen by each of the cell populations.

Figure 27:
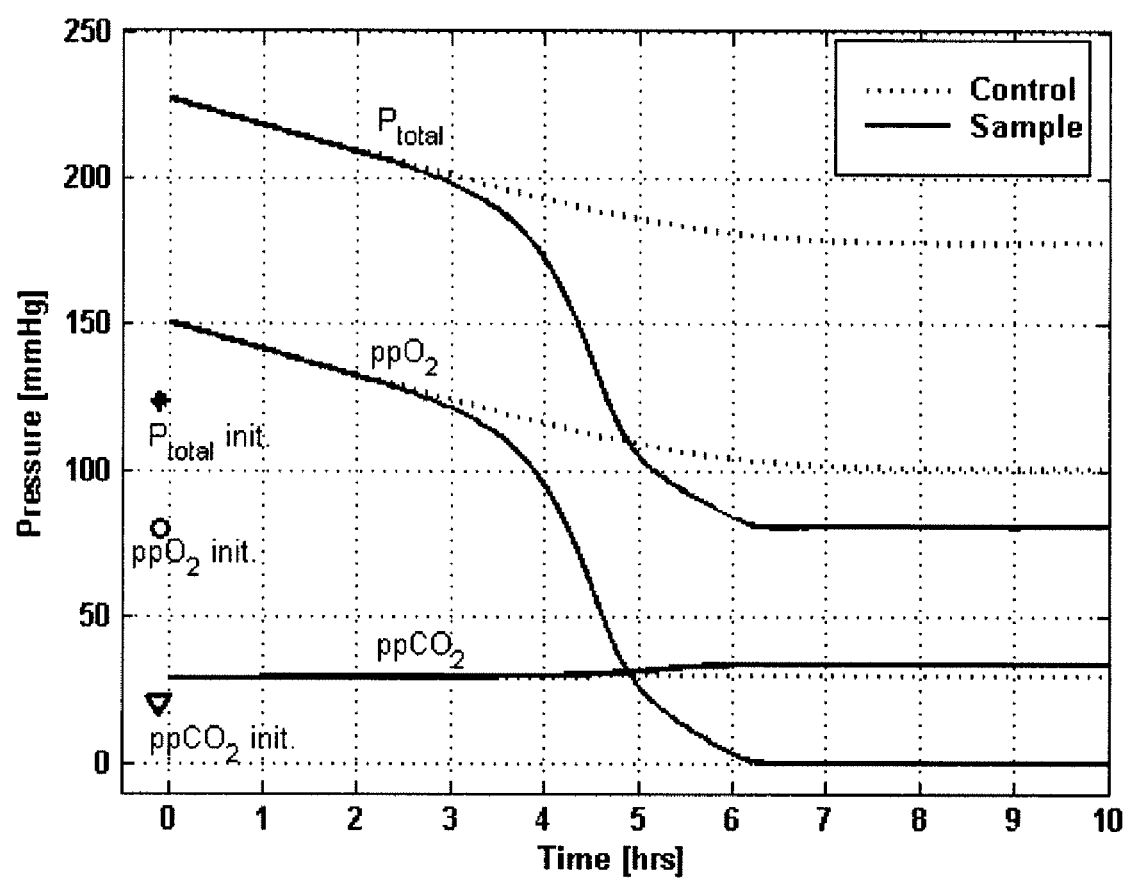
FIG. 27 illustrates an evolution of gas pressure profiles over time associated with a blood sample.

The respiration of white blood cells and platelets initially dominate the $O_2$ consumption causing a corresponding decrease in the oxygen partial pressure. Note that although platelets are more numerous, the specific respiration rate of the white blood cells is such that the oxygen consumption is approximately the same for each population. The microorganisms are the most active population with a relatively high metabolic rate and have continuously increasing numbers. The microbial growth results in a high rate of oxygen consumption which is clearly evident during the lag phase of the growth (~4-6 hours). The distribution of $O_2$ and $CO_2$ between the liquid and gaseous phases present in the culture bottles is shown in FIG. 27 as a function of time for a control sample and a sample contaminated with 100 microbial CFU/mL of blood. The pressure in the vial is resulting from the contributions of water, oxygen and carbon dioxide (the system is under vacuum). In the case of the control sample (i.e., no microorganisms), the pressure stabilizes once the populations of white blood cells and platelets become inactive. In the case of the contaminated sample, the decrease in $O_2$ partial pressure continues unabated at a rate proportional to the bacterial growth: a function of its specific growth rate and respiration rate. The point at which the two lines separate can be used to detect the presence of microorganisms.

Figure 28:
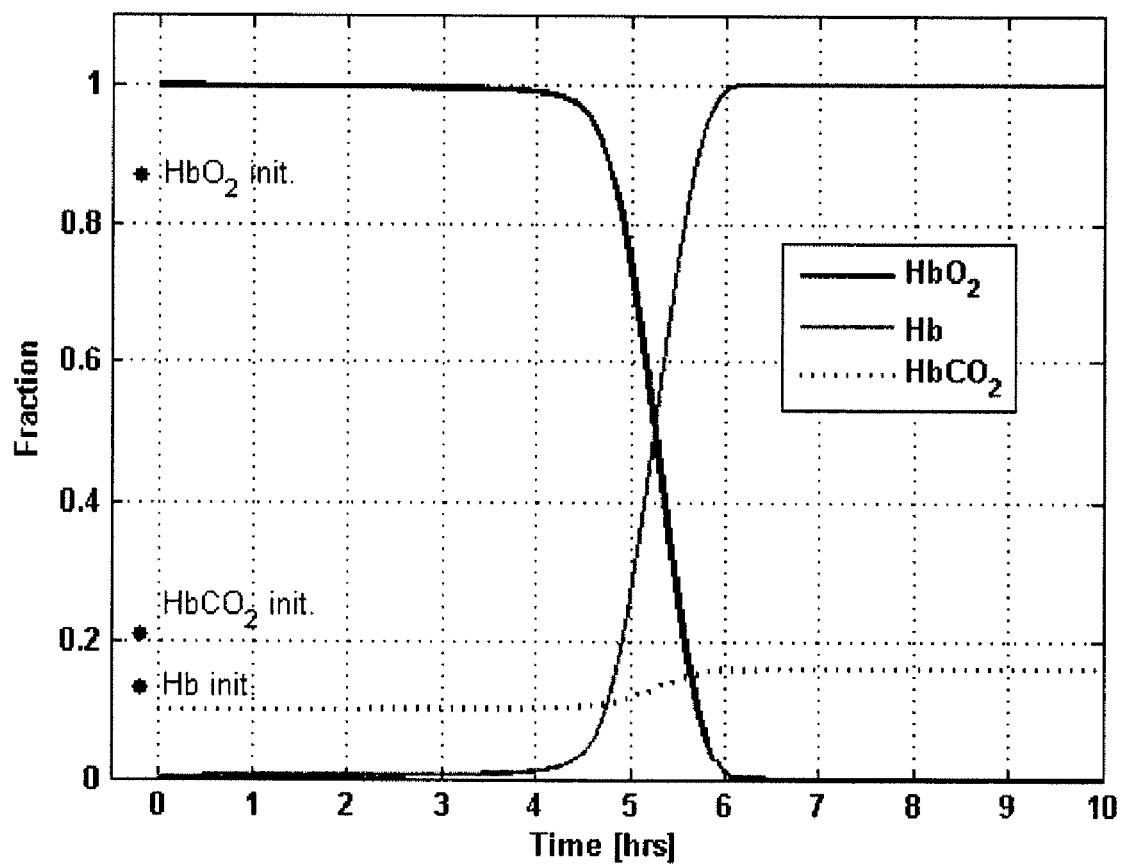
FIG. 28 shows a simulated evolution of hemoglobin composition profile over time associated with a blood sample.
Figure 29:
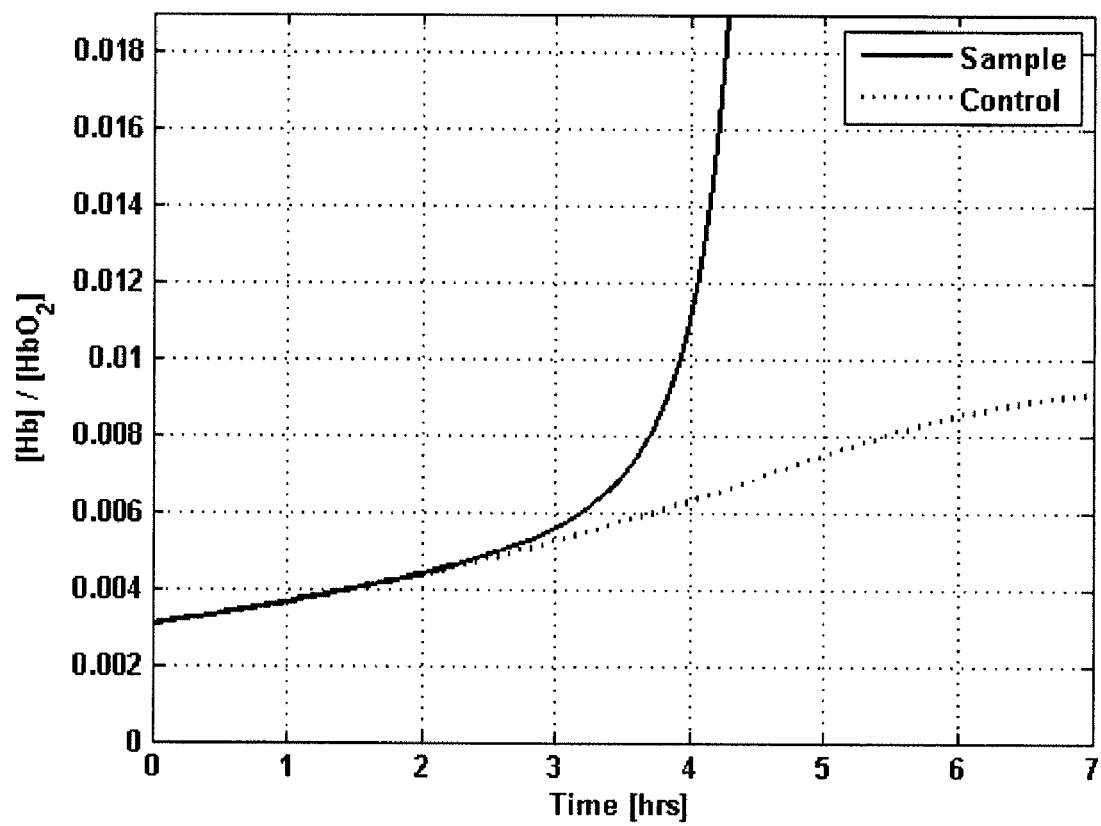
FIG. 29 illustrates the evolution of simulated hemoglobin ratios over time associated with two different blood samples.

The changes in the chemical composition of hemoglobin are shown in FIG. 28. The variation in the concentrations of oxy-, deoxy-, and carbamino-hemoglobin are the result of the changes in the partial pressures of oxygen and carbon dioxide throughout the evolution of the process. The ratio of deoxy- to oxy-hemoglobin ([Hb]/[HbO$_2$]) is sensitive to changes in partial pressures and is shown in FIG. 29. Note that the ratio ([Hb]/[HbO$_2$]) can be obtained directly from deconvoluted reflectance measurements.

The reflectance spectra, as described earlier, are functions of the cell densities, the changes in the physical and chemical properties of blood, and the absorption and scattering properties of the cell populations present in the mixture. In addition, the effect of the chemical composition is introduced directly through the additive properties of the complex refractive index. The reflectance model is comprehensive relative to the measurement variables. The results reported herein focus on the variables relevant to changes in the chemical composition of hemoglobin. The reflectance spectra for the exemplary blood properties listed in FIG. 24 were previously illustrated in FIG. 5, for different forms of hemoglobin, including the two principal forms, oxy- and deoxy-hemoglobin. Notice the distinct spectral features that are characteristic of each hemoglobin species; in the measurement mode, these distinct features enable an accurate quantitative spectral deconvolution. Using the properties of the blood included in listing of FIG. 24, the physical and chemical changes represented by Equations 28-31, and the changes in chemical composition shown in the exemplary plots of FIG. 5, the evolution of the reflectance spectra as a function of time may be predicted in accordance with the principles of the present invention. Note that FIG. 9 further shows the spectra over the complete time course of the experiment.

Case Study II:

The volume of blood inoculated into the blood culture bottles constitutes an important parameter for two reasons. For the low pathogen numbers, an increase in the blood volume leads to a higher likelihood that the sample contains the pathogen. From the measurement sensitivity point of view, different blood volumes result in different distributions of oxygen and carbon dioxide between the liquid and vapor phases. Since the liquid phase acts as a capacitor for $CO_2$ and the vapor phase acts as a capacitor for $O_2$, changes in the amount of blood injected can be expected to affect the partial pressure of $O_2$. The optimal sample has the largest concentration of microorganisms in the smallest blood volume.

Figure 30:
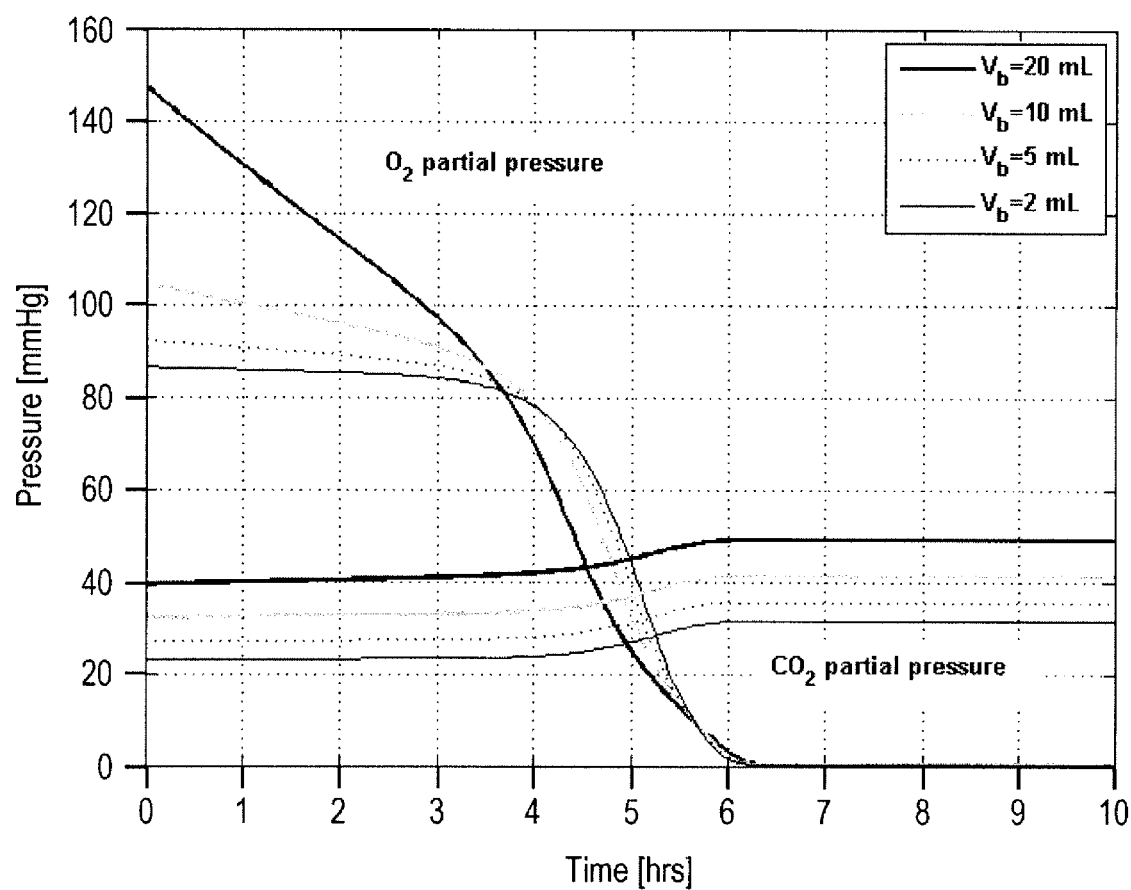
FIG. 30 represents the effects of blood volume on partial gas pressures associated with a blood sample.

The effect of the addition of different volumes of blood (for example, 2, 5, 10, and 20 mL; $ppO_2$=30 mmHg, $ppCO_2$=50 mmHg) on the $O_2$ and $CO_2$ partial pressures is shown in FIG. 30. As the volume of blood increases, not only do the partial pressures increase substantially, but the baseline for the determination of bacterial growth becomes less distinguishable. As a consequence, indication as to whether or not there is bacterial growth present is delayed until the organisms are in the lag phase.

Figure 31:
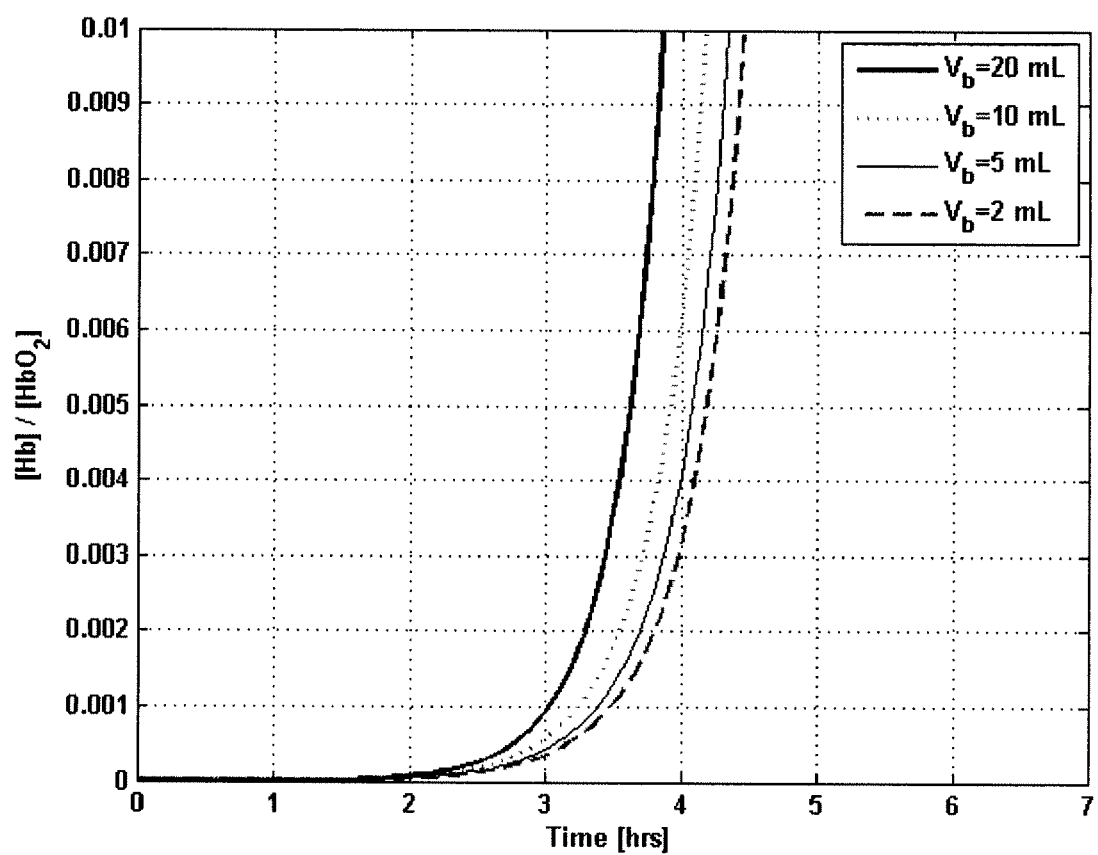
FIG. 31 illustrates the effects of blood volume on the ratio of hemoglobin forms associated with a blood sample.

An advantage of spectrophotometric measurements is that they are self-calibrating in the sense that a spectral deconvolution yields quantitative information on the hematocrit and the relative concentration of deoxy- and oxy-hemoglobin during the early stages of the blood culture. FIG. 31 shows the corrected ratio of [Hb]/[HbO2] obtained in this manner. As expected, an increased volume of the blood sample provides a larger initial concentration of microorganisms and as a result, a shorter time to detection.

Case Study III:

When blood culture detection systems are based only on the production of $CO_2$ as a measure of microbial growth, the respiration of other cells (e.g., leukocytes and platelets) may become a confounding factor, especially if it results in a false positive culture. This is of particular importance in the case of leukemic patients who have elevated concentrations of leukocytes. While only the effects of normal respiration are being considered in this case, leukocytes can also react to the presence of pathogens, and are known to generate a respiratory burst in which $O_2$ consumption can increase by 2-3 fold in the process of destroying the microorganisms [Lee, 1999].

Figure 32:
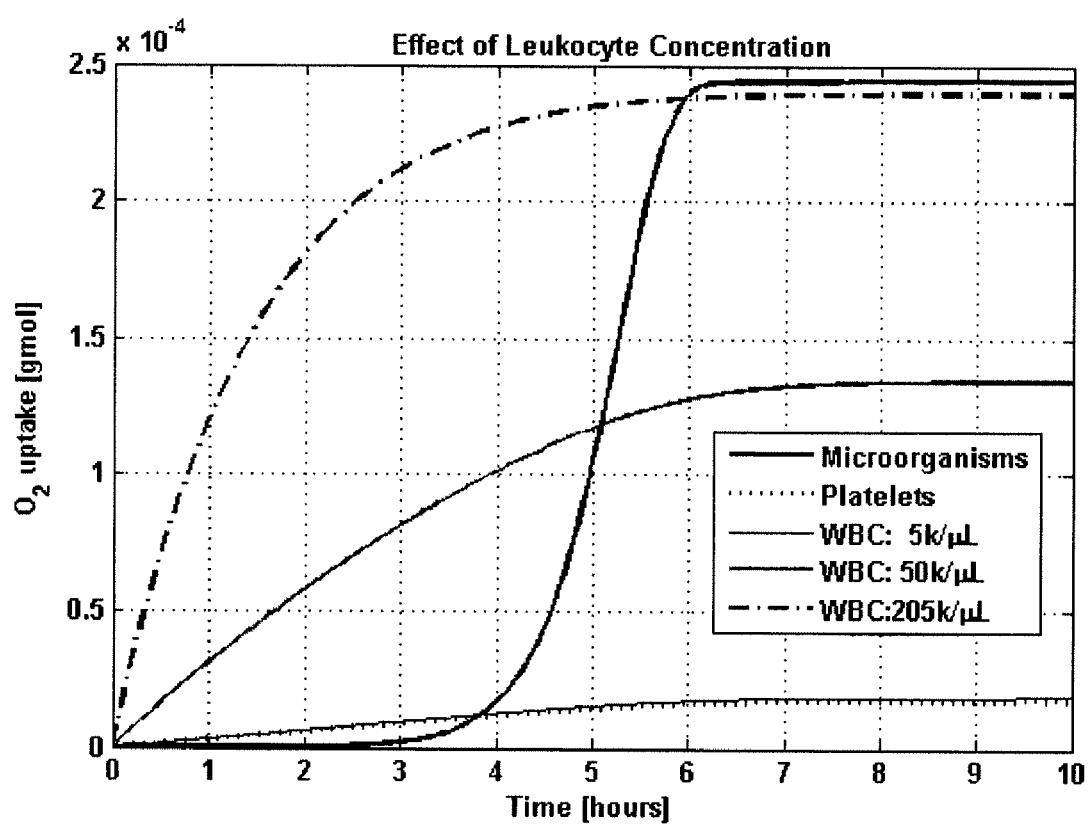
FIG. 32 shows the predicted effects of leukocyte concentration on oxygen uptake associated with a blood sample.
Figure 33:
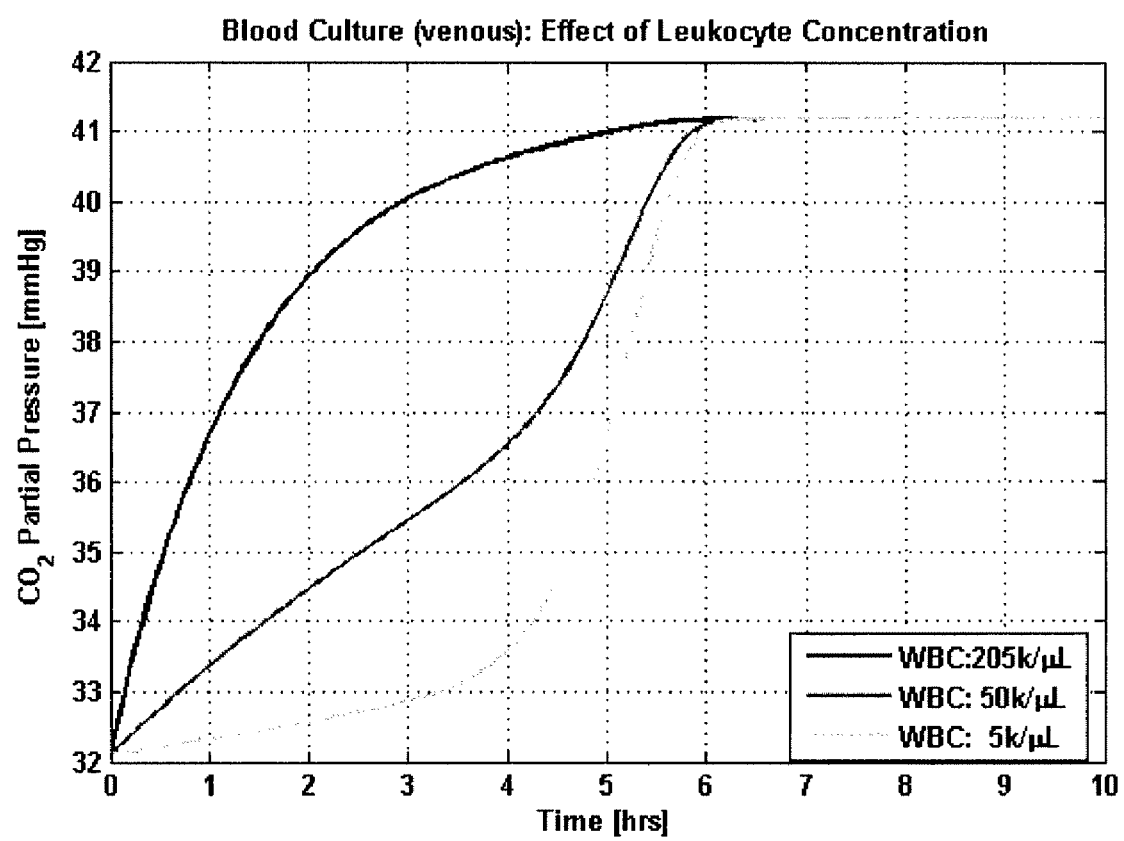
FIG. 33 illustrates the predicted effects of leukocyte concentration on partial gas pressures associated with a blood sample.
Figure 34:
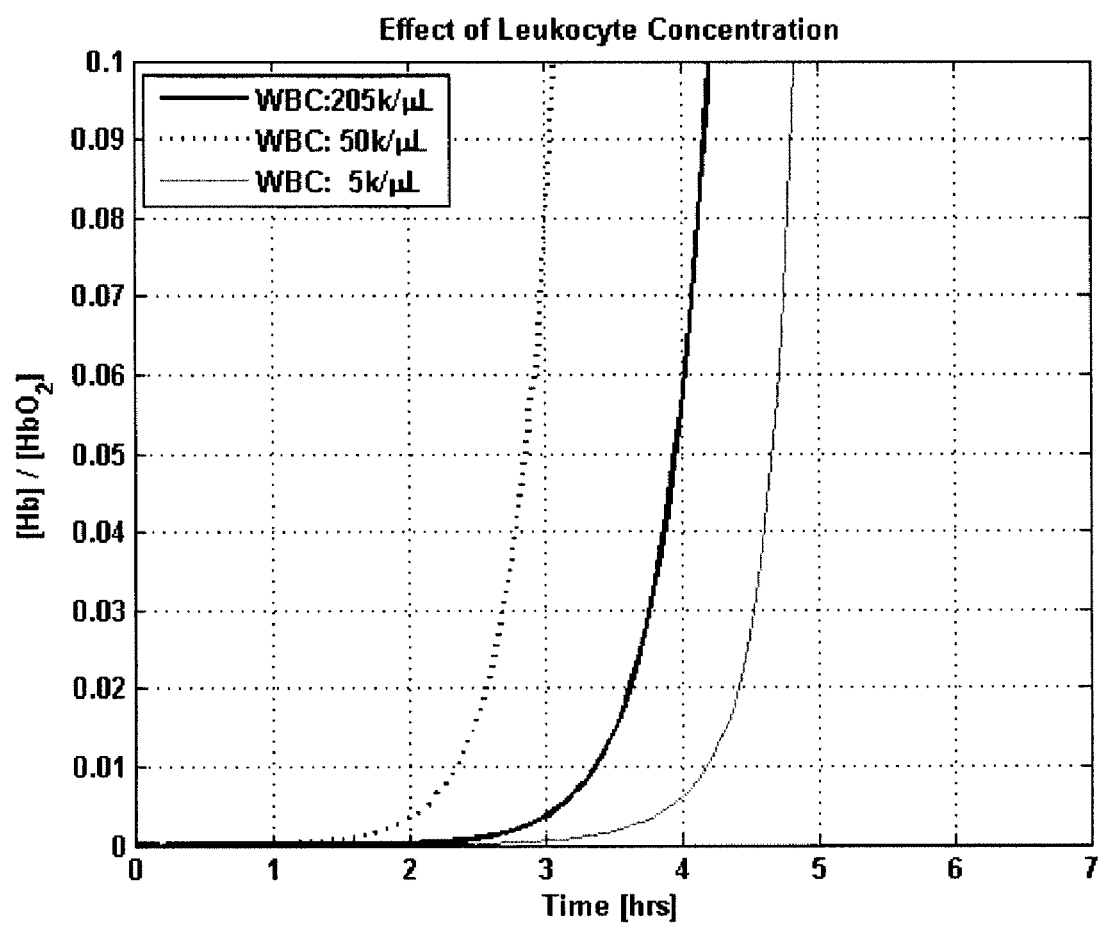
FIG. 34 illustrates the predicted effects of leukocyte concentration on the ratio of hemoglobin forms associated with a blood sample.

Using the parameters of blood from Case I, FIGS. 32 and 33 illustrate the changes in partial pressures of $CO_2$ and $O_2$ in the headspace of an infected blood culture for both normal (5,000 WBC/μL blood) and elevated leukocyte levels (50,000 and 250,000 WBC/mL blood). It becomes more difficult to uniquely distinguish the contribution of microbial metabolism from the respiratory processes of the blood itself, using a direct total pressure or partial pressure measurement. On the other hand, spectrophotometric measurements of the reflectance spectra and their deconvolution, in terms of oxy- and deoxy-hemoglobin, reveal unique changes that can be linked directly to the presence of bacterial growth. Furthermore, the hemoglobin composition can be readily corrected to enable the detection of microorganisms by use of the quantitative information pertaining to the hematocrit and the relative concentration of oxy- and deoxy-hemoglobin during the early stages of the blood culture. FIG. 34 shows the evolution of the hemoglobin composition ([Hb]/[HbO2]) in a blood culture as function of time for the three leukocyte concentrations under consideration.

Validation

Figure 35:
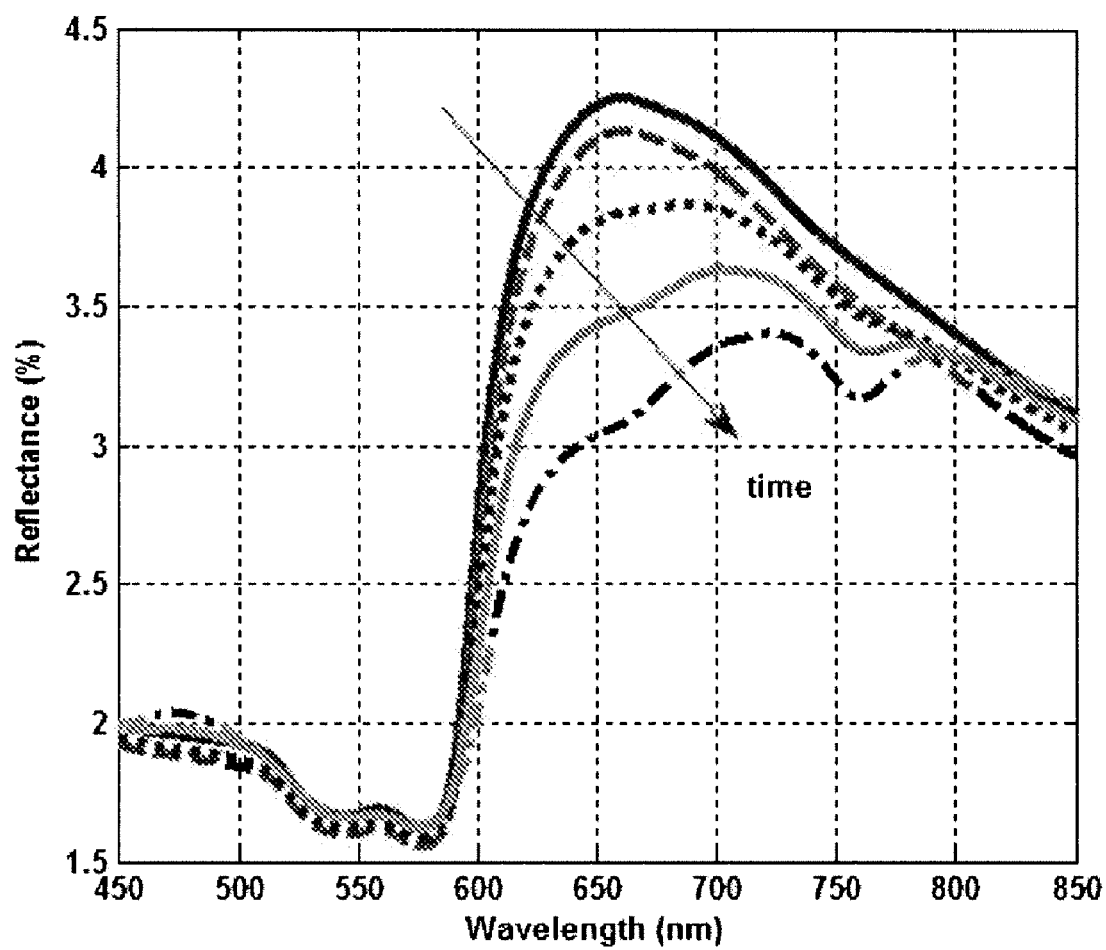
FIG. 35 illustrates the evolution of reflectance spectra over time, associated with a blood sample in a blood culture bottle.

An experimental data set was generated to test the robustness of the above-described model. Two blood culture bottles (BacT/Alert BPA, bioMerieux, Durham, N.C.) were inoculated with 10 μL of normal healthy blood containing approximately 25 CFU of *E. coli* (ATTC strain #25922; Manassas, Va.). One of the seeded bottles was placed into the BacT/ALERT 3D system for comparison. A control bottle, inoculated with 10 mL of blood from the same donor, was run, as well. The bottles were incubated at 37° C. and reflectance measurements were taken every two minutes over a period of 11 hours. FIG. 35 shows representative reflectance spectra of the seeded bottle taken at select time points over the course of the experiment. The trend of transitions over time is illustrated by an arrow in FIG. 35. Similar to FIG. 9, the reflectance spectra progress from oxy-hemoglobin to deoxy-hemoglobin in the presence of actively respiring and reproducing bacteria.

Figure 36:
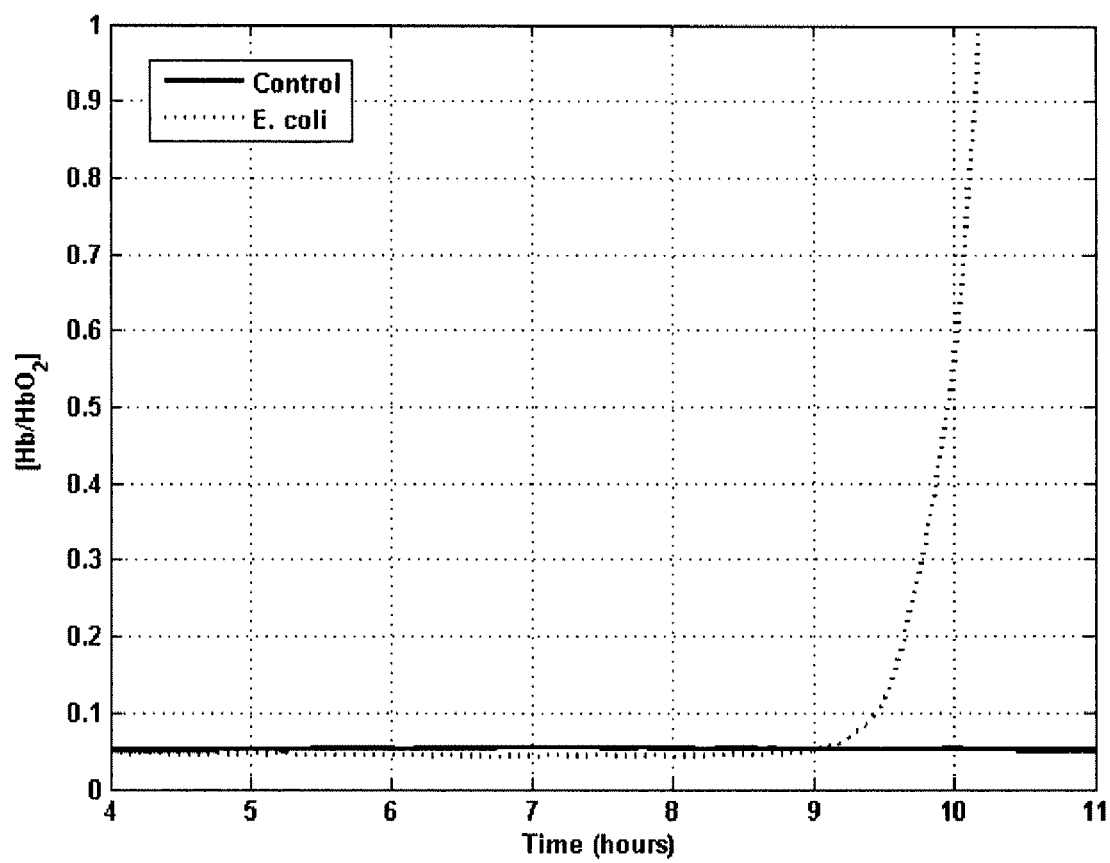
FIG. 36 illustrates the evolution of a ratio of hemoglobin forms over time, associated with a blood sample in a blood culture bottle.
Figure 37:
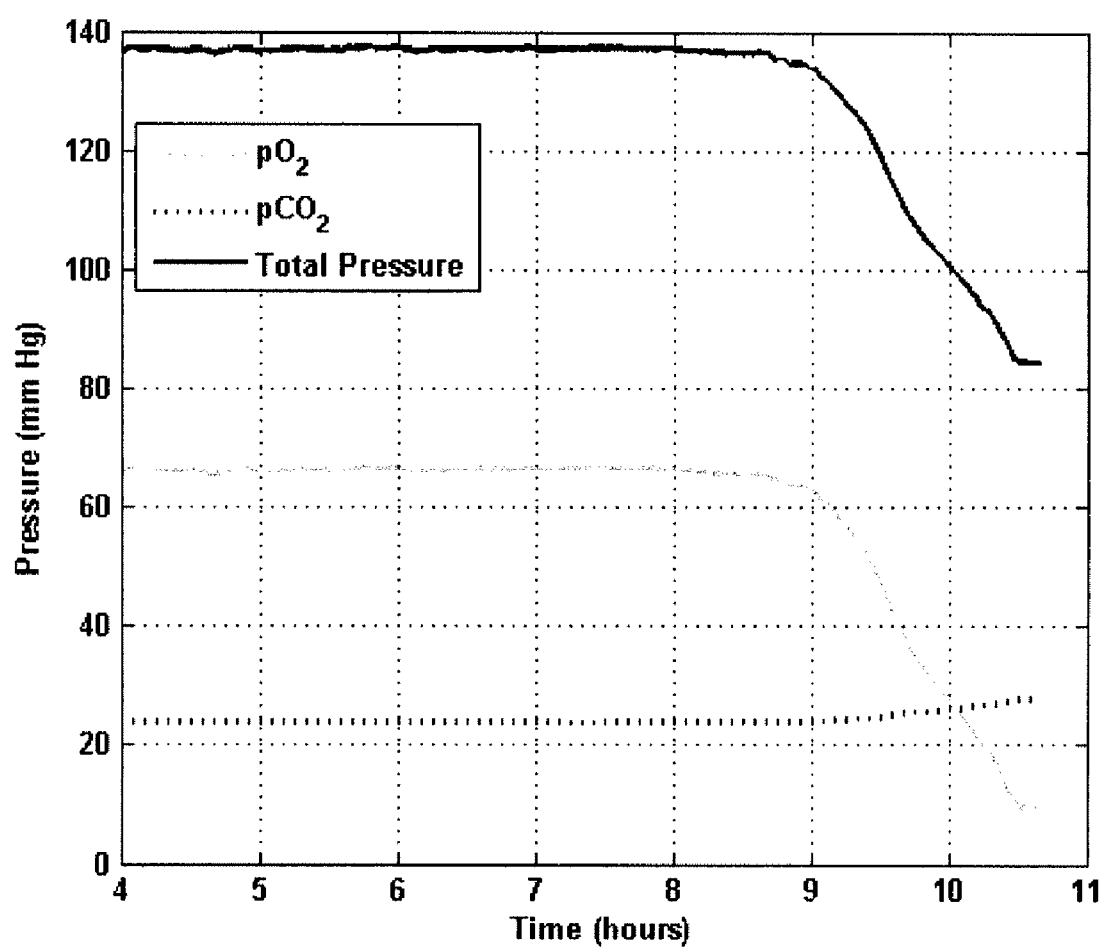
FIG. 37 illustrates the evolution of a ratio of partial gas pressures over time, associated with a blood sample in a blood culture bottle.

As demonstrated in FIG. 36 the ratio of [Hb]/[HbO2] from the bottle containing bacteria diverges from the control between hours 9 and 10, which is at least two hours prior to the positive call for the bottle placed in the BacT/ALERT 3D system (12.2 hours). FIG. 37 reports the corresponding pressures in the headspace over the duration of the experiment. In agreement with the simulation (FIG. 30), both the total pressure and the partial pressure of oxygen decline dramatically as the bacterial respiration exerts its influence on the chemical equilibrium. The high solubility of $CO_2$ results in a less pronounced shift in the partial pressure of $CO_2$ in the headspace.

Accounting for Red Blood Cell Lysis

Figure 38:
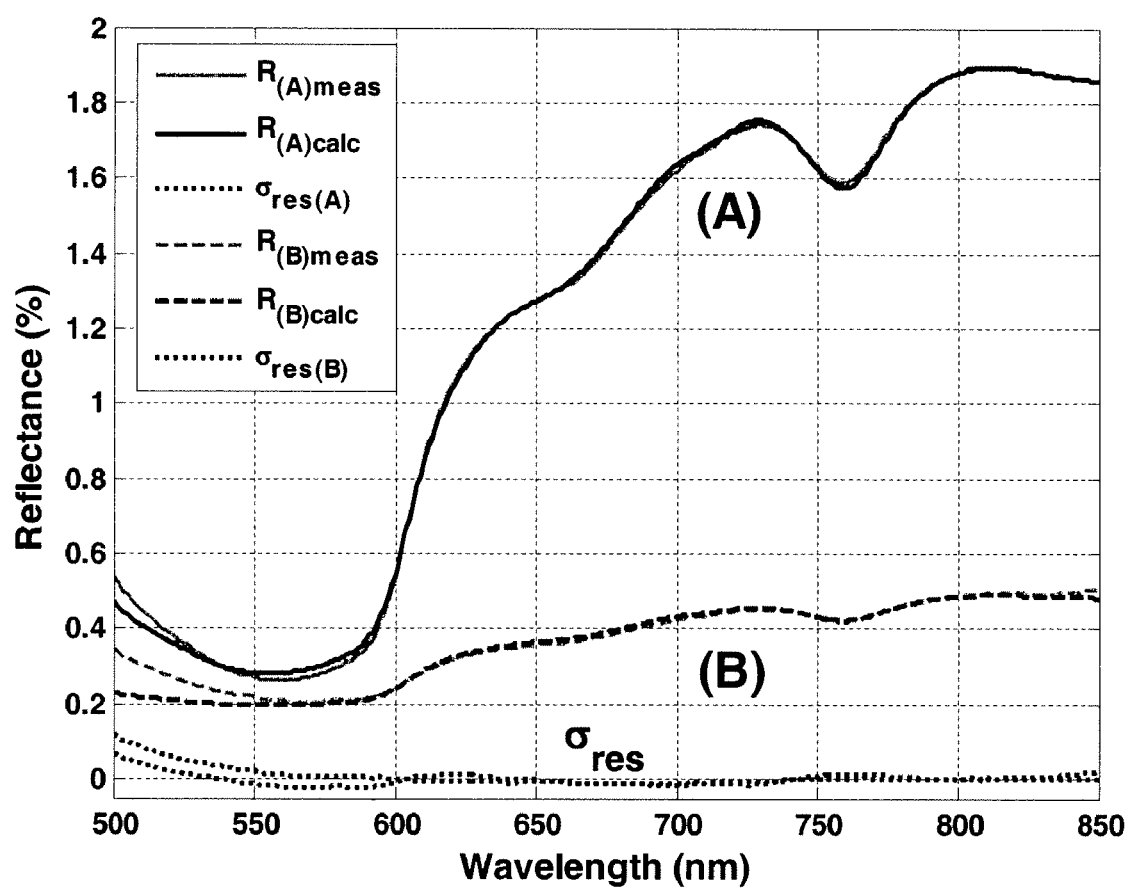
FIG. 38 is a comparison between the measured and calculated reflectance spectra of a blood sample prior to and after hemolysis.

Another important process that may occur in blood cultures is lysis of the erythrocytes. Lysed erythrocytes change the volume fraction, number density and the mean cell volume of particulates in a blood sample. Since erthrocytes are the primary particle population in blood cultures, red blood cell lysis can have an impact on a reflectance signal as demonstrated in FIG. 38. Spectrum A in FIG. 38 represents the diffuse reflectance signal from a blood culture sample prior to hemolysis and spectrum B shows the reflectance signal from the same sample after hemolysis. The observed spectral differences are the collective outcome of the physical changes in the sample, i.e., in the size, volume fraction and number density of particulates as erythrocytes rupture into pieces, and chemical changes resulting from the increased free hemoglobin in the media. These outcomes are represented by the parameters provided in Table 5. Both physical and chemical perturbations of lysis led to the observed decrease in the magnitude of the reflected signal. Scattering decreased with reduced volume fraction of scattering elements and absorption increased with hemoglobin becoming free in solution. Moreover, the reduction of scattering caused the absorptive spectral features in diffuse reflectance to be less pronounced and produced an apparent flattening of the spectrum, as illustrated in FIG. 38. It is therefore evident that, in accordance with the principles of the present invention, accurate mathematical description of these processes in formulation of macroscopic cross-sections, the measured reflectance spectra of samples containing lysed erythrocytes can be suitably predicted and reasonable quantitative estimates of the properties of sample components, such as the exemplary parameters of Table 5, can be obtained.

TABLE 5

PARAMETERS OF BLOOD CULTURE COMPONENTS
OBTAINED FROM DECONVOLUTION OF THE
REFLECTANCE SPECTRA OF FIG. 38

| Deconvoluted blood culture parameters | Spectrum A | Spectrum B |
|---|---|---|
| Volume fraction of erythrocytes in blood culture | 0.068 | 0.055 |
| Number density of erythrocytes in blood culture ($10^8$ cells $ml^{-1}$) | 8.5 | 6.9 |
| Volume fraction of hemoglobin in erythrocytes | 0.32 | 0.32 |
| Mean cell volume of erythrocytes ($\mu m^3$) | 80.0 | 80.0 |
| Fraction of lysed erythrocytes | — | 0.19 |
| Concentration of free hemoglobin in media (g $ml^{-1}$) | <0.0001 | 0.0044 |
| Fraction of deoxyhemoglobin of total hemoglobin | 0.989 | 0.999 |
| Residual sum of squares | 0.015 | 0.030 |

Figure 39:
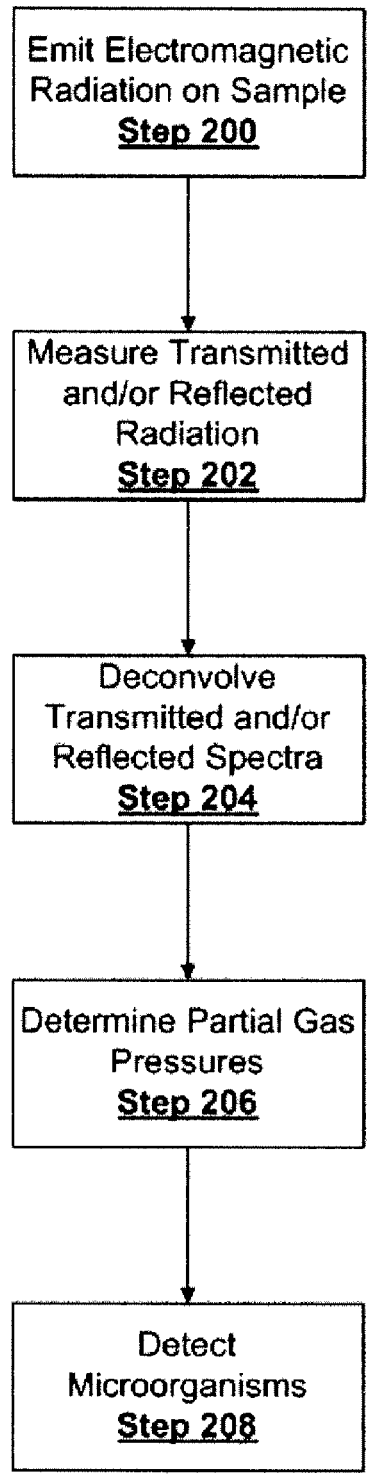
FIG. 39 is a flow diagram that illustrates various exemplary steps associated with detecting microorganisms, using partial gas pressures.

FIG. 39 provides a flow diagram describing the sequence of exemplary steps involved in the detection of microorganisms in a blood sample within a closed container in accordance with the principles of the present invention. Similar to the flow diagram of FIG. 10, in Step 200, one or more blood samples are irradiated with electromagnetic radiation. In Step 202, the reflected and/or transmitted radiations are measured. In Step 204, the detected spectra are deconvolved. In Step 206, the partial pressure of gasses, such as oxygen and carbon dioxide are obtained, using the spectrophotometric data, and in step 208, microorganisms are detected in accordance with at least the partial gas pressures obtained in step 206. Note that the measurement of partial pressures may additionally, or alternatively, be conducted independently from the spectral reflectance and/or transmittance measurements. In such a scenario, the partial gas pressure values obtained from independent measurements may be used in conjunction with the spectral reflectance/transmittance measurements to carry out the deconvolution process to extract all relevant parameters, including, but not limited to, the time to detection of microorganisms.

Properties of Blood Induced by Microbial Metabolites

In accordance with the principles of the present application, identification and/or classification of microorganisms may be also conducted, at least partially or initially, via the detection of changes in the properties of blood that is induced by microbial metabolites. Production of metabolites (such as peroxides, alcohols, aldehydes, sulfides, nitrogen oxides, phospholipase and other lytic enzymes, and the like) during the growth of microorganisms can induce certain modifications in the chemical and/or physical properties of blood components, primarily erythrocytes. Such modifications may include alterations in chemical composition of hemoglobin (i.e., formation of methemoglobin, sulfhemoglobin, nitrohemoglobin, cyanhemoglobin, ferrylhemoglobin, and the like) and/or alterations in morphological structure of erythrocytes (i.e., lysis, swelling, shape transformation, and the like).

Example 1

In this example embodiment, catalase-negative gram-positive bacteria may be discriminated by production of methemoglobin. Catalase is an enzyme that converts hydrogen peroxide, which is a typical by-product of microbial metabolic processes, to molecular oxygen and water. Catalase-negative bacteria lack this enzyme. In clinical labs, the most commonly encountered catalase-negative bacteria are Enterococci (*E. faecium*) and Streptococci (*S. pneumoniae, S. pyogens* (group A), *Streptococcus agalactiae* (group B)). Most staphylococci are catalase-positive with the exception of *S. saccharolyticus* and *S. aureus* subsp. *anaerobius*, which grow more rapidly under anaerobic conditions. Yet, few catalase-negative *S. aureus* (CNSA) have been reported for immuno-suppressed patients (see, for example, Tu and Palutke, 1976; Marake et al., 2005; Yilmaz et al., 2005). One of the primary consequences of the lack of catalase is the production of elevated levels of hydrogen peroxide during the growth of catalase-negative bacteria (see, Moy et al., 2004). Furthermore, most of the catalase-negative bacteria possess hemolytic properties. For example, *S. pyogens* is α-hemolytic *streptococcus* that causes partial lysis of erythrocytes and *S. agalactiae* and *E. faecium* are β-hemolytic that induce a complete rupture of erythrocytes.

Hydrogen peroxide is one of the reactive oxygen species (ROS) that react with hemoglobin to produce methemoglobin (see, for example, Dudok et al., 2004). Therefore, the production of hydrogen peroxide by catalase-negative bacteria in a blood culture leads to the formation of large levels of methemoglobin. This metabolic pathway is different from the typical shift from oxy- to deoxy-hemoglobin, which is observed for the majority of the catalase-positive bacteria, thus enabling the partial identification of the catalase-negative bacteria. Since methemoglobin has unique optical signatures that differentiate this hemoglobin form from other forms of hemoglobin, detection of catalase-negative organisms may be effected using optical monitoring of blood culture bottles.

Example 2

Lytic enzymes released by certain microorganisms during growth may cause hemolysis of erythrocyte, leading to the release of hemoglobin from the cells into the media. This feature is optically detectable since the destruction of erythrocytes modifies optical characteristics of the reflectance and/or transmittance spectra, and aids in partial identification of the microorganisms. Such hemolytic bacteria can be *E. faecium, P. mirabilis*, certain strains of *S. aureus*, and the like. Moreover, α- and β-hemolytic microorganisms can be differentiated since α-hemolytic microorganisms cause only partial hemolysis while β-hemolytic microorganisms destruct red blood cells completely.

Figure 40:
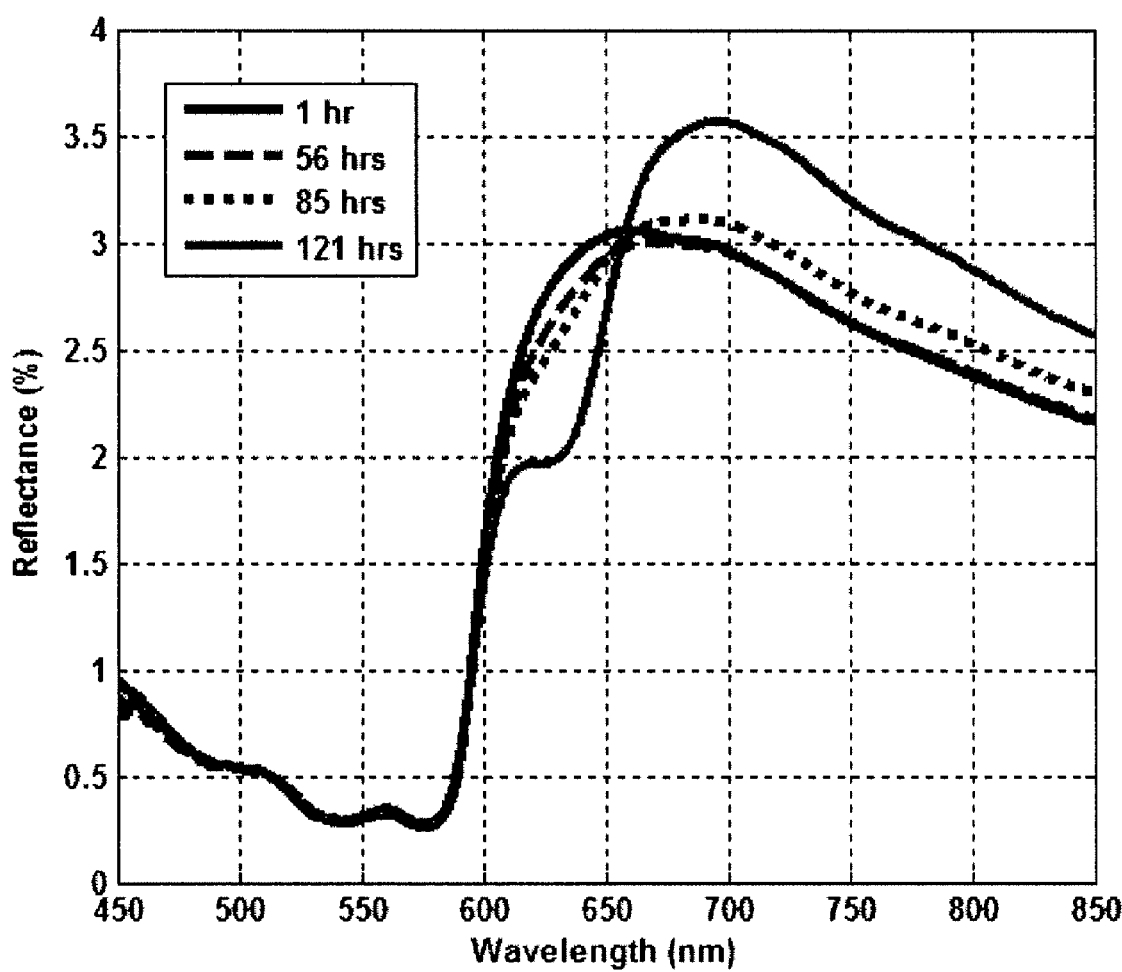
FIG. 40 illustrates an evolution of reflectance spectra over time, associated with a blood sample in a blood culture bottle, which sample is contaminated with bacteria, E. faecium.

Experimental Demonstrations:

The production of methemoglobin and hemolysis in blood cultures caused by microorganism growth may be illustrated in accordance with the following exemplary blood culture experiments involving *E. faecium*. In these experiments, approximately 10 ml of blood was contaminated with approximately 100 CFU of *E. faecium* and incubated at 37° C. with continuous agitation. The measurements of the diffuse reflectance were taken every 20 minutes. FIG. 40 illustrates four selected diffuse reflectance spectra recorded at different time points of a blood culture experiment with *E. faecium*. The characteristic parameters of blood culture, such as fractions of three forms of hemoglobin and volume fraction of the erythrocytes estimated through mathematical deconvolution of the reflectance spectra, are summarized in Table 6.

TABLE 6

PARAMETERS OF BLOOD CULTURE COMPONENTS OBTAINED FROM
DECONVOLUTION OF THE REFLECTANCE SPECTRA OF FIG. 40

| Deconvoluted blood culture parameters | Spectrum A | Spectrum B | Spectrum C | Spectrum D |
|---|---|---|---|---|
| Time step (hrs) | 3.0 | 9.6 | 10.6 | 12.3 |
| Total volume fraction of scatters in blood culture | 0.057 | 0.054 | 0.0460 | 0.018 |
| Volume fraction of hemoglobin in erythrocytes | 0.35 | 0.35 | 0.35 | 0.35 |
| Mean cell volume of erythrocytes ($\mu m^3$) | 92.0 | 92.0 | 92.0 | 92.0 |
| Fraction of oxyhemoglobin of total hemoglobin | 0.956 | 0.933 | 0.850 | 0.260 |
| Fraction of deoxyhemoglobin of total hemoglobin | 0.040 | 0.065 | 0.147 | 0.310 |
| Fraction of methemoglobin of total hemoglobin | 0.0004 | 0.0018 | 0.003 | 0.430 |
| Fraction of lysed erythrocytes | 0.0 | 0.05 | 0.19 | 0.68 |

It can be seen from FIG. 40 and Table 6 that as the fraction of methemoglobin increases and the volume fraction of erythrocytes decreases from spectrum A to spectrum B, and then to C and D, the shape and the magnitude of the reflectance spectra change dramatically.

Figure 41:
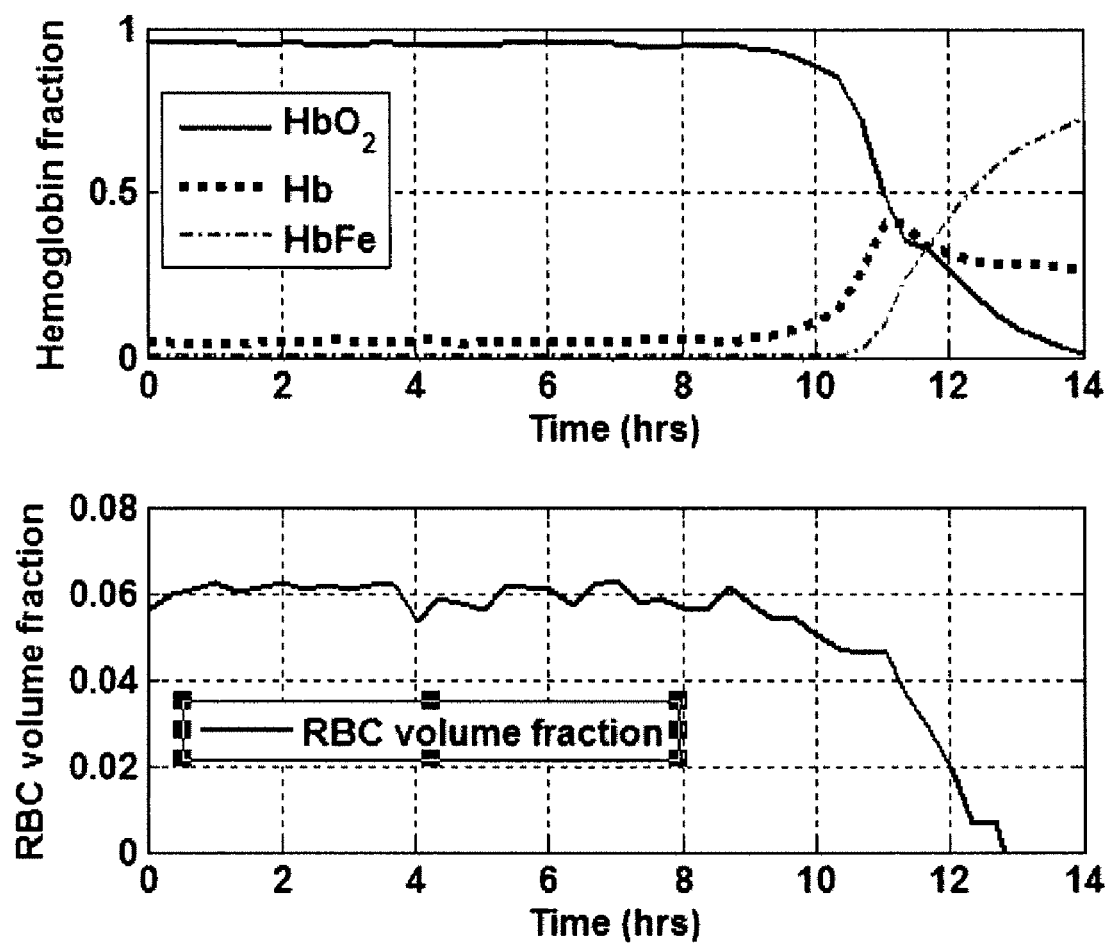
FIG. 41 illustrates the evolution of hemoglobin fraction and red blood cell volume fraction over time, associated with blood samples contaminated with bacteria E. faecium.

The top panel of FIG. 41 demonstrates temporal evolutions of the critical blood culture parameters for duplicate blood culture experiments with *E. faecium*. Note that in FIG. 41, the solid and dashed lines indicate the first and the second experiments, respectively. The sharp decline in oxyhemoglobin and increase in deoxyhemoglobin, evident at approximately 10 hours into the experiments, are consistent with the previous observations for microorganisms in blood culture. It has been shown that bacteria reach concentrations of $10^7$-$10^8$ cells per ml at this time point. Yet, rapid accumulation of methemoglobin occurred shortly afterwards, which is the characteristic of the ROS producing microorganism. In addition, the bottom panel of FIG. 41 shows the temporal progression of the volume fraction of erythrocytes. As evident from FIG. 41, the volume fraction remains relatively constant during the first 9 hours and then starts to decline while reaching nearly zero at 13-14 hours. This complete rupture of erythrocytes is indicative of β-hemolytic microorganism.

The above-described embodiments may be modified or varied, without departing from the invention, as appreciated by those skilled in the art in light of the above teachings. It is therefore to be understood that, within the scope of the claims and their equivalents, the invention may be practiced otherwise than as specifically described.

What is claimed is:

1. A method for assessing the presence of microorganisms in blood, comprising:
   (a) emitting electromagnetic radiation into at least one blood sample;
   (b) measuring wavelength-dependent spectra of reemitted electromagnetic radiation from said blood sample, wherein said measuring is of one or both of transmittance signals and reflectance signals; and then
   (c) deconvoluting said spectra to determine hemoglobin composition and a partial pressure value associated with at least one of oxygen and carbon dioxide, respectively, thereby to assess the presence or absence of microorganisms in said blood sample.

2. A method according to claim 1, wherein said spectra are quantitatively interpreted in terms of the physical and chemical properties of blood.

3. A method according to claim 1, wherein said deconvoluting determines the presence or absence of multiple types of microorganisms in blood.

4. A method according to claim 1, wherein said spectra can be measured as a function of time or at any discrete time point.

5. A method according to claim 1, wherein said measuring is of signals selected from a group consisting of:
   diffuse transmittance signals;
   diffuse reflectance signals;
   angular transmittance signals; and
   angular reflectance signals.

6. A method according to claim 1, wherein said re-emitted electromagnetic radiation comprises wavelengths in the ultraviolet range, the visible range, and/or the near-infrared range.

7. A method according to claim 1, wherein said deconvoluting step quantifies the physical properties of blood components.

8. A method according to claim 1, wherein said deconvoluting step (i) comprises at least one of linear or non-linear models and (ii) resolves said spectra into a particle-related physical characterization.

9. A method according to claim 1, wherein said deconvoluting step identifies and quantifies at least one form of hemoglobin.

10. A method according to claim 1, wherein said assessing comprises detecting the presence or absence of microorganisms.

11. A method according to claim 1, further comprising extracting identifying characteristics of the microorganisms from the spectra, wherein said identifying characteristics are selected from a group consisting of kinetic growth parameters and physical characteristics.

12. A method according to claim 11, wherein the growth parameters include doubling times and respiration rates and the physical characteristics include size and shape.

13. An apparatus configured to assess the presence of microorganisms, comprising:
   (a) a spectrometer configured to measure spectra of a plurality of wavelengths emitting from a sample of blood at a plurality of points in time;
   (b) a transmission cell and/or a reflectance probe operably connected to said spectrometer; and
   (c) a computer that (i) is connected operationally to said spectrometer and (ii) is configured to perform deconvolution on said spectra, thereby to assess the presence or absence of microorganisms in said sample by conducting an operation selected from a group of operations consisting of:
   determining hemoglobin composition and a partial pressure value associated with at least one of oxygen and carbon dioxide, respectively; and
   monitoring changes in hemoglobin composition in said sample.

14. An apparatus according to claim 13, wherein said deconvolution (i) comprises at least one of linear or non-linear regression techniques and (ii) can resolve said spectra into at least one form of hemoglobin.

15. An apparatus according to claim 13, wherein at least one of a reflectance probe and a transmission cell are operably connected to said spectrometer.

16. An apparatus according to claim 13, wherein said spectrometer includes a diode array.

17. An apparatus according to claim 15, wherein a reflectance probe is operably connected to said spectrometer and is configured to operate without making contact with a container in which said sample is located.

18. The method of claim 1, wherein the presence or absence of microorganisms is assessed in accordance with changes in properties of blood induced by one or more microbial metabolites.

19. A method according to claim 18, further comprising identifying at least one microorganism.

20. A method of assessing the presence of at least one microorganism in blood, comprising:
   (a) emitting electromagnetic radiation into at least one blood sample in a thermodynamically closed container;
   (b) measuring wavelength-dependent spectra of re-emitted electromagnetic radiation from said blood sample to obtain measured spectral values, wherein said measuring is of one or both of transmittance signals and reflectance signals;
   (c) measuring partial pressure values associated with at least one of oxygen and carbon dioxide in a headspace above said blood sample to obtain measured partial pressure values;
   (d) deconvoluting said spectra to determine hemoglobin composition in accordance with said measured spectral values and said measured partial pressure values; and
   (e) assessing the presence or absence of microorganisms in accordance with said deconvoluting.

21. A method according to claim 20, wherein said spectra are quantitatively interpreted in terms of the physical and chemical properties of blood.

22. A method according to claim 20, wherein said deconvoluting determines the presence or absence of multiple types of microorganisms in blood.

23. A method according to claim 20, wherein said measuring is of signals selected from a group consisting of:
   diffuse transmittance signals;
   diffuse reflectance signals;
   angular transmittance signals; and
   angular reflectance signals.

24. A method according to claim 20, wherein said re-emitted electromagnetic radiation comprises wavelengths in the ultraviolet range, the visible range, and/or the near-infrared range.

25. A method according to claim 20, wherein said deconvoluting step quantifies the physical properties of blood components.

26. A method according to claim 20, wherein said deconvoluting step (i) comprises at least one of linear or non-linear models and (ii) resolves said spectra into a particle-related physical characterization.

27. A method according to claim 20, wherein said deconvoluting step identifies and quantifies at least one form of hemoglobin.

28. A method according to claim 20, wherein said assessing comprises detecting the presence or absence of microorganisms.

29. A method according to claim 20, further comprising extracting identifying characteristics of the microorganisms from the spectra, wherein said identifying characteristics are selected from a group consisting of kinetic growth parameters and physical characteristics.

30. A method according to claim 29, wherein
   the growth parameters include doubling times and respiration rates; and
   the physical characteristics include size and shape.

31. The method of claim 20, wherein the presence or absence of microorganisms is assessed in accordance with changes in properties of blood induced by one or more microbial metabolites.

32. A method according to claim 31, further comprising identifying at least one microorganism.

33. A method for assessing the presence of microorganisms in blood, comprising:
   (a) emitting electromagnetic radiation into at least one blood sample;
   (b) measuring wavelength-dependent spectra of reemitted electromagnetic radiation from said blood sample at multiple points in time, wherein said measuring is of one or both of transmittance signals and reflectance signals; and then
   (c) deconvoluting said spectra to monitor changes in hemoglobin composition within said blood sample, thereby to assess the presence or absence of microorganisms in said blood sample.

34. A method according to claim 33, wherein said spectra are quantitatively interpreted in terms of the physical and chemical properties of blood.

35. A method according to claim 33, wherein said deconvoluting determines the presence or absence of multiple types of microorganisms in blood.

36. A method according to claim 33, wherein said measuring is of signals selected from a group consisting of:
   diffuse transmittance signals;
   diffuse reflectance signals;
   angular transmittance signals; and
   angular reflectance signals.

37. A method according to claim 33, wherein said re-emitted electromagnetic radiation comprises wavelengths in the ultraviolet range, the visible range, and/or the near-infrared range.

38. A method according to claim 33, wherein said deconvoluting step quantifies the physical properties of blood components.

39. A method according to claim 33, wherein said deconvoluting step (i) comprises at least one of linear or non-linear models and (ii) resolves said spectra into a particle-related physical characterization.

40. A method according to claim 33, wherein said deconvoluting step identifies and quantifies at least one form of hemoglobin.

41. A method according to claim 33, wherein said assessing comprises detecting the presence or absence of microorganisms.

42. A method according to claim 33, further comprising extracting identifying characteristics of the microorganisms from the spectra, wherein said identifying characteristics are selected from a group consisting of kinetic growth parameters and physical characteristics.

43. A method according to claim 42, wherein (A) the growth parameters include doubling times and respiration rates and (B) the physical characteristics include size and shape.

44. A method according to claim 33, wherein partial pressure values associated with at least one of oxygen and carbon dioxide are determined from the deconvoluted spectra.

45. The method of claim 33, wherein the presence or absence of microorganisms is assessed in accordance with changes in properties of blood induced by one or more microbial metabolites.

46. A method according to claim 33, further comprising identifying at least one microorganism.

* * * * *